(12) United States Patent
Javitt et al.

(10) Patent No.: US 12,097,037 B2
(45) Date of Patent: Sep. 24, 2024

(54) SYSTEM, METHOD AND COMPUTER-ACCESSIBLE MEDIUM FOR DETERMINING POSSIBILITY/LIKELIHOOD OF MENTAL DISORDER

(71) Applicants: The Trustees of Columbia University in the City of New York, New York, NY (US); The Nathan S. Kline Institute for Psychiatric Research, Orangeburg, NY (US)

(72) Inventors: Daniel Javitt, Fort Lee, NJ (US); Antigona Martinez, New York, NY (US); Yaakov Stern, New York, NY (US)

(73) Assignees: The Trustees of Columbia University in the City of New York, New York, NY (US); The Nathan S. Kline Institute for Psychiatric Research, Orangeburg, NY (US)

( * ) Notice: Subject to any disclaimer, the term of this patent is extended or adjusted under 35 U.S.C. 154(b) by 458 days.

(21) Appl. No.: 16/624,452

(22) PCT Filed: Jun. 20, 2018

(86) PCT No.: PCT/US2018/038530
§ 371 (c)(1),
(2) Date: Dec. 19, 2019

(87) PCT Pub. No.: WO2018/237023
PCT Pub. Date: Dec. 27, 2018

(65) Prior Publication Data
US 2020/0178834 A1    Jun. 11, 2020

Related U.S. Application Data

(60) Provisional application No. 62/522,410, filed on Jun. 20, 2017.

(51) Int. Cl.
*A61B 5/378* (2021.01)
*A61B 5/00* (2006.01)
*A61B 5/374* (2021.01)

(52) U.S. Cl.
CPC ............. *A61B 5/378* (2021.01); *A61B 5/374* (2021.01); *A61B 5/4088* (2013.01); *A61B 5/7257* (2013.01)

(58) Field of Classification Search
CPC ......... A61B 5/378; A61B 5/316; A61B 5/321; A61B 5/329; A61B 5/33; A61B 5/338;
(Continued)

(56) References Cited

U.S. PATENT DOCUMENTS 9,629,976 B1    4/2017  Acton
2004/0243328 A1*  12/2004  Rapp ................... A61B 5/4094
                                                        702/71
(Continued)

FOREIGN PATENT DOCUMENTS

WO    WO 2016/125159    8/2016

OTHER PUBLICATIONS

Wandell, "Chapter 5: The Retinal Representation," Foundation of Vision, Stanford Univ., Mar. 25, 2016 (Year: 2016).*
(Continued)

*Primary Examiner* — Alex M Valvis
*Assistant Examiner* — Nidhi N Patel
(74) *Attorney, Agent, or Firm* — HUNTON ANDREWS KURTH LLP

(57) ABSTRACT

An exemplary system, method, and computer-accessible medium for generating diagnostic data associated with a likelihood a patient(s) developing a mental disease(s) can be provided, which can include, for example, providing a visual patterns to the patient(s), receiving electroencephalogram (EEG) information from the patient(s) that can be based on
(Continued)

the visual pattern(s); and generating the diagnostic data based on the EEG information.

46 Claims, 17 Drawing Sheets

(58) Field of Classification Search
CPC ......... A61B 5/343; A61B 5/346; A61B 5/347; A61B 5/353; A61B 5/355; A61B 5/357; A61B 5/358; A61B 5/36; A61B 5/367; A61B 5/372; A61B 5/374; A61B 5/388; A61B 5/395; A61B 5/397; A61B 5/4088; A61B 5/7257; A61B 5/4076
See application file for complete search history.

(56) References Cited

U.S. PATENT DOCUMENTS

| | | | |
|---|---|---|---|
| 2010/0249532 A1* | 9/2010 | Maddess | A61B 3/024 600/300 |
| 2013/0208245 A1* | 8/2013 | Campbell | A61B 3/102 351/246 |
| 2017/0035317 A1 | 2/2017 | Jung et al. | |

OTHER PUBLICATIONS

International Search Report for International Application No. PCT/US2018/038530 mailed on Aug. 31, 2018.
International Written Opinion for International Application No. PCT/US2018/038530 mailed on Aug. 31, 2018.
Makeig, "Auditory Event-Related Dynamics of the EEG Spectrum and Effects of Exposure to Tones," Electroencephalography and clinical Neurophysiology, 1993.
Fernandez et al. "Neurophysiologic analyses of low- and high-level visual processing in Alzheimer disease," Neurology, vol. 68, pp. 2006-2076, 2007.
Schellart et al. "Temporal and spatial congruence of components of motion-onset evoked responses investigated by whole-head magneto-electroencephalography," Visual Research 44, 2004.
Albert MS et al. The diagnosis of mild cognitive impairment due to Alzheimer's disease: recommendations from the National Institute on Aging-Alzheimer's Association workgroups on diagnostic guidelines for Alzheimer's disease. Alzheimer's & dementia : the journal of the Alzheimer's Association 2011; 7(3): 270-279.
Dixon ML et al., Interactions between the default network and dorsal attention network vary across 25 default subsystems, time, and cognitive states. Neuroimage 2017; 147: 632-49.
Andrews-Hanna JR et al. Disruption of large-scale brain systems in advanced aging. Neuron 2007; 56(5): 924-35.
Buschke H et al., Evaluating storage, retention, and retrieval in disordered memory and learning. Neurology 1974; 24(11): 1019-25.
Butler PD et al., Sensory contributions to impaired emotion processing in schizophrenia. Schizophr Bull 2009; 35(6): 1095-107.
Butler PD et al., Early-stage visual processing and cortical amplification deficits in schizophrenia. Arch Gen Psychiatry 2005; 62(5): 495-504.
Doniger GM et al., Impaired sensory processing as a basis for object-recognition deficits in schizophrenia. Am J Psychiatry 2001; 158(11): 1818-26.
Green MF et al., Social cognition in schizophrenia. Nat Rev Neurosci 2015; 30 16(10): 620-31.
Hill JM et al., An evaluation of progressive amyloidogenic and pro-inflammatory change in the primary visual cortex and retina in Alzheimer's disease (AD). Frontiers in neuroscience 2014; 8: 347.
Jack CR et al., Transition rates between amyloid and neurodegeneration biomarker states and to dementia: a population-based, longitudinal cohort study. Lancet Neurol 2016; 15(1): 56-64.
Jansen WJ et al. Prevalence of cerebral amyloid pathology in persons without dementia: a meta-analysis. JAMA 2015; 313(19): 1924-38.

Javitt DC. When doors of perception close: bottom-up models of disrupted cognition in schizophrenia. Annual review of clinical psychology 2009; 5: 249-75.
Javitt DC. Neurophysiological models for new treatment development in schizophrenia: early sensory approaches. Ann NY Acad Sci 2015; 1344: 92-104.
Javitt DC et al. Sensory processing dysfunction in the personal experience and neuronal machinery of schizophrenia. Am J Psychiatry 2015; 172(1): 17-31.
Javitt DC et al., Neurophysiological biomarkers for drug development in schizophrenia. Nature reviews 2008; 7(1): 68-83.
Kern RS et al., Theory of mind deficits for processing counterfactual information in persons with chronic schizophrenia. Psychol Med 2009; 39(4): 645-54.
Lakatos P et al., An oscillatory hierarchy controlling neuronal excitability and stimulus processing in the auditory cortex. J Neurophysiol 2005; 94(3): 1904-11.
Lavrencic LM et al., Social cognition is not associated with cognitive reserve in older adults. Neuropsychol Dev Cogn B Aging Neuropsychol Cogn 2016; 23(1): 61-77.
Luck SJ et al., A roadmap for the development and validation of event-related potential biomarkers in schizophrenia research. Biol Psychiatry 2011; 70(1): 28-34.
Makeig S et al., A Mining event-related brain dynamics. Trends Cogn Sci 2004; 8(5): 204-10.
Martinez-Montes E et al., Exploring event-related brain dynamics with tests on complex valued time-frequency representations. Statistics in medicine 2008; 27(15): 2922-47.
Martinez A et al., Neural oscillatory deficits in schizophrenia predict behavioral and neurocognitive impairments. 5 Front Hum Neurosci 2015a; 9(371): 371.
Martinez A et al., Consequences of magnocellular dysfunction on processing attended information in schizophrenia. Cereb Cortex 2012; 22(6): 1282-93.
Martinez A et al., Magnocellular pathway impairment in schizophrenia: evidence from functional magnetic resonance imaging. J Neurosci 2008; 28(30): 7492-500.
Palop JJ et al., Network abnormalities and interneuron dysfunction in Alzheimer disease. Nat Rev Neurosci 2016; 17(12): 777-92.
Power JD et al., Spurious but systematic correlations in functional connectivity MRI networks arise from subject motion. Neuroimage 2012; 59(3): 2142-54.
Power JD et al., Functional network organization of the human brain. Neuron 2011; 72(4): 665-78.
Revheim N et al., Reading impairment and visual processing deficits in schizophrenia. Schizophr Res 2006; 87(1-3): 238-45.
Revheim N et al. Reading deficits in schizophrenia and individuals at high clinical risk: relationship to sensory function, course of illness, and psychosocial outcome. Am J Psychiatry 2014; 171(9): 30 949-59.
Sartucci F et al. Dysfunction of the magnocellular stream in Alzheimer's disease evaluated by pattern electroretinograms and visual evoked potentials. Brain Res Bull 2010; 82(3-4): 169-76.
Schechter I et al., Impairments in generation of early-stage transient visual evoked potentials to magno- and parvocellular-selective stimuli in schizophrenia. Clin Neurophysiol 2005; 116(9): 2204-15.
Sehatpour P et al., Impaired visual object processing across an occipital-frontal-hippocampal brain network in schizophrenia: an integrated neuroimaging study. Arch Gen Psychiatry 2010; 67(8): 772-82.
Schultz AP et al., Phases ofHyperconnectivity and Hypoconnectivity in the Default Mode and Salience Networks Track with Amyloid and Tau in Clinically Normal Individuals. J Neurosci 2017; 37(16): 4323-31.
Sperling RA et al. Amyloid deposition is associated with impaired default network function in older persons without dementia. Neuron 2009; 63(2): 178-88.
Spreng RN et al., Attenuated anticorrelation between the default and dorsal attention networks with aging: evidence from task and rest. Neurobiol Aging 2016; 45: 149-60.
Whitford V et al., Reading impairments in schizophrenia relate to individual differences in phonological processing and oculomotor

(56) References Cited

OTHER PUBLICATIONS control: evidence from a gaze-contingent moving window paradigm. J Exp Psychol Gen 2013; 142(1): 57-75.
Yamasaki T et al. A Potential VEP Biomarker for Mild Cognitive Impairment: Evidence from Selective Visual Deficit of Higher-Level Dorsal Pathway. J Alzheimers Dis 2016; 53(2): 661-76.
Yeo BT et al. The organization of the human cerebral cortex estimated by intrinsic functional connectivity. J Neurophysiol 2011; 106(3): 1125-65.
Yoonessi A, et al., Functional assessment of magno, parvo and konio-cellular pathways; current state and future clinical applications. Journal of ophthalmic & vision research 2011; 6(2): 119-26.
Zhang D et al. Directionality of large-scale resting-state brain networks during eyes open and eyes closed conditions. Frontiers in human neuroscience 2015; 9: 81.
Zhang HY et al., Selective vulnerability related to aging in large-scale resting brain networks. PLoS One 2014a; 9(10): el 08807.
Zhang S et al., Selective attention. Long-range and local circuits for top-down modulation of visual cortex processing. Science 2014b; 345(6197): 660-5.
Kahn RS et al., Schizophrenia Is a Cognitive Illness: Time for a Change in Focus. vol. 70, No. 10, pp. 1107-1112, JAMA Psychiatry, 2013.
Bowie CR et al., 2006. Cognitive deficits and functional outcome in schizophrenia. Neuropsychiatric disease and treatment 2:531-536.
Nuechterlein KH et al., 2008. The MATRICS Consensus Cognitive Battery, part 1: test selection, reliability, and validity. Am J Psychiatry 165:203-213.
Javitt DC. 2009. Sensory processing in schizophrenia: neither simple nor intact. Schizophr Bull 35:1059-1064.
Regan D. 1989. Human Brain Electrophysiology: Evoked Potentials and Evoked Magnetic Fields in Science and Medicine. New York: Elsevier.
Cohen J. Statistical Power Analysis for the Behavioral Sciences, 2nd edition. Hillsdale, NJ: Lawrence Erlbaum Assoc.; 1988.
Talairach J et al., 1988. Co-Planar Stereotaxic Atlas of the Human Brain: 3-Dimensional proportional system: An approach to cerebral imaging. New York, NY: Thieme.
Jin Y, et al. "Topographic analysis of EEG Photic driving in normal and schizophrenic subjects." Clinical Electroencephalogr 26(2):102, Apr. 1995.
Carbonell F, Zet al. "Alzheimer's Disease Neuroimaging I. Optimal Target Region for Subject Classification on the Basis of Amyloid PET Images." J Nucl Med 2015; 56(9): 1351-8.
Javitt DC, "When doors of perception close: bottom-up models of disrupted cognition in schizophrenia."Annual Review Clinical Psychology 5:249-275, 2009.
Javitt DC et al. "Sensory processing dysfunction in the personal experience and neuronal machinery of schizophrenia." Am J Psychiatry 172:17-31, 2015.
Butler PD, et al. "Early-stage visual processing and cortical amplification deficits in schizophrenia." Arch Gen Psychiatry 62:495-504, 2005.
Butler PD, et al. "Subcortical visual dysfunction in schizophrenia drives secondary cortical impairments." Brain 130:417-430, 2007.
Martinez A, et al. "Consequences of Magnocellular Dysfunction on Processing Attended Information in Schizophrenia." Cerebral Cortex 22:1282-1293, 2012.
Woldorff MG, et al. "Retinotopic organization of the early visual spatial attention effects as revealed by PET and ERPs." Human Brain Mapping 5:280-286.
Martinez A, et al. "Involvement of striate and extrastriate visual cortical areas in spatial attention." Nat Neuroscience 2:364-369, 1999.
Di Russo F, et al. "Source analysis of event-related cortical activity during visuo-spatial attention." Cereb Cortex 13:486-499, 2003.
Martinez A, et al. "Magnocellular pathway impairment in schizophrenia: evidence from functional magnetic resonance imaging." Journal of Neuroscience 28:7492 7500, 2008.

Chen Y. "Abnormal visual motion processing in schizophrenia: a review of research progress." Schizophr Bull 37:709-715, 2011.
Chen Y, et al. "Psychophysical isolation of a motion-processing deficit in schizophrenics and their relatives and its association with impaired smooth pursuit." Proc Natl Acad Sci U S A 96:4724-4729, 1999.
Slaghuis WL, et al. "Eye movement and visual motion perception in schizophrenia II: Global coherent motion as a function of target velocity and stimulus density." Exp Brain Res 182:415-426, 2007.
Zeki SM. "Functional organization of a visual area in the posterior bank of the superior temporal sulcus of the rhesus monkey." The Journal of physiology 236:549-573, 1974.
Albright TD. "Direction and orientation selectivity of neurons in visual area MT of the macaque." J Neurophysiol. 52:1106-1130, 1984.
Born RT, Bradley DC. "Structure and function of visual area MT." Annual Review Neuroscience 28:157-189, 2005.
Livingstone M, Hubel D. "Segregation of form, color, movement, and depth: anatomy, physiology, and perception." Science 240:740-749, 1988.
Merigan WH, Maunsell JHR. "How parallel are the primate visual pathways? In: Cowan WM, Shooter EM, Stevens CF, Thompson RF, editors." Ann Rev Neuroscience Palo Alto, CA: Annual Reviews, Inc. p 369-402, 1993.
Nassi JJ, Lyon DC, Callaway EM. "The parvocellular LGN provides a robust disynaptic input to the visual motion area MT." Neuron 50:319-327, 2006.
Braus DF, "Sensory information processing in neuroleptic-naive first-episode schizophrenic patients: a functional magnetic resonance imaging study." Arch Gen Psychiatry 59:696-701, 2002.
Kim D, et al. "Magnocellular contributions to impaired motion processing in schizophrenia." Schizophr Res 82:1-8, 2006.
Chen Y, et al. "Processing of global, but not local, motion direction is deficient in schizophrenia." Schizophr Res 61:215-227, 2003.
Chen Y, et al. "Compromised late-stage motion processing in schizophrenia." Biol Psychiatry 55:834-841, 2004.
Kuba M. "Motion-onset Visual Evoked Potentials and their Diagnostic Application." In. Hradec Králové: Nucleus HK, 2006.
Kuba M, et al. "Motion-onset VEPs: characteristics, methods, and diagnostic use." Vision Res 47:189-202, 2007.
Ahlfors SP, et al. "Spatiotemporal activity of a cortical network for processing visual motion revealed by MEG and fMRI." J Neurophysiol 82:2545-2555, 1999.
Bach M, Ullrich D. "Contrast dependency of motion-onset and pattern-reversal VEPs: interaction of stimulus type, recording site and response component." Vision Res 37:1845 1849, 1997.
McKeefry DJ. "The influence of stimulus chromaticity on the isoluminant motion onset VEP." Vision Res 42:909-922, 2002.
Rice DM, et al. "IEEG alpha photic driving abnormalities in chronic schizophrenia." Psychiatry Res 30:313 324, 1989.
Jin Y, et al. "Topographic analysis of EEG photic driving in normal and schizophrenic subjects." Clinical Electroencephalogr 26:102-107, 1995.
Jin Y, et al. "EEG resonant responses in schizophrenia: a photic driving study with improved harmonic resolution." Schizophr Res 44:213-220, 2000.
Krishnan GP, et al. "Steady state visual evoked potential abnormalities in schizophrenia." Clin Neurophysiol 116:614-624, 2005.
Brenner CA, et al. "Steady state responses: electrophysiological assessment of sensory function in schizophrenia." Schizophr Bull 35:1065-1077, 2009.
Goldstein MR, et al. "Topographic deficits in alpha-range resting EEG activity and steady state visual evoked responses in schizophrenia." Schizophr Res 168:145-152, 2015.
Jin Y, et al. "Abnormal EEG responses to photic stimulation in schizophrenic patients." Schizophr Bull 16:627-634, 1990.
Jin Y, Pet al. "Electroencephalographic photic driving in patients with schizophrenia and depression." Biology Psychiatry 41:496-499, 1997.
Lopes da Silva FH, et al. "Relative contributions of intracortical and thalamo-cortical processes in the generation of alpha rhythms, revealed by partial coherence analysis." Electroencephalogr Clin Neurophysiol 50:449-456, 1980.

(56) References Cited

OTHER PUBLICATIONS

Goldman RI, et al. "Simultaneous EEG and fMRI of the alpha rhythm." Neuroreport 13:2487-2492, 2002.
Liu Z, et al. "Finding thalamic BOLD correlates to posterior alpha EEG." Neuroimage 63:1060-1069, 2012.
Tan HR, Lana L, Uhlhaas PJ. "High-frequency neural oscillations and visual processing deficits in schizophrenia." Frontiers in psychology 4:621, 2013.
Lisman J. "Low-Frequency Brain Oscillations in Schizophrenia." JAMA Psychiatry 73:298-299, 2016.
Mishra J, et al. "Spatial attention boosts short-latency neural responses in human visual cortex." Neuroimage 59:1968-1978, 2012.
Woldorff MG, et al. "The temporal dynamics of the effects in occipital cortex of visual-spatial selective attention." Brain Res Cogn Brain Res 15:1-15, 2002.
Lakatos P, et al. "An oscillatory hierarchy controlling neuronal excitability and stimulus processing in the auditory cortex." J Neurophysiol 94:1904-1911, 2005.
Delorme A, Makeig S. "EEGLAB: an open source toolbox for analysis of single-trial EEG dynamics including independent component analysis." J Neurosci Methods 134:9-21, 2004.
Lopez-Calderon J, Luck SJ. "ERPLAB: an open-source toolbox for the analysis of event-related potentials." Front Hum Neurosci 8:213, 2014.
Tootell RB, et al. "Functional analysis of human MT and related visual cortical areas using magnetic resonance imaging." Journal of Neuroscience 15:3215-3230, 1995.
Cox RW. "AFNI—Software for analysis and visualization of functional magnetic resonance neuroimages." Computers and Biomedical Research 29:162-173, 1996.
Kriegeskorte N, Simmons WK, Bellgowan PS, Baker CI. "Circular analysis in systems neuroscience: the dangers of double dipping." Nat Neurosci 12:535-540, 2009.
Brittain PJ, et al. "Backward and forward visual masking in schizophrenia and its relation to global motion and global form perception." Schizophr Res 124:134-141, 2010.
Byne W, et al. "Postmortem assessment of thalamic nuclear volumes in subjects with schizophrenia." Am J Psychiatry 159:59-65, 2002.
Kemether EM, et al. "Magnetic resonance imaging of mediodorsal, pulvinar, and centromedian nuclei of the thalamus in patients with schizophrenia." Arch Gen Psychiatry 60:983-991, 2003.
Byne W, et al. "Reduction of right medial pulvinar volume and neuron number in schizophrenia." Schizophrenia Res. 90:71-75, 2007.
Buchsbaum MS, et al. "PET and MRI of the thalamus in never-medicated patients with schizophrenia." Am J Psychiatry 153:191-199, 1996.
Hazlett EA, et al. "Abnormal glucose metabolism in the mediodorsal nucleus of the thalamus in schizophrenia." Am J Psychiatry 161:305-313, 2004.
Lakatos P, et al. "The leading sense: supramodal control of neurophysiological context by attention." Neuron 64:419-430, 2009.
Lakatos P, Schroeder C, Letiman DI, Javitt D. 2013. Predictive Suppression of Cortical Excitability and Its Deficit in Schizophrenia. Journal of Neuroscience 33:11692-11702.
Rose VL. 1997. APA practice guideline for the treatment of patients with schizophrenia. American family physician 56:1217-1220.

* cited by examiner

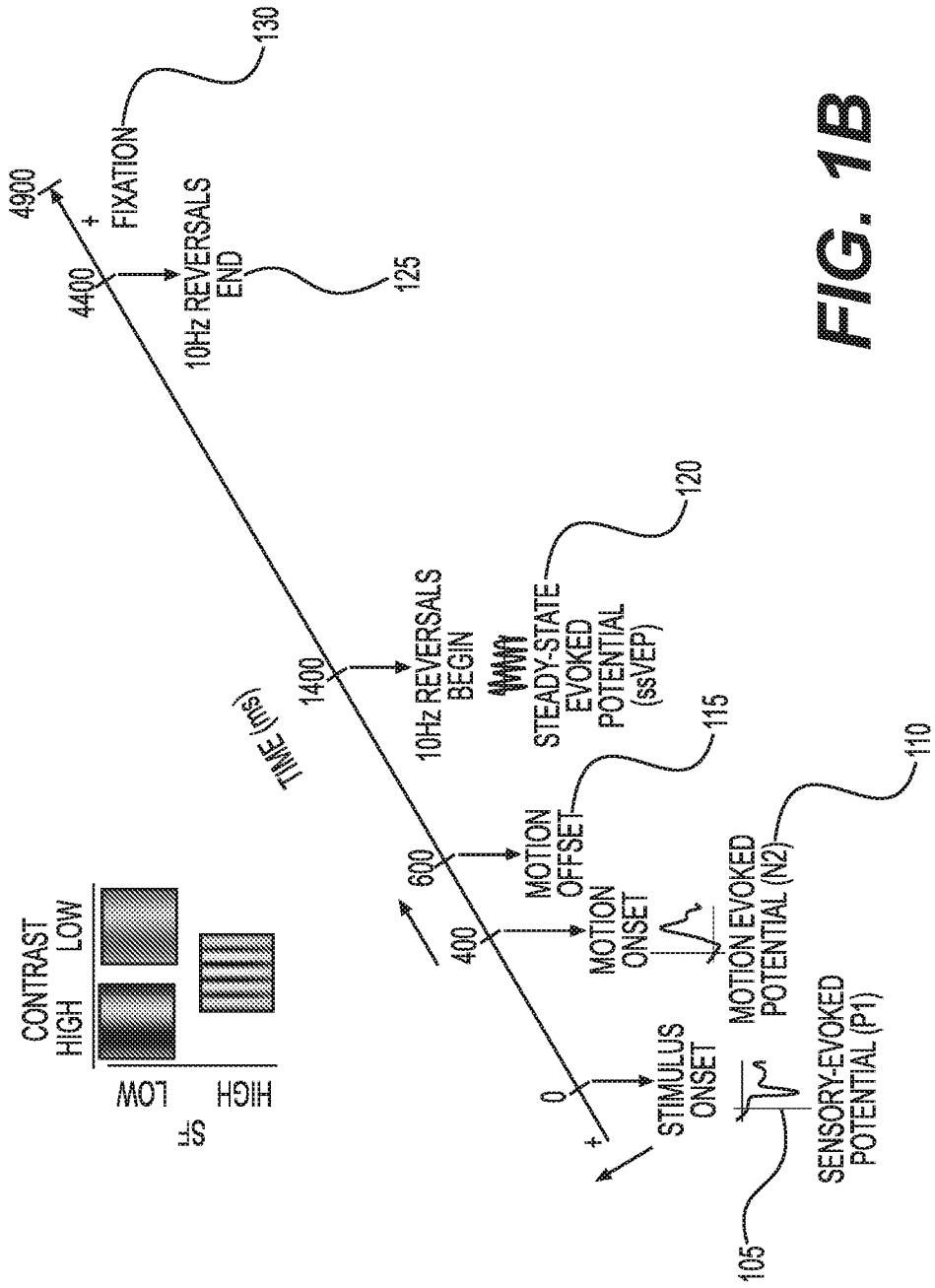

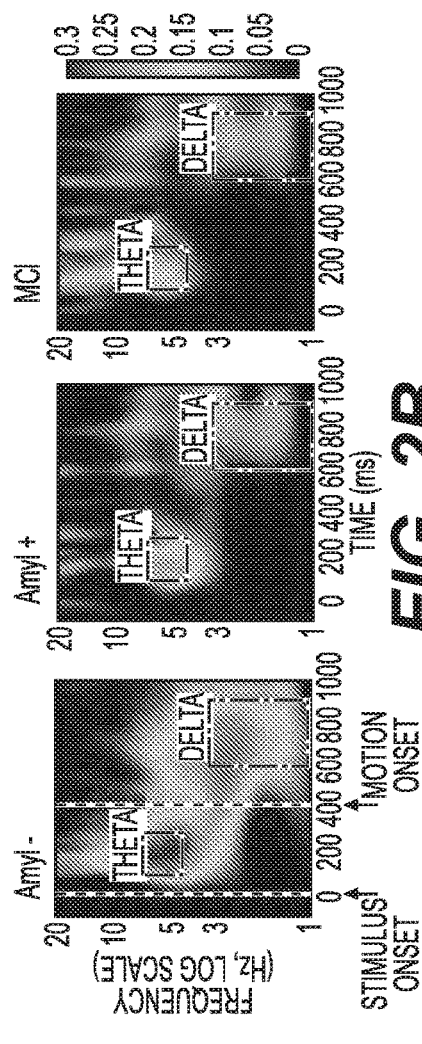
FIG. 2B
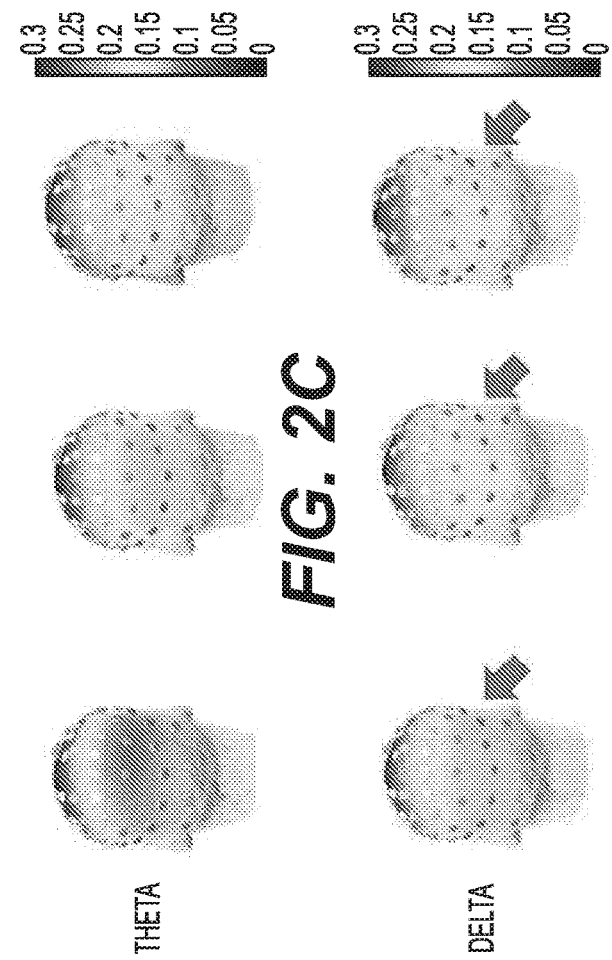
FIG. 2C
FIG. 2D
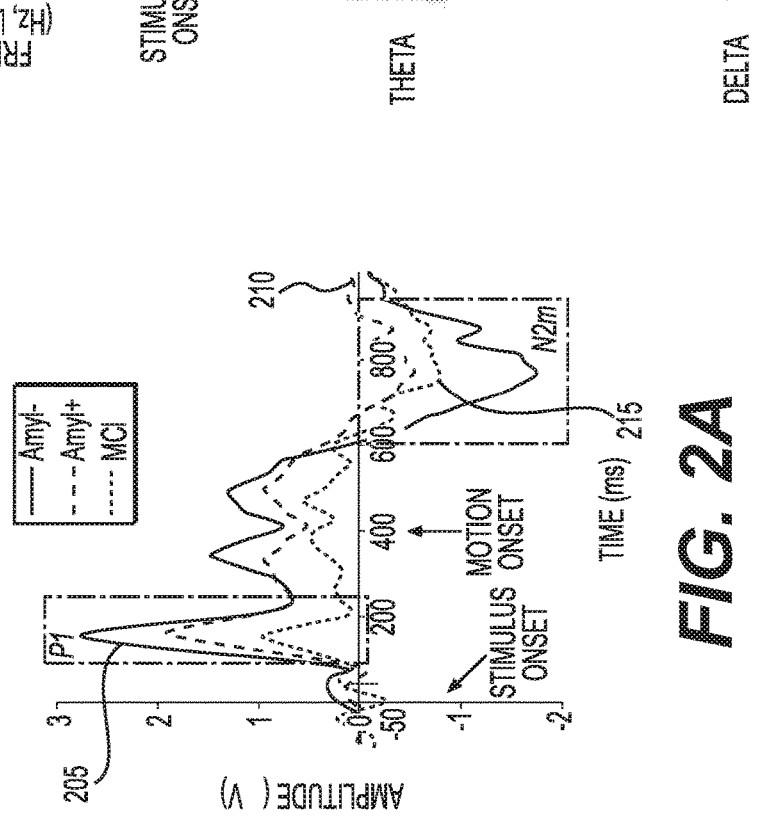
FIG. 2A

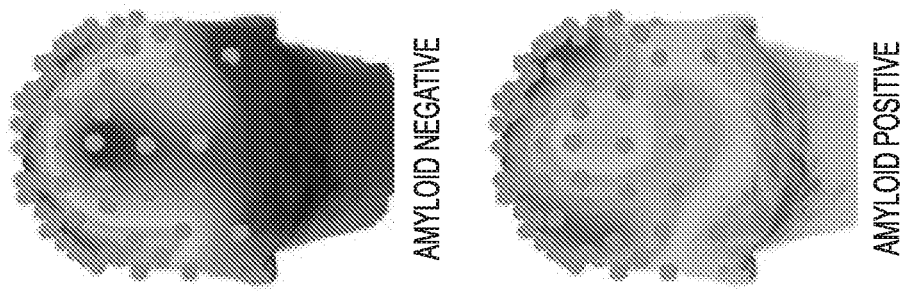
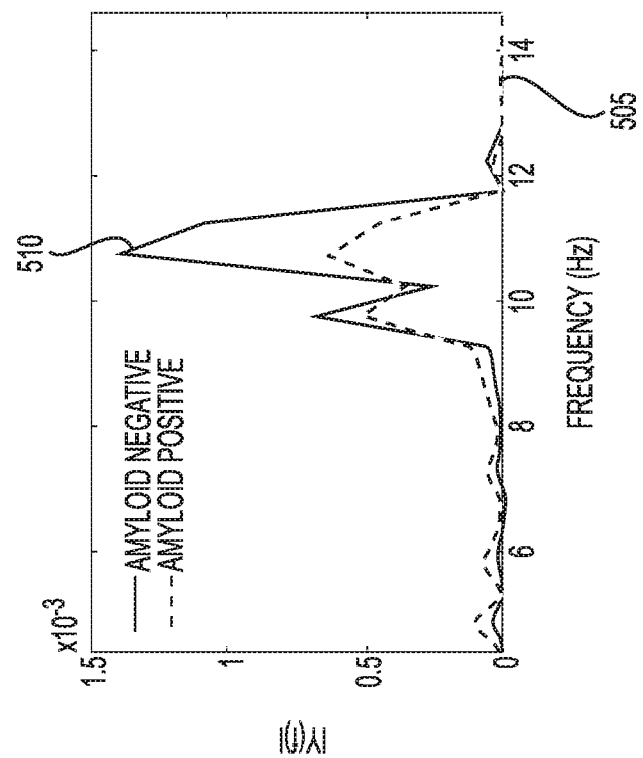
FIG. 5B
FIG. 5A

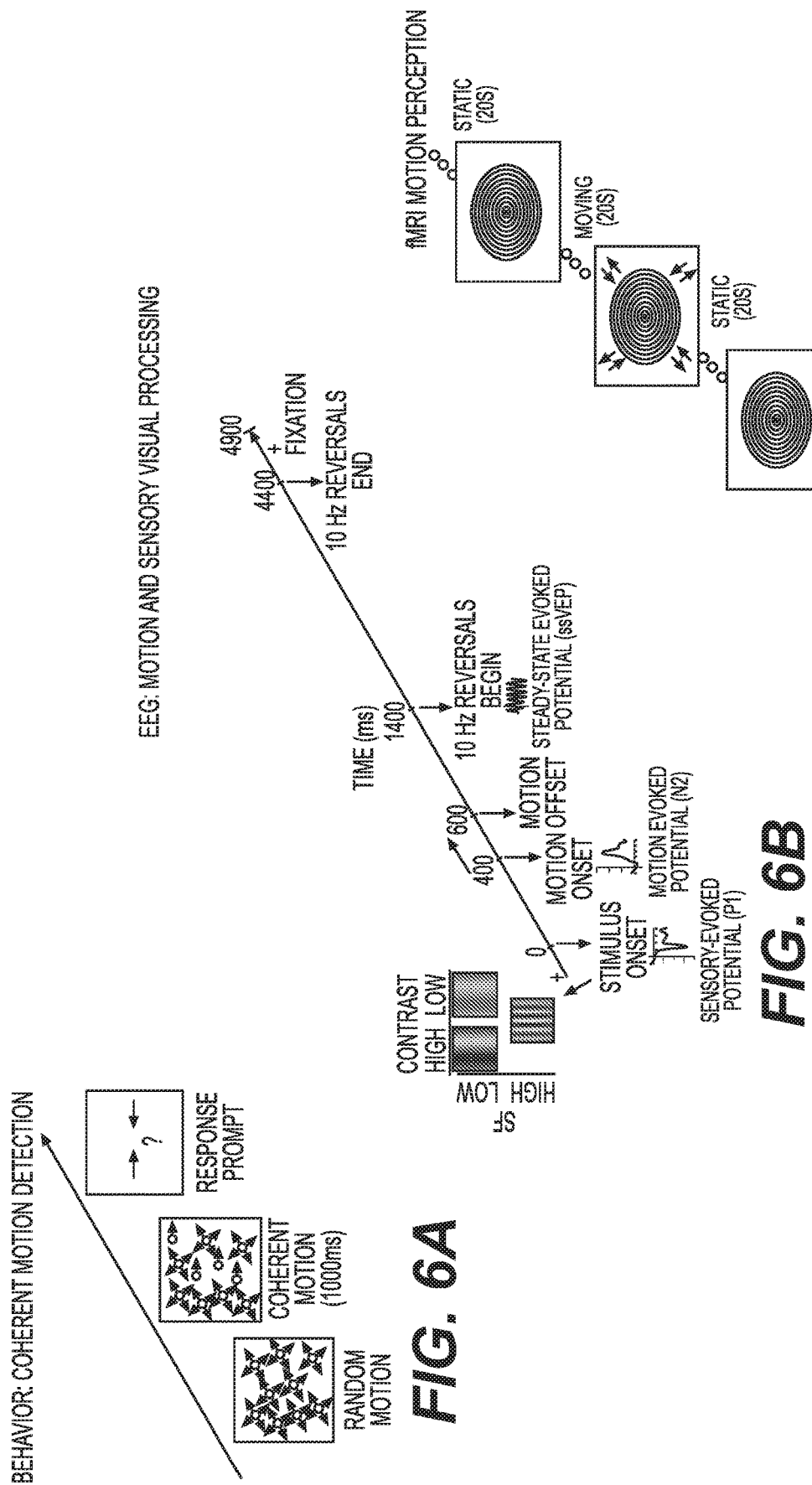

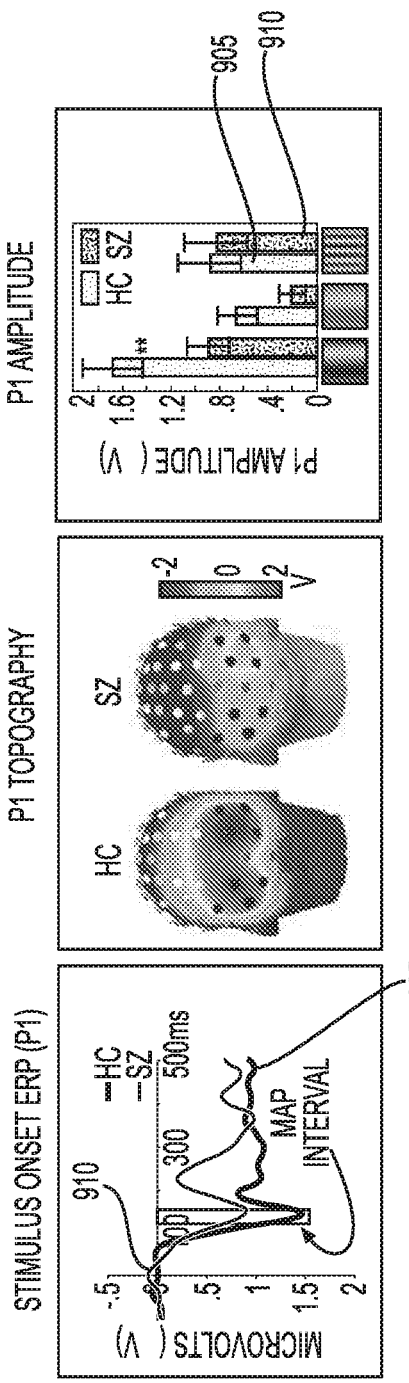
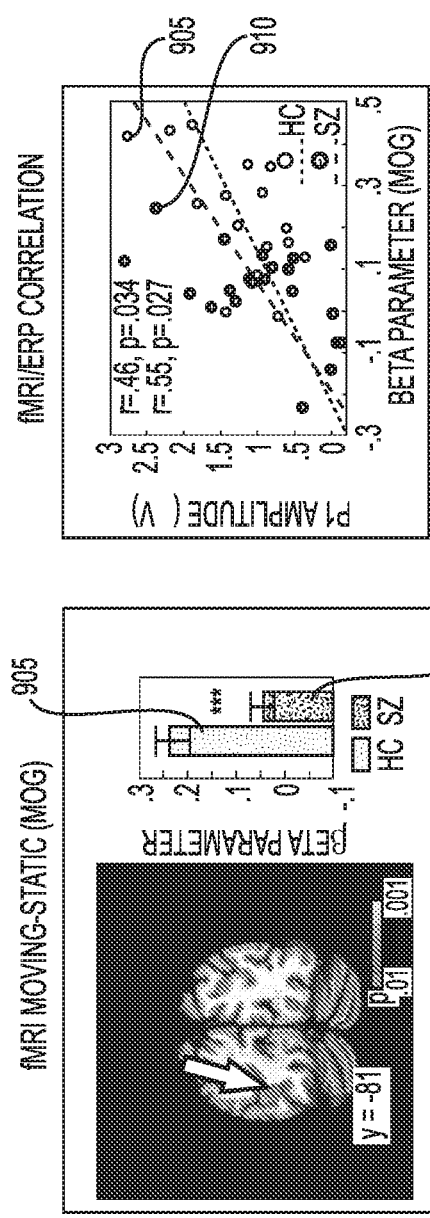

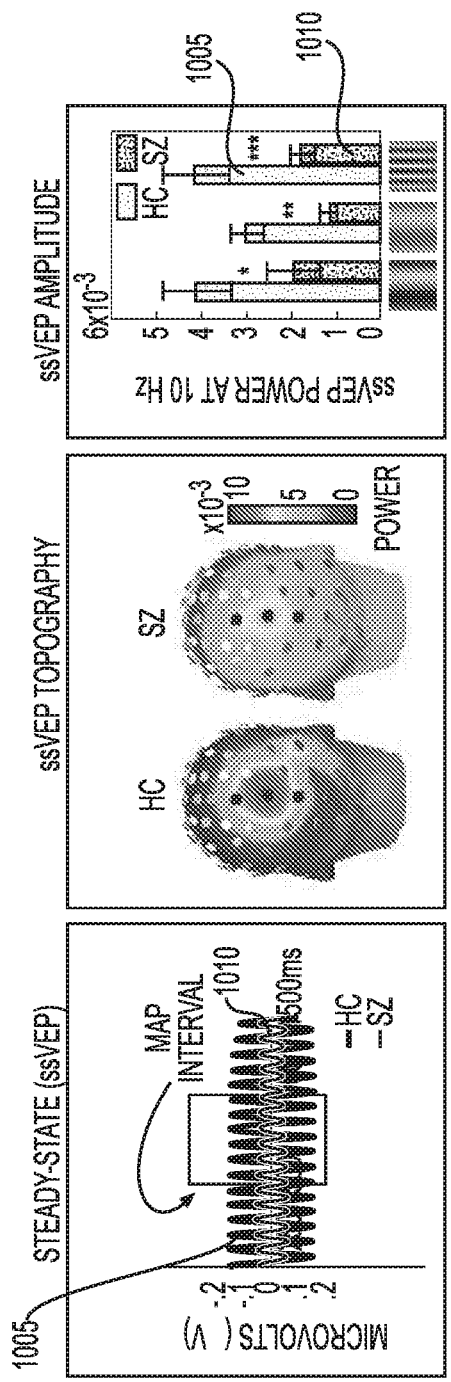
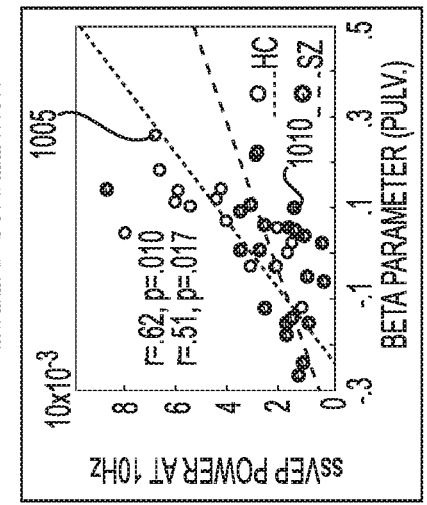
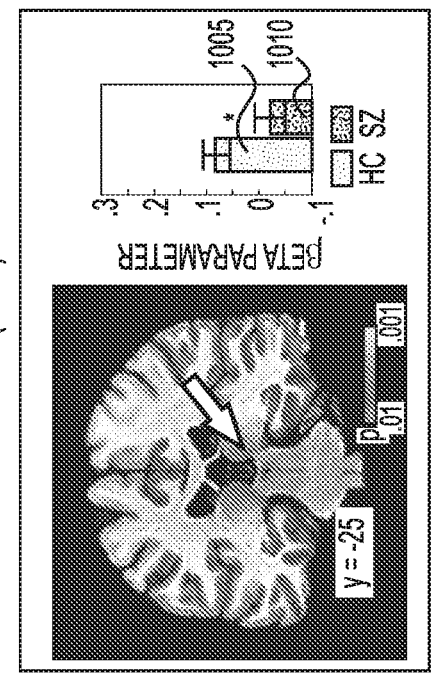
FIG. 10A FIG. 10B FIG. 10C FIG. 10D FIG. 10E

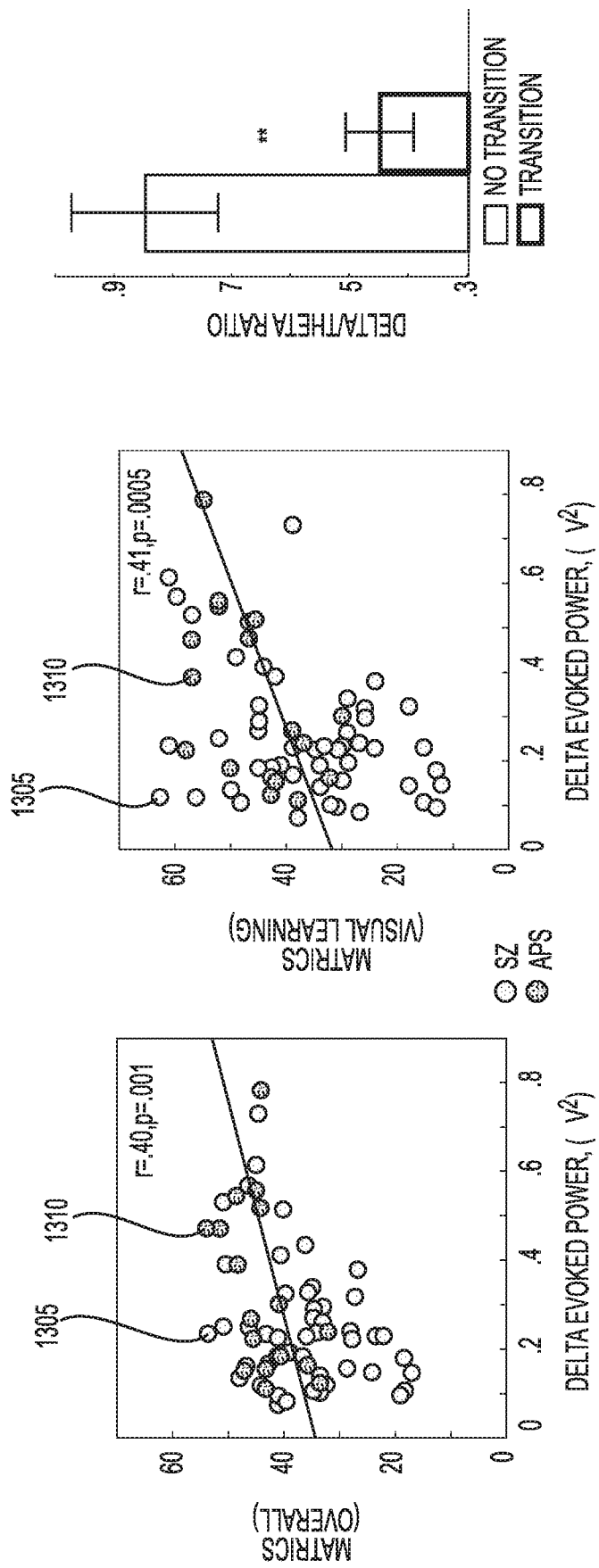

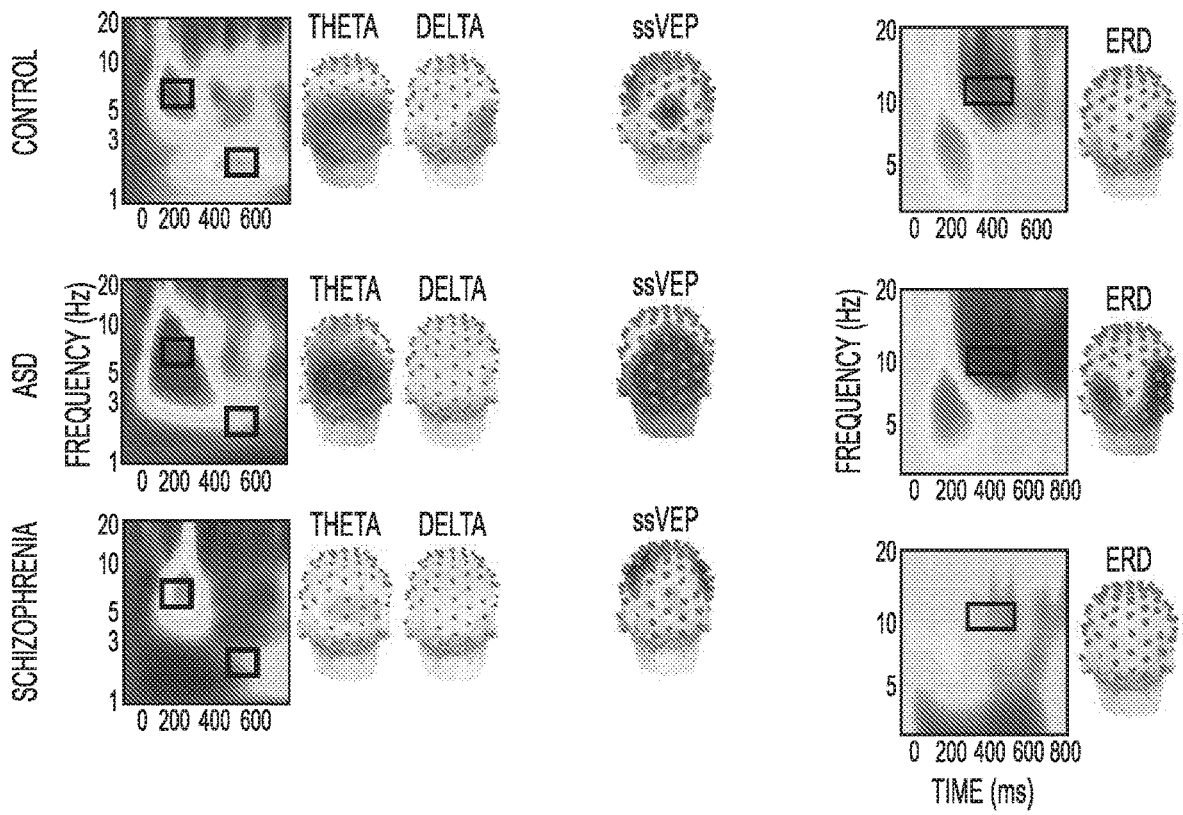
FIG. 14A  FIG. 14C  FIG. 14E
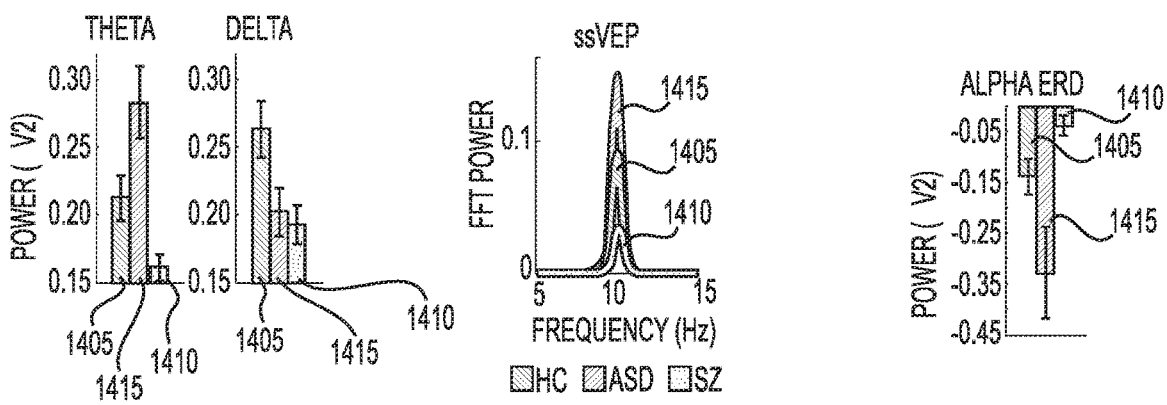
FIG. 14B  FIG. 14D  FIG. 14F

SYSTEM, METHOD AND COMPUTER-ACCESSIBLE MEDIUM FOR DETERMINING POSSIBILITY/LIKELIHOOD OF MENTAL DISORDER

CROSS REFERENCE TO RELATED APPLICATION(S)

The application relates to and claims priority from International Patent Application No. PCT/US2018/038530 filed on Jun. 20, 2018 which was published as International Publication No. WO 2018/237023 on Dec. 27, 2018, and from U.S. Provisional Patent Application Ser. No. 62/522, 410, filed on Jun. 20, 2017, the entire disclosures of which are incorporated herein by reference.

STATEMENT REGARDING FEDERALLY SPONSORED RESEARCH

This invention was made with government support under Grant No. MH049334, awarded by the National Institutes of Health. The government has certain rights in the invention.

FIELD OF THE DISCLOSURE

The present disclosure relates generally to amyloid detection, and more specifically, to exemplary embodiments of an exemplary system, method, and computer-accessible medium for determining a possibility/likelihood of a mental disorder, as well as performing an amyloid detection.

BACKGROUND INFORMATION

Alzheimer disease ("AD") is a devastating illness associated with amyloid and tau deposition and neurodegeneration. When present, amyloid is a strong contributor to neurodegenerative change. For example, in one recent meta-analysis, transition rates of amyloid-positive subjects without signs of neurodegeneration to a neurodegenerative state at age 50 were approximately equivalent to those of a 70-year old without amyloid, and approximately 10-fold higher than those of amyloid negative subjects of equivalent age. (See, e.g., Reference 12). Deposition of plaques, moreover, can precede symptom onset by several decades, providing a window during which preventative treatments can be initiated. (See, e.g., References 6 and 13). Nevertheless, despite the importance of early detection of amyloid status, tests for amyloid detection—including $^{18}F$— Florbetapir PET imaging or cerebral spinal fluid ("CSF") AP amyloid determination—are cumbersome and poorly suited either for large-scale screening. Thus, non-invasive biomarkers sensitive to amyloid status in healthy aging individuals ("elders") are critically needed.

Schizophrenia is a potentially devastating illness characterized by positive symptoms such as hallucinations and agitation; negative symptoms such as apathetic social withdrawal, anhedonia and motor slowing; and cognitive symptoms such as disorientation and cognitive disorganization. In the past, diagnosis is made entirely on the basis of symptoms. Thus, non-invasive biomarkers sensitive to the presence of schizophrenia are needed.

In addition, some individuals show attenuated symptoms of schizophrenia, especially attenuated positive symptoms that can predict subsequent conversion to schizophrenia. Such individuals are thus considered high clinical risk or "prodromal" to schizophrenia. However, among those with attenuated positive symptoms, only approximately 30% convert. At present there are no established methods for distinguishing individuals who will convert to schizophrenia from those who will not. Thus, non-invasive biomarkers for prediction of conversion to schizophrenia among individuals at high clinical risk are needed.

Autism is a potentially devastating neurodevelopmental disorder characterized by differences in patterns of social interaction and communication vs. typically presenting subjects. At present, there are no established biomarkers for diagnosis of autism or autism spectrum disorder ("ASD"), or for differentiating autism spectrum disorders from other neuropsychiatric illness.

Thus, it may be beneficial to provide an exemplary system, method, and computer-accessible medium for amyloid detection, which can overcome at least some of the deficiencies described herein above.

SUMMARY OF EXEMPLARY EMBODIMENTS

An exemplary system, method, and computer-accessible medium for generating diagnostic data associated with a likelihood a patient(s) developing a mental disease(s) can be provided, which can include, for example, providing a visual patterns to the patient(s), receiving electroencephalogram ("EEG") information from the patient(s) that can be based on the visual pattern(s); and generating the diagnostic data based on the EEG information. The diagnostic data can be generated by utilizing (i) a stimulus-onset event-related spectral perturbation (ESRP) procedure, (ii) a motion-onset ESRP procedure, or (iii) a steady-state evoked potential (ssVEP) procedure to the EEG information. The visual pattern(s) can include a low spatial frequency (LSF) stimulus or a high spatial frequency (HSF) stimulus. Responses in the EEG information can be segregated from a subcortical magnocellular and parvocellular visual pathways based on the LSF stimulus or the HSF stimulus.

In some exemplary embodiments of the present disclosure, the diagnostic data can be generated by decomposing neurological responses in the EEG information into a plurality of underlying spectral frequencies. The underlying spectral frequencies can correspond to (i) a predominant event-related spectral perturbation (ESRP) response, (ii) a motion-onset N2m component, or (iii) a steady-state evoked potential (ssVEP). The ESRP response can be in a first frequency range of about 4 Hz to about 7 Hz, the motion-onset N2m component can be in a second frequency range of about 1 Hz to about 4 Hz, and the ssVEP can be at about 8 Hz. The diagnostic data can be related to Alzheimer's disease or Schizophrenia. The diagnostic data can be an amyloid distribution. The patient(s) can be determined to be amyloid negative or amyloid positive.

In certain exemplary embodiments of the present disclosure, a motion onset component can be initiated after providing the visual pattern(s). The motion onset component can be a N2m component. The motion onset component can end, and a stimulus counterphase reversal can be initiated after ending the motion onset component, the stimulus counterphase reversal can then be ended.

A device for providing a visual stimulation(s) to a patient(s) can be provided, which can include, for example a display arrangement configured to provide the visual stimulation(s) to the patient(s), an EEG arrangement configured to generate EEG information based on the visual stimulation(s) provided to the patient(s), and a computer arrangement configured to generate diagnostic data based on the EEG information. The visual stimulation(s) can be a pattern(s). The pattern(s) can include a low spatial frequency stimulus and a high spatial frequency stimulus. The pattern(s) can include a vertical grating.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIG. 1A is an exemplary diagram of an optimized visual stimulation according to an exemplary embodiment of the present disclosure;

FIG. 1B is an exemplary chart illustrating timing of a stimulus presentation according to an exemplary embodiment of the present disclosure;

FIG. 2A is an exemplary chart illustrating event-related spectral perturbation elicited by stimulus (P1) and motion (N2m) onset according to an exemplary embodiment of the present disclosure;

FIG. 2B is a set of exemplary images of time-frequency (e.g., event-related spectral perturbation) response to stimulus onset (theta) and motion onset (delta) according to an exemplary embodiment of the present disclosure;

FIG. 2C is a set of exemplary head maps of stimulus-onset theta activity by group according to an exemplary embodiment of the present disclosure;

FIG. 2D is a set of exemplary head maps of motion-onset delta activity by group according to an exemplary embodiment of the present disclosure;

FIG. 5A is a diagram illustrating an exemplary steady-state response amplitude according to an exemplary embodiment of the present disclosure;

FIG. 5B is a further diagram illustrating an exemplary steady-state scalp distribution according to an exemplary embodiment of the present disclosure;

FIG. 6A is a diagram illustrating an exemplary coherent motion discrimination according to an exemplary embodiment of the present disclosure;

FIG. 6B is a diagram illustrating an exemplary EEG and stimuli according to an exemplary embodiment of the present disclosure;

FIG. 6C is a diagram illustrating an exemplary use of fMRI according to an exemplary embodiment of the present disclosure;

FIG. 9A is a chart illustrating exemplary ERPs to stimulus onset according to an exemplary embodiment of the present disclosure;

FIG. 9B is set of exemplary images of scalp topography of the P1 according to an exemplary embodiment of the present disclosure;

FIG. 9C is a chart illustrating an exemplary P1 amplitude for each stimulus type according to an exemplary embodiment of the present disclosure;

FIG. 9D is an exemplary image and chart illustrating activation of MOG to moving stimuli according to an exemplary embodiment of the present disclosure;

FIG. 9E is a chart illustrating an exemplary correlation between MOG activation and P1 amplitude according to an exemplary embodiment of the present disclosure;

FIG. 10A is a diagram illustrating exemplary ssVEP responses to 10 HZ flicker according to an exemplary embodiment of the present disclosure;

FIG. 10B is a set of exemplary images of scalp topography of the P1 according to an exemplary embodiment of the present disclosure;

FIG. 10C is a chart illustrating an exemplary FFT power at 10 HZ for each stimulus type according to an exemplary embodiment of the present disclosure;

FIG. 10D is an exemplary image and chart illustrating the activation of the pulvinar to moving stimuli according to an exemplary embodiment of the present disclosure;

FIG. 10E is a chart illustrating an exemplary correlation between pulvinar activation and ssVEP power according to an exemplary embodiment of the present disclosure;

FIG. 13A is a set of charts illustrating an exemplary correspondence between delta evoked power and overall scores on the MATRICS cognitive battery and visual learning scores, according to an exemplary embodiment of the present disclosure;

FIG. 13B is an exemplary chart showing differences in Delta/Theta ratio between clinical high risk (attenuated psychosis) patients who transition to schizophrenia vs. those who do not according to an exemplary embodiment of the present disclosure;

FIG. 14A is an exemplary set of time-frequency plots and scalp distributions of theta and delta evoked power according to an exemplary embodiment of the present disclosure;

FIG. 14B is a set of charts illustrating an exemplary evoked theta and delta power for each stimulus type according to an exemplary embodiment of the present disclosure;

FIG. 14C is an exemplary set of scalp distributions for the ssVEP response according to an exemplary embodiment of the present disclosure;

FIG. 14D is an exemplary plot of steady-state visual evoked potential power according to an exemplary embodiment of the present disclosure;

FIG. 14E is a set of time-frequency charts and scalp distributions for total power and alpha event-related desynchronization ("ERD") according to an exemplary embodiment of the present disclosure;

FIG. 14F is an exemplary plot of alpha event-related desynchronization according to an exemplary embodiment of the present disclosure;

Figures 3A, 3B, 3C:
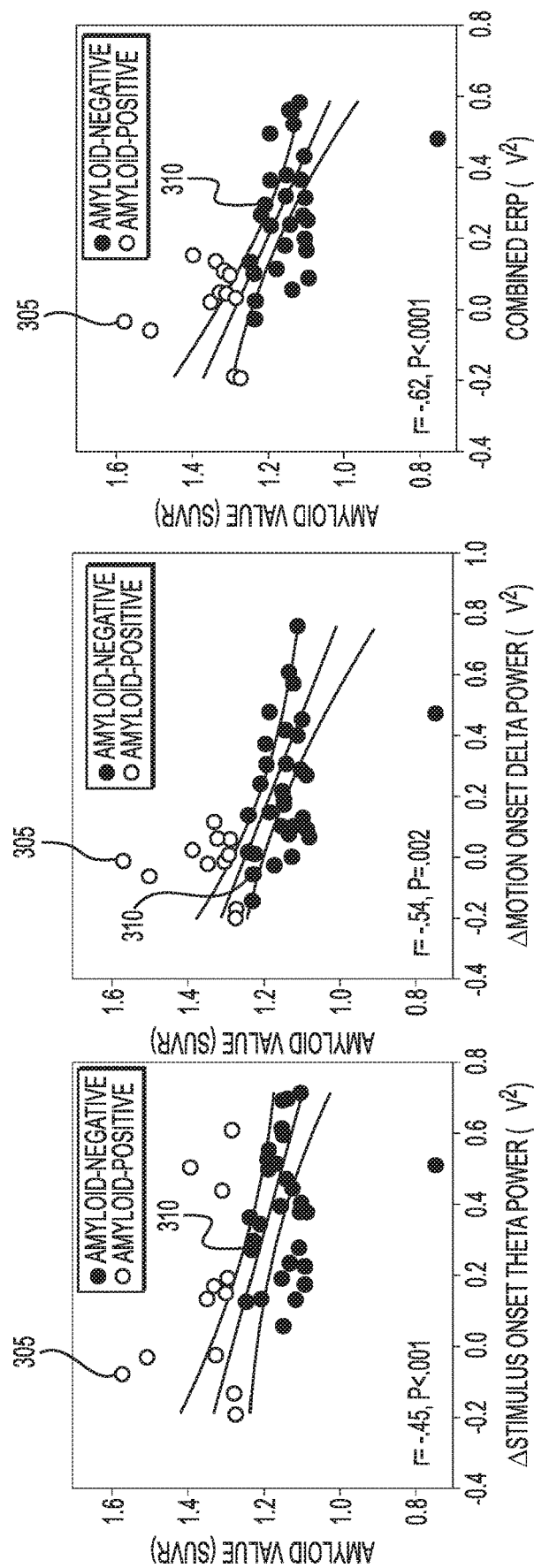
FIGS. 3A-3C are charts illustrating exemplary correlations between global amyloid values and motion-onset (theta) activity according to an exemplary embodiment of the present disclosure.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

The exemplary system, method, and computer-accessible medium, according to an exemplary embodiment of the present disclosure, can utilize visual event-related spectral perturbation ("ERSP") measures as indices of amyloid deposition in the brain. In contrast to other types of evaluations, ERSP can be well suited for early diagnosis and detection in that they can be easy to implement and produce consistent results across various populations. In addition, recent work has been performed to optimize visual ERSP approaches for detection of disorders such as schizophrenia, which can be associated with glutamatergic deficits affecting the early visual system. (See, e.g., Reference 16). These advances can include a development of optimized stimulation approaches, along with "time-frequency" analytic approaches that substantially increases sensitivity of the procedure for detecting cross-subject differences. (See, e.g., References 16, 17, and 21). Neurophysiological measures can also be useful for the detection of individuals at high risk for psychotic disorders based upon either early (e.g., prodromal) clinical symptoms (e.g., including attenuated positive symptoms) or genetic background. Neurophysiological and functional imaging measures involving the visual system can also be useful for the detection of individuals suffering from autism or ASD.

In AD, amyloid deposition can be observed not only in frontotemporal regions, but also parieto-occipital cortex and lower tiers of the visual system including the retina. (See, e.g., Reference 11). Further, cortical regions including primary and secondary visual cortex such as calcarine sulcus and middle occipital gyms ("MOG") show high specificity for differentiating amyloid-positive from amyloid-negative subjects, albeit with lower sensitivity than "optimal" regions such as precuneus, medial frontal or temporo-parietal cortex. (See, e.g., Reference 6). Nevertheless, the high precision with which visual regions can be probed using neurophysiological procedures can compensate for the somewhat lower amyloid levels in visual cortex vs. other brain regions. Moreover, the visual cortex can be modulated by higher order regions such as the cingulate cortex (see, e.g., Reference 47) such that deficits in visual ERSP generation can also reflect dysfunction within larger cortical circuits.

The exemplary system, method, and computer-accessible medium, according to an exemplary embodiment of the present disclosure, can utilize an efficient visual ERSP approach in which stimulus-onset ERSP motion-onset ERSP and steady-state evoked potential ("ssVEP") can be interleaved and neuro-oscillatory (e.g., "time frequency") approaches were used to analyze resulting neural activity. This can minimize refractoriness of individual components, and thus can maximize efficiency and signal-to-noise. Both low spatial frequency ("LSF") and high spatial frequency ("HSF") stimuli can be used to help segregate responses from the subcortical magnocellular and parvocellular visual pathways. LSF stimuli can bias activity toward the magnocellular visual system, whereas HSF stimuli can bias activity to the parvocellular system.

Similarly, low (e.g., <8%) stimulus contrast preferentially engages the magnocellular system. In schizophrenia, preferential deficits can be observed in activation of the subcortical magnocellular vs. parvocellular visual pathway related to underlying dysfunction of N-methyl-D-aspartate ("NMDA") receptor-mediated neurotransmission. (See, e.g., References 5, 24, 26, and 36). By contrast, to the extent that amyloid deposition occurs primarily in cortical vs. subcortical visual structures, more balanced deficits to LSF vs. HSF stimuli can be expected.

Data were analyzed using a "time frequency" neuro-oscillatory approach, in which neurophysiological responses were first decomposed into underlying spectral frequencies prior to analysis. This approach increases the power for separating stimulus-induced activity (e.g., "signal") from ongoing EEG (e.g., "noise) and also provides enhanced understanding of underlying processes at the local circuit level. (See, e.g., References 15-17, 22, and 23.

Specific dependent measures included the (i) the stimulus onset-induced visual P1 component, which shows a predominant ERSP response in the theta (e.g., 4-7 Hz) frequency range; (ii) the motion-onset N2m component, which shows a predominant ERSP response in the delta (e.g., 1-4 Hz) range; and (iii) the ssVEP, which occurs at the 8 Hz steady-state stimulation frequency. Generators for these can be primarily localized to MOG and middle temporal (e.g., MT+) regions, respectively. For each component, evoked power within the indicated frequency band was used as the primary experimental measure. The relationship of these measures to regional and voxel-wise amyloid SUVR was analyzed.

The relationship between the exemplary visual ERSP measures and resting state functional connectivity fMRI ("fcMRI") measures obtained independently on these subjects were also analyzed. In AD, the greatest effects of amyloid deposition were observed in relationship to default mode networks ("DMN"), especially involving long connection paths. (See, e.g., Reference 30). In normal aging, however, the greatest effects can be observed in executive control and dorsal attention ("DAN") networks (see, e.g., References 2 and 46), which can be known to exert top-down control over visual ("VIS") network function. (See, e.g., Reference 45). By contrast, VIS network connectivity itself may not be significantly affected by either aging or AD. (See, e.g., Reference 2, 30, and 45). Here, the potential relationship of the exemplary visual ERSP measures to local vs. top-down dyscontrol was evaluated using a combined regional amyloid and fcMRI approach.

When utilizing the exemplary system, method, and computer-accessible medium, it was determined that (i) that ERSP measures could reliably discriminate between amyloid-negative participants and both amyloid-positive and MCI groups, supporting their use as surrogate biomarkers for amyloid deposition; (ii) that these effects can relate to patterns of regional amyloid distribution in healthy elders even in the absence of cognitive symptoms, and (iii) that amyloid effects can be mediated by well described effects of amyloid on functional connectivity within networks known to exert top-down control on visual sensory processing.

EXEMPLARY METHODS

Exemplary Subjects—Healthy Elders

A total of 43 healthy elders were recruited from an ongoing study of cognitive aging, which assesses longitudinal function over time, and includes measures of overall cognition, amyloid deposition, and fcMRI.

Participants were recruited using a market-mailing approach. Participants who responded to the mailing were telephone screened to ensure they met basic inclusion criteria (e.g., right handed, English speaking, no psychiatric or neurological disorders, normal or corrected-to-normal vision). All participants found eligible via the initial telephone screen were further screened in person with structured medical, neurological, psychiatric, and neuropsychological evaluations to ensure that they had no neurological or psychiatric disease or cognitive impairment.

The screening procedure included a detailed interview that excluded individuals with a self-reported history of major or unstable medical illness, significant neurological history (e.g., epilepsy, brain tumor, stroke), history of head trauma with loss of consciousness for greater than 5 minutes or history of Axis I psychiatric disorder (e.g., APA, 1994). Individuals taking psychotropic medications were also excluded. Global cognitive functioning was assessed with the Mattis Dementia Rating Scale, on which a score of at least 135 was utilized for retention. (See, e.g., Reference 29).

In addition, a neuropsychological battery including the Selective Reminding Task ("SRT") (see, e.g., Reference 3) established that participants were cognitively normal and did not meet criteria for mild cognitive impairment ("MCI"). As part of the parent study, all elders were offered amyloid PET. During the period of the current study, all elders who had recently completed and amyloid PET scan were referred for the EEG studies. In addition, a group of 9 patients were recruited from an ongoing study of MCI. Subjects were of similar age to the healthy elders but met National Institute on Aging guidelines criteria for MCI. (See, e.g., Reference 1). Demographics are shown in Table 1 below.

TABLE 1

| | Demographics (mean ± sd) | | |
|---|---|---|---|
| Group | Amyloid-negative (n = 29) | Amyloid-positive (n = 14) | Mild Cognitive Impairment (n = 9) |
| Age (yr) | 65.5 ± 2.9 | 64.6 ± 2.8 | 64.2 ± 6.9 |
| Gender (F/M) | 13/16 | 6/8 | 4/5 |
| SRT total score | 49.1 ± 8.5 | 46.1 ± 9.7 | 39.7 ± 13.2 |
| Mattis Dementia Rating Scale | 140.4 ± 2.1 | 138.8 ± 2.5 | — |
| Mini-Mental State Exam | — | — | 27.6 ± 1.7 |

Exemplary Visual Processing Task (EEG)

Subjects were assessed using an optimized visual paradigm that uses interleaved stimulus-onset, motion-onset, and ssVEP to evaluate multiple aspects of early visual processing in parallel. Responses were obtained to both low- and high-SF stimuli. LSF and motion stimuli can bias processing toward the magnocellular visual system, whereas HSF stimuli can bias activity toward the parvocellular visual system. Both time-domain and neuro-oscillatory (e.g., "time-frequency") analyses were used to provide convergent assessment of underlying mechanisms.

As shown in the diagram of FIG. 1A, each trial began with the onset of one of three types of patterns (e.g., vertical gratings): (i) LSF (e.g., 0.8 cycles per degree, cpd) at high (e.g., 75%) luminance contrast (e.g., $LSF_{HC}$); (ii) LSF at low (e.g., 8%) contrast, (e.g., LSF); or (iii) HSF (e.g., 5 cpd) at high (e.g., 75%) contrast (e.g., $HSF_{HC}$). As shown in the timing diagram of FIG. 1B, motion-onset 110 began 400 ms after stimulus-onset 105 and lasted for approximately 200 ms. The grating drifted rightward for 200 ms (e.g., to motion offset 115) and remained static for 800 ms. Following, the stimulus counterphase reversals 120 began at about 1400 ms (e.g., 10 Hz) for 3000 ms (e.g., ending at 125) yielding a ssVEP response at about 4900 ms. A fixation of the results 130 occurred after the ending of the counterphase reversal 125. Throughout the trial, subjects maintained fixation on a central cross-hair and pressed a button when it dimmed slightly.

The ongoing EEG was recorded from 64 electrodes (e.g., sampling rate 512 Hz), filtered offline (e.g., 0.1-100 Hz) and epoched from −1000-3000 ms surrounding the onset and motion-onset of each stimulus prior to averaging across trials. Averaged ERPs were digitally low-pass filtered. Epochs with excessive eye movements, noise produced by excessive muscle activity, external electrical sources, or those preceded/followed by a response, were excluded. Mean amplitude measurements for the major ERP components were taken relative to the amplitude of the 100 ms baseline preceding stimulus/motion onset. All channels were referenced to the average of all channels.

ssVEP's were analyzed from 500-2500 ms following onset of the first reversal. The total power spectrum of the ssVEP waveform was derived from the single-trial epochs via fast-Fourier transform ("FFT") using a hamming filter and averaged separately for each stimulus type. Mean FFT power at 10 Hz was computed for each electrode/stimulus.

For ERSP (e.g., time-frequency) analyses, the single-trial EEG signal on each channel was convolved with 3-cycle Morlet wavelets at each time point from −1000 ms to 3000 ms following stimulus onset. (See, e.g., References 19 and 25). Phase locking, measured as inter-trial coherence ("ITC") at each frequency across trials, was calculated by normalizing the complex wavelet decomposition on every trial by its absolute value and averaging this quantity over all trials. (See, e.g., Reference 19 and 24). Single-trial power was derived by subtracting the mean spectral amplitude from the −250 to −50 ms pre-stimulus interval (e.g., corrected separately for each frequency band in each individual subject), from the averaged spectral amplitude at each time point and frequency.

Exemplary Amyloid Scans

18F-Florbetaben was donated by Piramal (e.g., Piramal Pharma Inc.). PET scans were performed using a Siemens MCT PET/CT scanner in dynamic, three-dimensional acquisition mode. Dynamic acquisition frames were obtained over about 20 minutes (e.g., 4×5 min frames) beginning at about 50 min following the bolus injection of 10 mCi of 18F-Florbetaben. An accompanying structural CT scan (e.g., in-plane resolution=0.58×0.58 mm, slice thickness=3 mm, FOV=300×300 mm, number of slice=75) was acquired and used for attenuation correction. PET data were reconstructed using a TrueX (e.g., HD-PET) procedure. Images were smoothed with a 2 mm Gaussian kernel with scatter correction.

Dynamic PET frames (e.g., 4 scans) were aligned to the first frame using rigid-body registration and a static PET image was obtained by averaging the four registered frames. The static PET and CT images were coregistered and merged to generate a composite image in the PET static space. Each individual's structural T1 image in FreeSurfer space was also registered to the participant's merged image to transfer region(s) of interest ("ROIs") and the cerebellar gray matter from FreeSurfer space to static PET image space. These ROIs in static PET space were used to extract the regional PET data.

The standardized uptake value ratio ("SUVR") was calculated at selected regions. The standardized uptake value ("SUV") was then normalized to gray matter cerebellum to derive the SUVR. Individuals were characterized as amyloid positive vs. negative based upon clinical evaluation, independent of specific SUVR values. The SUVR value was missing for one individual.

Exemplary Functional Connectivity

For this, resting-state functional magnetic resonance imaging (fMRI") of either 5 or 9.5 minutes was pre-existing for all 40 participants and was processed with a removal of motion artefacts (see, e.g., Reference 31), resulting in subject-level connectivity matrices for 264 functional ROIs. (See, e.g., Reference 32). Evaluation of subnetworks was performed using an exemplary parcellation procedure. (See, e.g., Reference 43).

Exemplary Statistics

For all measures, between-group analyses were conducted using repeated measures multivariate analysis of variance ("rmMANOVA") with follow-up Dunnett-tests of each experimental group (e.g., amyloid-positive, MCI) vs. amyloid-negative healthy elders. Effect-sizes were calculated based upon group differences divided by pooled standard deviation ("std dev") and interpreted according to various conventions. (See, e.g., Reference 7). The relationship between measures was assessed using Pearson (r) or multivariate partial ($r_p$) correlations as appropriate. All statistics were two-tailed with preset a level for significance of $p<0.05$.

Exemplary Results

Subjects included 43 healthy elders (e.g., 29 amyloid-negative/14 amyloid-positive) and 9 subjects with documented MCI. Responses were obtained to both stimulus- and motion-onset activity. Stimulus-onset activity can be indexed in the time domain by the visual P1 potential, illustrated in the chart shown in FIG. 2A for the 3 diagnostic groups (e.g., amyloid negative elders 205, amyloid positive elders 210 and those with MCI 215), and in the time-frequency domain by theta activity over posterior visual regions (see, e.g., exemplary time frequency images shown in FIG. 2B and head maps shown in 2C).

Motion-onset activity indexed in the time-domain by the N2m potential (see, e.g., exemplary chart shown in FIG. 2A) and in the time-frequency domain by delta-frequency (see, e.g., exemplary time frequency images shown in FIG. 2B), that can be largest over right MT (see, e.g., FIG. 2D). Primary analysis for both sets of measures consisted of an rmMANOVA with within-subject factor of stimulus type (e.g., $LSF_{LC}$, $LSF_{HC}$, and HSF) and between-subject factor of diagnostic group (e.g., amyloid-negative vs. amyloid-positive vs. MCI). Post-hoc Dunnett testing was used to compare both amyloid-positive healthy elders and MCI subjects to amyloid-negative controls.

Exemplary Stimulus Onset Activity

For stimulus onset-induced theta activity, there was a highly significant main effect of group (e.g., $F_{2,49}=9.30$, $p<0.0001$). Post-hoc testing showed highly significant reductions in theta response amplitude between both amyloid-positive (e.g., Dunnett $p<0.0001$, $d=1.20$) and MCI subjects (e.g., Dunnett $p=0.02$, $d=0.99$) relative to amyloid-negative healthy elders.

The main effect of stimulus-type was also significant (e.g., $F_{2,48}=7.59$, $p=0.001$), reflecting larger responses to high- vs.

low-contrast stimuli across groups irrespective of SF (e.g., $F_{1,49}=11.3, p=0.001$) (e.g., Table 1). Finally, the group X condition interaction showed a borderline significance level (e.g., $F_{4,96}=2.47, p=0.05$), reflecting larger differences in the high-vs. low-contrast conditions (e.g., $F_{1,49}=4.61, p=0.015$).

Exemplary Motion Onset ERSP

For motion onset-induced delta activity, there was a highly significant main effect of group. An rmMANOVA across all conditions showed a significant main effect of group (e.g., $F_{2,49}=11.8$, p<0.001), with no significant main effects of stimulus type (e.g., $F_{1,49}=1.0$, p=0.39) or stimulus type X group (e.g., $F_{2,49}=0.44$, p=0.78) interaction. Post-hoc testing showed a significant reduction in delta activity in amyloid-positive relative to amyloid-negative elders (e.g., Dunnett p<0.0001, d=1.2). By contrast, no significant difference was observed between MCI patients and amyloid-negative elders (e.g., Dunnett p=0.27, d=0.39).

Exemplary Onset/Motion ERSP vs. Amyloid Load

In order to determine relative sensitivity of stimulus-onset (e.g., theta)—and motion-onset (e.g., delta) activity to amyloid load, a multiple regression analysis of the two measures was conducted relative to amyloid SUVR. Both stimulus-onset (e.g., r=−0.45, p=0.003, chart shown in FIG. 3A) and motion-onset (e.g., r=−0.54, p<0.001, chart shown in FIG. 3B) showed significant independent correlations with amyloid-negative 305 and amyloid-positive 310.

In the multiple regression analysis, significant partial correlations were observed for both stimulus- (e.g., $r_p=-0.39$, p=0.012) and motion- (e.g., $r_p=-0.50$, p=0.001) onset activities and amyloid density, with the combined measure accounting for approximately 40% of the variance in SUVR (e.g., $R^2=0.40$, p<0.0001).

Based upon the regression, a composite biomarker score was calculated incorporating both stimulus-onset and motion-onset measures. Correlation between the composite biomarker and global amyloid SUVR was highly significant across individuals (e.g., r=−0.64, p<0.0001, chart shown in FIG. 3C). Moreover, a cutoff value of 0.1 on the combined measure correctly identified 90% of amyloid-positive individuals, but only 21% of amyloid-negative individuals (e.g., LR $\chi^2=20.4$, p<0.0001), yielding a sensitivity of 90% and a specificity of 86% for detecting amyloid-negative individuals. Application of these values to a general population with an a priori prevalence of amyloid of 20% (see, e.g., Reference 13), would yield positive and negative predictive values of 62% and 97%, respectively.

Exemplary Steady-State VEP ssVEP primarily reflects synchrony between visual regions and subcortical nuclei (e.g. lateral geniculate nucleus ("LGN"), pulvinar nucleus). Amplitude of the ssVEP was significantly different across groups (e.g., $F_{2,43}=3.94$, p=0.027). However, in post-hoc testing, no significant deficit was observed for amyloid-negative vs. amyloid-positive patients (e.g., Dunnett p=0.5), whereas a significant difference was observed between amyloid-negative and MCI subjects (e.g., p=0.015). The difference in visual ERSP between amyloid-positive and amyloid-negative subjects remained strongly significant (e.g., $F_{1,35}=21.7$, p<0.0001) even following covariation for ssVEP.

Exemplary Regional Correlations

Figure 4B:
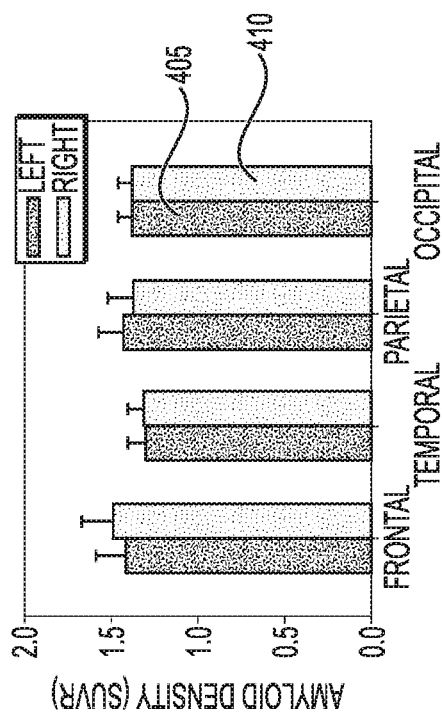
FIG. 4B is a chart illustrating an exemplary amyloid density by brain region according to an exemplary embodiment of the present disclosure.
Figure 4D:
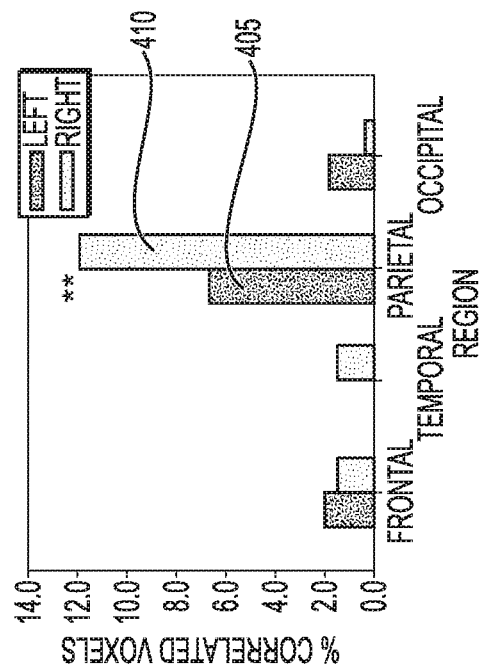
FIG. 4D is an exemplary image illustrating % correlated voxels by brain region according to an exemplary embodiment of the present disclosure.
Figure 4A:
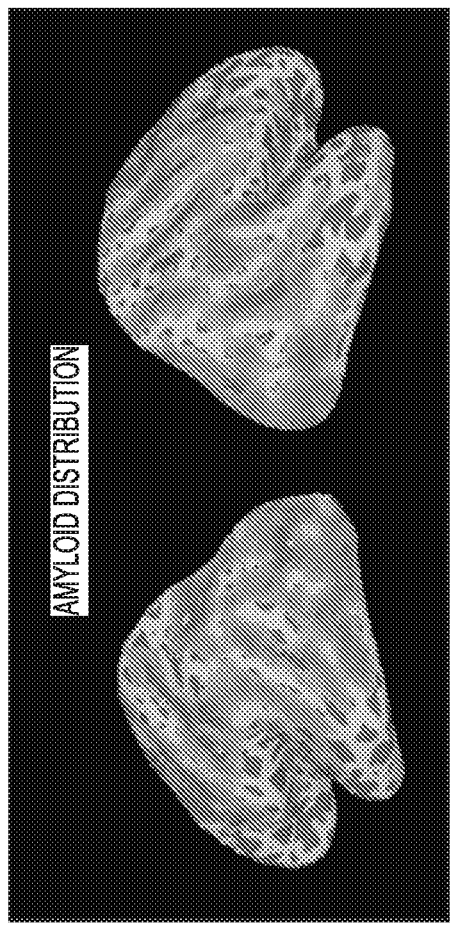
FIG. 4A is an exemplary image illustrating a distribution of amyloid across the cortical surface across healthy elders according to an exemplary embodiment of the present disclosure.
Figure 4C:
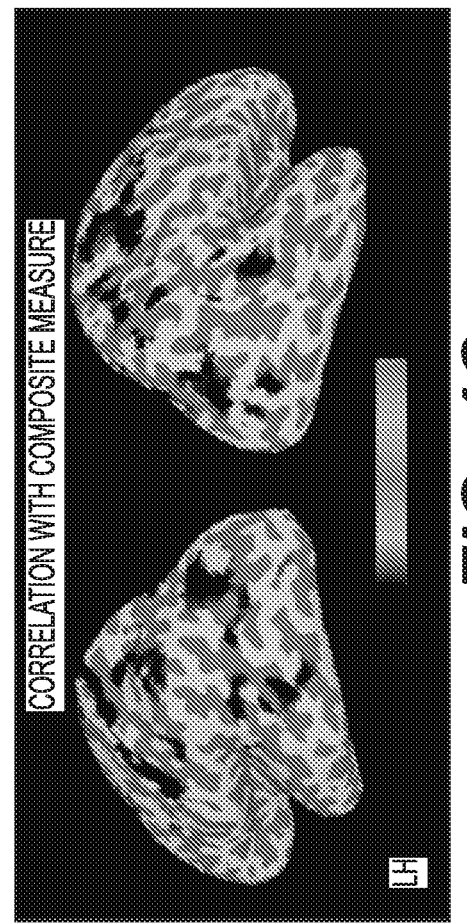
FIG. 4C is a chart illustrating an exemplary voxelwise correlation between amyloid density and composite (combined theta/delta) visual event-related spectral perturbation score according to an exemplary embodiment of the present disclosure.

Regional Amyloid Vs. Visual ERSP:
To examine regional correlations of amyloid with visual ERSP generation, a voxelwise analysis was performed using the composite visual ERSP amplitude relative to patterns of amyloid deposition. Amyloid distribution was observed throughout the brain in healthy elders, with highest concentrations in frontal cortex, but significant levels in parietal and occipital cortex as well (see, e.g., exemplary image shown in FIG. 4A and the corresponding chart shown in FIG. 4B). By contrast, voxels showing significant correlation to impaired visual ERSP generation were highly concentrated in parietal cortex (e.g., $\chi^2_3=12$, p=0.007) (see, e.g., exemplary image shown in FIG. 4C and left 405 and right 410 shown in the corresponding chart shown in FIG. 4D), suggesting that impaired visual ERSP were highly sensitive to posterior cortical dysfunction.

Exemplary Functional Connectivity:
Regional analyses were also performed using fcMRI to evaluate functional connectivity networks associated with reduced visual ERSP generation. An initial analysis evaluated functional connectivity between VIS nodes and the rest of the brain across networks. Overall, 49 pairs of connections were identified that correlated with visual ERSP amplitude at p<0.01 (e.g., 31 pos/18 neg) (e.g., Supplemental Table 1). Of these, the default mode network (e.g., DMN, n=26) was significantly over-represented relative to the other networks (e.g., $\chi^2=52.8$, df=5, p<0.0001), and accounted for >50% of total connections (e.g., exemplary positive correlations 505 and negative correlations 510 shown in FIG. 5A), suggesting preferential involvement in visual dysregulation.

Given known interaction of the DMN with the DAN in relation to visual processing (see, e.g., Reference 8), a second level analysis was evaluated across network connectivity related to impaired biomarker generation. Three simultaneous internetwork couplings emerged as significant: DMN to DAN (e.g., $r_p=0.35$, T=2.97, p=0.005), DAN to sensorimotor network ("SENS"), and VIS to ventral attention ("VAN") (e.g., $r_p=-0.28$, T=−1.78, p=0.08). The overall model was statistically significant (e.g., $F_{3,38}=3.81$, p=0.017) and accounted for 23% of the variance in visual ERSP across subjects (see, e.g., diagrams shown in FIG. 5B.)

In order to further parse these relationships, specific nodes within the DAN and DMN were queried. Consistent with results of the regional SUVR analysis, DAN-DMN connections that modulated visual ERSP generation were localized primarily to parietal nodes of the DAN (e.g., DAN-C, (see, e.g., Reference 43)) and involved primarily connections to anterior nodes of the DMN (e.g., DMN-A) (see, e.g., FIG. 5B). These connections were primarily positive, suggesting that increased connectivity correlated with more impaired visual ERSP generation. By contrast, impaired connectivity between nodes within DMN (see, e.g., FIG. 5B) correlated positively with impaired visual ERSP generation, suggesting that greater internal coherence of the DMN supported more effective visual processing.

Exemplary Control Analyses

Neurocognitive test measures for the groups are shown in Table 1. As expected, there was an overall difference in cognitive performance as measured by the SRT across groups (e.g., $F_{2,49}=3.27$, p=0.046), with MCI patients showing significant impairments relative to amyloid-negative healthy elders (e.g., Dunnett p=0.028, d=0.84). By contrast, amyloid-negative and amyloid-positive elders showed similar performance (e.g., Dunnett p=0.56, d=0.33). Similarly, no significant correlations were observed between visual ERSP and SRT (e.g., r=−0.04, df=50, p=0.8) or Mattis dementia rating scale (r=−0.09, df=41, p=0.6) score.

The correlations between visual ERSP and amyloid SUVR also remained significant even following covariation for age and neuropsychological performance (e.g., $r_p$=−0.62, df=39, p<0.0001). By contrast, no significant correlations between amyloid values and neuropsychological measures were observed (e.g., all p>0.2).

There were no significant differences in age or gender composition across groups (see, e.g., Table 1). No differences were observed by age or gender on any of the experimental measures.

Exemplary Discussion

Over recent years, deficits in visual ERSP have been extensively characterized in neuropsychiatric disorders such as schizophrenia, and have been shown to correlate significantly with impaired function on visually dependent tasks such as perceptual closure (see, e.g., References 9, 14, and 37), face processing (see, e.g., Reference 5) or reading. (See, e.g., References 33, 34, and 39). In the course of such studies, methods for application of visual ERSP technology to the study of neuropsychiatric populations have significantly evolved, providing increased power for detection of disease-related alterations in visual function. (See, e.g., References 15-18, and 21). An efficient ERSP paradigm was utilized to elicit both stimulus- and motion-onset ERSP and time-frequency analysis approaches to evaluate potential alterations of visual ERSP related to amyloid load in healthy aging.

As predicted, visual neurophysiological measures, including stimulus-onset theta activity (d) showed high correlation with amyloid load, and significantly differentiated amyloid-positive from amyloid-negative individuals with large effect size (e.g., d=1.03 sd units). In addition, in voxelwise analyses, deficits in visual ERSP correlated with regional amyloid deposition within visual regions, and with impaired functional connectivity within occipital cortex.

Although visual ERSP have previously been examined in individuals with established MCI or AD (see, e.g., References 35, 42, and 44), the exemplary system, method, and computer-accessible medium, can utilize visual ERSP deficits associated with amyloid levels in healthy elders, as well regional amyloid levels, to functional connectivity alterations within occipital visual areas.

To the extent that prior studies have been conducted in neurodegenerative disorders, deficits have been observed primarily in later stages of visual ERSP generation, such as the higher-level processing within the dorsal visual stream, whereas earlier stages of processing can be intact. (See, e.g., References 40 and 42). A limitation of prior studies, however, can be that they have used relatively non-physiological visual stimuli, such as flash or contrast-reversing checkerboard, and also have confined their analytic approach to time-domain measures (e.g. visual P1).

In the exemplary system, method, and computer-accessible medium, effect sizes were larger for frequency domain measures (e.g., theta, delta) vs. their time domain counterparts (e.g., P1, N2m) (see, e.g., FIG. 2). This difference can likely be due to the greater ability of the frequency domain analyses to resolve stimulus-induced activity vs. background EEG that can occur primarily in alpha (e.g., 8-12 Hz) frequency over posterior brain regions. Restricting analyses to lower frequency bands can thus improve the signal-to-noise of the measures and thus the power for resolving between group differences. Moreover, robust (e.g., r=−0.62, p<0.0001) correlations were observed between the frequency-domain visual ERSP measures and global amyloid SUVR values (see, e.g., FIGS. 3A-3C), supporting use of these measures as clinical surrogates for more invasive (e.g. lumbar puncture, PET) approaches.

In regional analyses designed to assess mechanisms underlying the amyloid to visual ERSP link, amyloid deposition within the parietal lobe appeared to be the primary driver of reduced ERSP amplitude. This relationship was observed both in correlations of visual ERSP to regional amyloid SUVR, where correlations with parietal cortex were disproportionately observed (see, e.g., FIG. 4D).

In general, these findings can be consistent with prior literature showing amyloid-induced impairments in DMN function correlating with impaired neurocognitive function in aging (see, e.g., Reference 38), as well as prior findings of alteration of within- and across-network connectivity in aging. (See, e.g., Reference 38). This illustrated that poorer visual performance was associated with increased connectivity between DMN and DAN, but reduced connectivity within the DMN can also be consistent with concepts that de-differentiation across networks can contribute significantly to cognitive impairment in aging. (See, e.g., Reference 38). Interpretation of these findings can be limited by the relatively short duration of the fcMRI scans obtained, as well as the lack of fcMRI acquisition during stimulation. Nevertheless, these findings suggest that as opposed to in schizophrenia, amyloid-related visual ERSP deficits in healthy aging can be driven primarily top-down, and can involve parietal amyloid deposition disrupting connectivity to parietal nodes of DMN and DAN networks.

In addition to showing the potential utility of visual ERSP as a surrogate biomarker for amyloid burden, the exemplary system, method, and computer-accessible medium according to the exemplary embodiment of the present disclosure, can examine the utilization of deficits in early visual processing as a cause of social disability in both amyloid-positive healthy elders and MCI individuals. In schizophrenia, deficits in early visual processing contribute significantly to impaired face processing and social cognition, using tests such as the Penn face emotion recognition test, or The Awareness of Social Inference Test ("TASIT"). (See, e.g., References 5, 10, and 18).

While similar tests have not been extensively reviewed in studies of healthy aging, one recent study showed significant declines in social cognitive function during healthy aging (see, e.g., Reference 20), similar to what has been previously observed in schizophrenia. (See, e.g., Reference 18). Moreover, deficits were unassociated with more general cognitive impairments. Future studies incorporating both visual and social cognitive measures can be needed to evaluate potential contributions of early visual dysfunction to social cognitive impairments in healthy aging, similar to what can be observed in schizophrenia.

The exemplary findings with regard to the very large effect-size (e.g., d=1.8) differences in visual ERSP measures also contrast sharply with the much smaller effect-size differences observed with neuropsychological performance assessed with such measures as the Mattis rating scale or the Bushke selective reminding task (e.g., d=0.3). The magnitude of difference that was observed can also be consistent with the magnitude of difference observed in larger meta-analyses. As confirmed in larger groups, the visual ERSP measures reported here can be significantly superior to more typically used neuropsychological assessments for assessing brain dysfunction associated with early stage of neurodegenerative disease.

Although amyloid deposition can be known to play a critical role in the preclinical phase of AD, non-invasive biomarkers of amyloid status remain limited. The exemplary system, method and computer-accessible medium, according to an exemplary embodiment of the present disclosure, show that optimized visual ERSP approaches can be sensitive to amyloid deposition even in otherwise healthy elderly individuals, and can reflect primarily top-down dysregulation of early visual regions. Such measures have high test-retest reliability and can be followed longitudinally if needed. Further studies to evaluate the utility of these biomarkers in early detection, intervention and longitudinal follow-up studies can be performed.

Exemplary Impaired Motion Processing in Schizophrenia

Sz is a complex mental disorder associated with prominent cognitive impairment (see, e.g., Reference 48) and poor long-term functional and social outcomes. (See, e.g., Reference 49). While deficits have been studied extensively in regard to higher-level cognitive processes (see, e.g., Reference 50), low-level sensory processing impairments have also been identified. (See, e.g., References 51 and 52). These low-level deficits cause disability in and of themselves and contribute to disturbances in higher-order perceptual processes involving both the visual and auditory systems (see, e.g., References 51 and 52), representing, critical components of the generalized cognitive impairment associated with schizophrenia. (See, e.g., Reference 53).

The primate visual system consists of two main afferent pathways that project from retina through the thalamic LGN to cortex. The magnocellular system can be specialized for LSF, low contrast information and projects preferentially to the dorsal stream (e.g., "vision for action") of visual cortical areas. By contrast, the parvocellular system can be specialized for processing HSF, high contrast information and projects preferentially to the ventral stream (e.g., "vision for identification"). In Sz, deficits can be most pronounced for LSF and low contrast stimuli, suggestive of differential impairment of the magnocellular visual pathway. (See, e.g., Reference 53).

Neurophysiological (e.g., event-related potential, ERP) and fMRI investigations have revealed highly significant deficits in cortical activation in patients with Sz relative to healthy controls in their responses to the onset of static (e.g., non-moving) visual stimuli that can be magnocellular-biased (e.g., LSF/low contrast). (See, e.g., Reference 53). For example, the amplitude of the sensory-evoked P1 component of the visual ERP can be differentially reduced in Sz patients in response to low-, as compared to high-contrast stimuli, as well as to LSF vs. HSF stimuli. (See, e.g., References 54-56). Further, source localization studies of the P1 have identified its neural generators in or near the extrastriate visual areas of the MOG (see, e.g., References 57-59), a region known to receive substantial magnocellular input. Similarly, fMRI studies have documented reduced activation of both striate and extrastriate visual areas in response to LSF/low-contrast stimuli, which was correlated with patients' impaired contrast sensitivity for LSF stimuli. (See, e.g., Reference 60).

In addition to deficits in processing static visual stimuli, deficits in motion perception have also been extensively documented in Sz (see, e.g., Reference 61), and have shown to underlie impairments in functions such as smooth pursuit eye tracking. (See, e.g., References 62 and 63). In humans, motion perception depends largely upon neural activity in a cortical region termed the middle temporal area (e.g., MT+, also known as V5). (See, e.g., References 64-66). Area MT+ can be dominated by input from the magnocellular pathway (see, e.g., References 66-68), though evidence exists for a robust disynaptic input from parvocellular layers of the LGN as well. (See, e.g., Reference 69). Abnormal activation of MT+ has been reported in Sz patients (see, e.g., References 70 and 71), and both "bottom up" deficits in input to MT+(see, e.g., References 70 and 71) and local dysfunction within MT+ itself (see, e.g., References 62 and 63) have been proposed to account for these impairments.

Electrophysiologically, moving stimuli can elicit a surface-negative potential in the scalp-recorded ERP—the N2m component (see, e.g., References 74 and 75), putatively generated within area MT+. (See, e.g., References 75 and 76). Consistent with magnocellular mediation, the N2m can saturate at low levels of contrast and can be larger in amplitude to the motion of LSF stimuli. (See, e.g., References 74, 75, 78, and 79). The integrity of the N2m has not been previously studied in Sz. Here, behavioral, electrophysiological and fMRI measures were used to investigate the timing and neural substrates of motion processing deficits in Sz in relation to cortical and subcortical sensory-processing deficits associated with impaired magnocellular pathway dysfunction. As with static stimulus onsets, motion processing deficits can be greatest for magnocellular-biased stimuli. Furthermore, impaired N2m generation can reduce MT+ activation and behavioral measures of impaired motion perception would be highly intercorrelated, demonstrating specific contributions of magnocellular dysfunction to the pathophysiology of motion processing abnormalities in schizophrenia.

The exemplary system, method, and computer-accessible medium, according to an exemplary embodiment of the present disclosure, can include a paradigm that quickly can provide electrophysiological indices of sensory and motion processing. (See, e.g., FIGS. 6A-6C). This paradigm assesses components of the visual ERP elicited by the onset/appearance of a vertical grating as well as the subsequent motion-onset ERP elicited by the rightward drift of the same stimulus. To reduce habituation of the motion ERP, successive motion stimuli were separated by 5 seconds. Following each motion ssVEPs were recorded in response to counterphase reversals of the grating stimulus. The ssVEP can be the phase-locked oscillatory ERP elicited by a visual stimulus presented at a regularly repeating rate (e.g., flickering or phase reversing), which closely follows the stimulation frequency of the eliciting stimulus. (See, e.g., Reference 80).

Numerous studies have reported ssVEP deficits in Sz, in particular in the alpha (e.g., 8-12 Hz) frequency range. (See, e.g., References 54, 81-86). While some studies have reported greater ssVEP impairments using magnocellular-biased stimuli (see, e.g., References 54 and 71), deficits have also been obtained with pulsed photic stimuli. (See, e.g., References 83 and 87). In Sz, altered ssVEP responses in the alpha range have been attributed to abnormalities in thalamocortical circuits, particularly those involving the thalamic pulvinar nucleus. (See, e.g., Reference 88). The pulvinar can be involved in the generation of alpha rhythms in primates (see, e.g., Reference 89) and can play an important role in the generation of scalp-recorded alpha oscillations in humans. (See, e.g., References 90 and 91). Thus, subcortical fMRI correlation of impaired ssVEPs in Sz examined special emphasis on potential thalamic contributions.

Although abnormalities in gamma band (e.g., 30-200 Hz) EEG oscillations can be well established in Sz (see, e.g., Reference 92), in recent years there has been increasing focus on impairments in lower-frequency oscillations in the theta (e.g., 4-7 Hz) and delta (e.g., 1-3 Hz) bands. (See, e.g., Reference 93). In healthy volunteers, the P1 potential elicited by stimulus onset has a waveform that can consist primarily of evoked theta activity. (See, e.g., Reference 94). By contrast, the spectral signature of the N2m potential has yet to be established, even in controls. Thus, along with traditional ERP (e.g., time-domain) analyses, the exemplary system, method, and computer-accessible medium, according to an exemplary embodiment of the present disclosure, was used to evaluate the utility of time-frequency analyses for revealing sensory and motion processing impairments in Sz.

Exemplary Schizophrenia Methods and Materials

Exemplary Schizophrenia Subjects

Participants included 38 patients (e.g., 5 female) meeting DSM-IV criteria for Sz assessed by the Structured Clinical Interview for DSM-IV ("SCID") (see, e.g., Reference 95) and 23 HC volunteers (e.g., 7 female) with no history of SCID-defined axis I psychiatric disorders. Electrophysiological and behavioral data were acquired from all participants. A subset of 21 Sz patients and 16 HC additionally took part in the fMRI study. In patients, psychiatric symptoms were evaluated using the Positive and Negative Syndrome Scale ("PANSS"). (See, e.g., Reference 96). Neurocognitive ability was assessed using the processing speed index ("PSI") of the WAIS-III.

All patients were recruited from outpatient and chronic inpatient clinics in the New York City area and were on a stable dose of antipsychotics at time of testing. Subjects were excluded if they had any neurological or ophthalmologic disorders or if they met criteria for alcohol/substance dependence within the last 6 months or alcohol/substance abuse within the last month.

All participants had at least 20/22 (1.02) corrected visual acuity or better on the Logarithmic Visual Acuity Chart. When compared to HC subjects, Sz patients did not differ significantly in age but had significantly fewer years of formal education as well as reduced Hollingshead socioeconomic status ("SES") scores. Parental SES and Quick IQ scores (see, e.g., Reference 97) did not differ between groups, suggesting similar premorbid potential in Sz subjects. (See, e.g., Table 2, below).

TABLE 2

Subject demographics and characteristics.

| | Sz | HC | Group difference, p |
|---|---|---|---|
| Age | 41.2 (10.4) | 37.3 (8.4) | 0.156 |
| Quick IQ | 96.0 (11.6) | 100.0 (7.9) | 0.129 |
| Years of Education | 11.1 (2.0) | 14.5 (1.8) | <.001 |
| Participant SES | 21.9 (6.3) | 41.4 (10.4) | <.001 |
| Parental SES | 36.0 (11.6) | 43.7 (15.4) | 0.067 |
| Illness Duration (yrs) | 17.2 (9.3) | — | — |
| PSI | 98.7 (14.1) | 80.1 (12.2) | <.001 |
| PANSS (pos.) | 20.7 (5.1) | — | — |
| PANSS (neg.) | 19.6 (4.5) | — | — |

Standard deviations are in parentheses. SES, socioeconomic status; PANSS, Positive and Negative Scale for Schizophrenia; PSI, Processing speed index, CPZ, chlorpromazine equivalents. (See, e.g, Reference 67).

Exemplary Schizophrenia Coherent Motion Discrimination Task (Behavior)

Thresholds for coherent motion detection (e.g., at 82% correct) were identified using a two-alternative forced-choice task. Random-dot kinematograms consisted of a square patch (e.g., 7.5°×7.5° visual angle) containing 120 randomly arranged gray dots (e.g., 0.5°×0.5°, 65% contrast) on a darker (e.g., 40% contrast) background. On each trial, a proportion of dots corresponding to the motion coherence for that trial moved coherently in the target direction (e.g., left/right) for 1000 ms. The remaining dots moved either to the left or right with equal probability. After 1000 ms, the dots disappeared and two arrows pointing left and right were displayed, cueing participants to indicate the direction of coherent motion in the preceding interval. There was no time limit for responding. After each response an inter-trial interval of 1000 ms, in which only a fixation cross was displayed, preceded the onset of the subsequent trial. The motion coherence for each trial was determined by the QUEST procedure, which computes a Bayesian estimate based on all previous trials and a pre-defined prior to determine the optimal (e.g., most informative) coherence level for threshold estimation for the following trial. Coherence thresholds were based on 100 trials. (See, e.g., exemplary diagram shown in FIG. 6A).

Exemplary Schizophrenia Electrophysiology

Exemplary Stimuli And Task

Subjects sat in an electrically shielded, sound-attenuated, dimly lit, chamber and viewed stimuli on an LCD monitor situated 100 cm in front of them. Stimuli were grayscale vertical sinusoidal gratings (e.g., 2°×2° visual angle) composed of either (i) LSF's (e.g., 0.8 cpd) at high (e.g., 75%) luminance contrast (ii) LSF's at low (e.g., 8%) luminance contrast; or (iii) HSF's (e.g., 5 cpd) at high luminance contrast. The lower edge of all stimuli was positioned 1° of visual angle above a central fixation cross measuring 0.4°× 0.4°. All stimuli were presented on an isoluminant gray background. Presentation software (e.g., http://www.neurobs.com/) was used for stimulus delivery.

Each trial lasted 4900 ms, and began with a 500 ms presentation of the central fixation cross. Next, one of the three types of gratings was presented (e.g., order was randomized) and remained static for 400 ms. The grating then drifted rightward at a velocity of 14°/s for 200 ms. After an 800 ms delay, during which the grating was static, the grating counterphase reversed at a rate of 10 Hz for 3000 ms, thereby generating a ssVEP. During the entire trial, the subjects' task was simply to fixate the central cross and respond with a button press when it dimmed slightly (e.g., every 3-12 s). Each subject took part in 420 trials (e.g., 140 of each stimulus type; 34.2 min total recording time). A brief break was given after every 60 trials. (See, e.g., exemplary diagram shown in FIG. 6B).

Exemplary Schizophrenia Recordings and Data Analysis

The ongoing EEG was recorded using a custom Waveguard cap (e.g., Advanced Neuro Technology) containing 64 equally-spaced electrodes covering the whole head from above the eyebrows to below the inion. (See, e.g., Reference 98). The recording reference site was Cz. Because of this particular distribution of electrodes, only some electrode positions completely matched the International 10-20/10-10 System locations; in cases where they didn't match exactly the closest 10-20/10-10 location can be given. Impedances were kept below 5 kΩ throughout the experiment. The horizontal EEG was monitored with bipolar electrodes on the left and right outer canthi. Data were acquired at a sampling rate of 512 Hz and filtered offline using cutoffs of 0.1 and 100 Hz. Continuous EEG data was epoched from −1000 to +3000 ms surrounding the onset of each stimulus type. Epochs with amplitudes exceeding ±100uV at any electrode, eye blinks, excessive eye movements, or those preceded within 800 ms or followed within 200 ms of a motor response were excluded from the average. On average, 9.2% of all trials from HC and 11.8% from Sz patients were excluded. Artifact-free data were re-referenced to the average reference.

ERPs were obtained by time-locking to the onset and motion-onset of each stimulus and averaging across trials. The averaged ERPs were digitally low-pass filtered with a Gaussian finite impulse function (e.g., 3 dB attenuation at 46 Hz) to remove high-frequency noise produced by muscle activity and external electrical sources.

Mean amplitude measurements for the major ERP components elicited by the onset and motion-onset of each stimulus were taken within specified time windows encompassing the peak of each component. In all cases, a single measurement was taken across each component window relative to the mean amplitude of the 100 ms baseline preceding stimulus-onset/motion-onset. The mean amplitude of the P1 component, elicited by stimulus onset, was tested in the latency window 120-150 ms across 8 lateral occipital electrode sites (e.g., 4 per hemisphere, (e.g., O1/O2, O1i/O2i, P3/P4, TO1/TO2). The mean amplitude of the ERP elicited by motion-onset N2m was measured in the 280-320 ms time window following motion onset across the same lateral occipital scalp sites. Separate repeated measures ANOVAs were performed for the P1 and N2m components with a between-group factor of Group (e.g., HC, Sz) and within-group factors of Stimulus (e.g., LSF high/low contrast, HSF) and Hemisphere (e.g., LH, RH).

Analysis of the ssVEP was performed on artifact-corrected epochs extending from 500 to 2500 ms following stimulus onset (e.g., the first 500 ms were excluded to avoid contamination by transient ERPs). For each subject, the total power spectrum of the ssVEP waveforms was derived via FFT (e.g., Hamming window) from the single trial epochs and averaged separately for each type of stimulus. Amplitudes were quantified as the absolute value of the complex Fourier coefficients. For each subject and stimulus, FFT power within a narrow band (e.g., about 9.8 Hz-10.2 Hz) surrounding the stimulation frequency of 10 Hz was averaged across 3 mid-occipital electrodes.

To analyze event-related changes in EEG/ERP power (e.g., evoked power), subjects' time-averaged ERPs elicited by the onset of each stimulus were convolved with 3-cycle Morlet wavelets computed over a 3-second window beginning 1000 ms before the initial onset of the grating stimulus. For each type of stimulus, power (e.g., calculated as the sum of the squares of the real and imaginary Morlet components) was extracted at each time point over 73 frequency scales from 0.73 to 53.5 Hz, incremented logarithmically. (See, e.g., Reference 99). The square roots of the power values were then averaged separately for each stimulus and across subjects in each group to yield the evoked power at each electrode. Statistical analyses were conducted over the same cluster of posterior electrode sites used to test the P1/N2m components.

All analyses of electrophysiological data were performed using MATLAB (e.g., Mathworks, Natick, MA) with the EEGLAB (see, e.g., Reference 100) and ERPLAB (see, e.g., Reference 101) toolboxes. For all measures, between-group analyses were conducted using repeated measures ANOVA with follow-up t-tests. The relationship between all measures was assessed using Pearson correlations. All statistics were two-tailed with preset α level for significance of $p<0.05$.

Exemplary Schizophrenia Functional MM

Exemplary Stimuli and Task

Motion-sensitive cortical areas were identified using stimuli and procedures similar to those in previous studies. (See, e.g., Reference 102). Stimuli included low-contrast (e.g., 12%) concentric rings presented at fixation and extending throughout a circular region measuring 15° in diameter. Stimuli were passively delivered in twenty-second epochs, alternating between stationary rings and rings expanding/contracting at a rate of 7°/sec. A fixation cross was continuously present at the center of the display and its luminance was slightly decreased every 4-10 seconds. Subjects were required to indicate detection of this dimming by making a manual response. (See, e.g., diagram shown in FIG. 6C).

Exemplary Schizophrenia Acquisition and Data Analysis

T2*-weighted echo-planar images ("EPIs") (e.g., TR=2 sec; TE=38 ms; flip angle=90; voxel size=4 mm$^3$; matrix size 64×64) were acquired on a Siemens Tim Trio 3T 80 cm bore head-only MRI system. Functional images were acquired on 32 contiguous slices in the axial plane. The Analysis of Functional NeuroImages software ("AFNI") (see, e.g., Reference 103) was used for all fMRI processing and statistical testing. The first four volumes of each run were discarded and successive images were co-registered to reduce motion artifacts, corrected for linear drift in time, and spatially smoothed with a 4 mm FWHM Gaussian filter. For anatomical localization high-resolution (e.g., 1 mm$^3$) structural images of the entire brain were acquired from each subject using an MPRAGE sequence (e.g., TR=11.6 ms; TE=4.9 ms, flip angle=8; effective inversion time=1.1 sec; matrix size 256×256). Functional images were registered to each participant's anatomy and transformed into standardized stereotaxic space. (See, e.g., Reference 104).

After pre-processing, individual subject data was analyzed with the general linear model ("GLM") procedures implemented in AFNI. Regressors representing the timing of the task (e.g., alternating blocks of moving/static stimuli) were convolved with a canonical hemodynamic response function and used in the analyses. Individual head-motion parameter estimates were also included in the GLM as nuisance covariates. A motion-selective cortex was identified by comparing neural activity elicited during blocks in which the stimuli expanded/contracted with blocks in which the stimuli were stationary. The resulting parameter estimates (e.g., beta) of motion selectivity were entered into a one-way ANOVA to define cortical and subcortical ROI for subsequent statistical testing. To ensure that ROI sizes were equivalent across participants, this group-wise analysis was based on data from all 37 fMRI participants. (See, e.g., Reference 105). Finally, within each ROI, group differences in cortical activation were evaluated by ANOVA with a between-group factor of Group (e.g., Sz, HC). Significance levels and minimum cluster sizes were calculated using Monte Carlo simulations (e.g., 3dClustSim). In all cases, only voxels with corrected p-values<0.01 survived the final threshold.

Exemplary Schizophrenia Results

Exemplary Schizophrenia Coherent Motion Discrimination

Figure 7C:
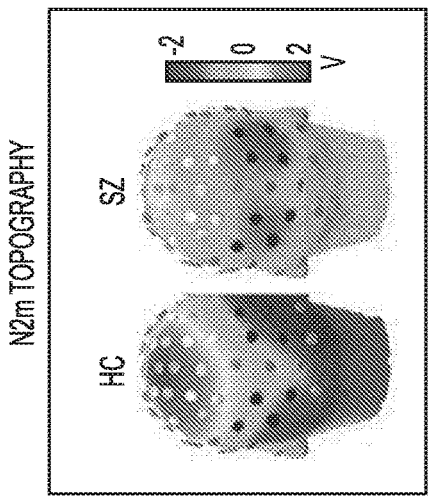
FIG. 7C is a set of exemplary images of the scalp topography of the N2m according to an exemplary embodiment of the present disclosure.
Figure 7B:
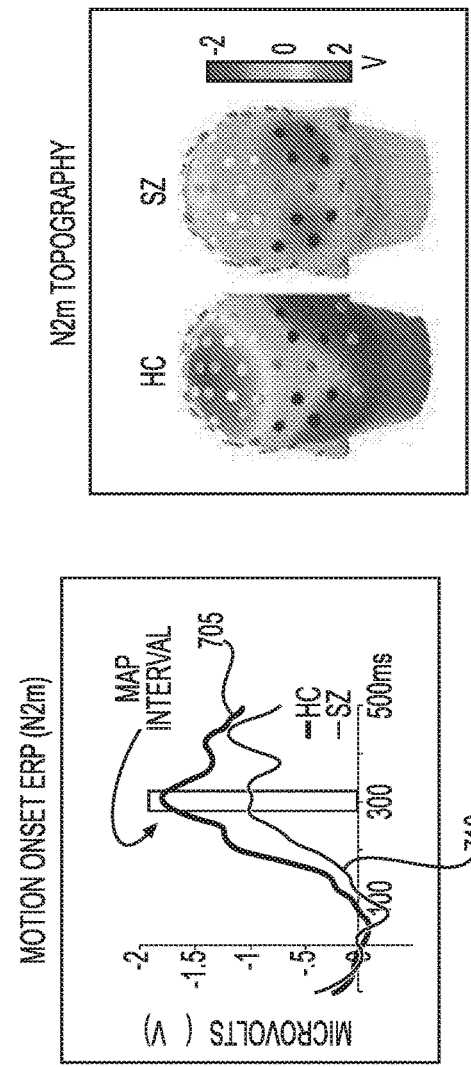
FIG. 7B is a chart illustrating an exemplary motion onset ERPs according to an exemplary embodiment of the present disclosure.
Figure 7A:
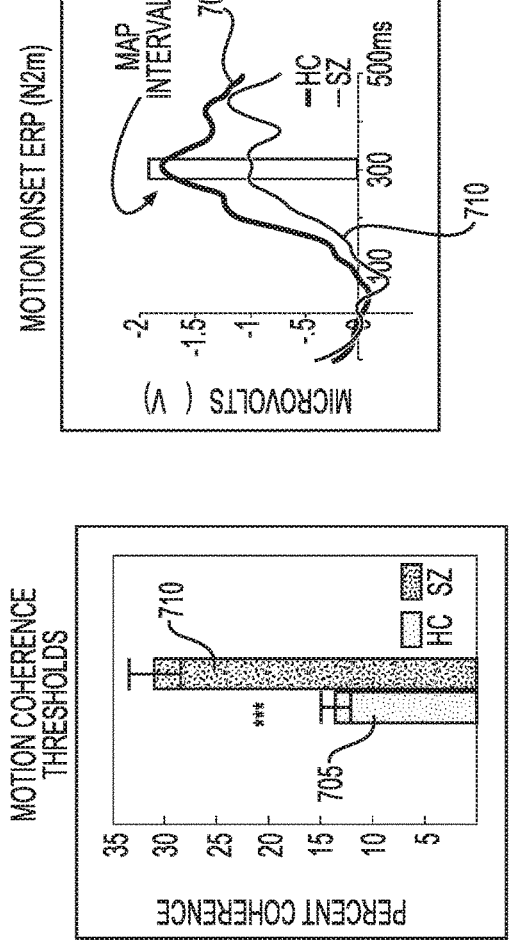
FIG. 7A is a chart illustrating exemplary motion coherence thresholds according to an exemplary embodiment of the present disclosure.

Coherent motion detection thresholds were significantly higher (e.g., indicating worse performance) in Sz subjects 505 compared to HC subjects 710 (e.g., $F(1,59)=27.33$, $p<0.001$). (See, e.g., exemplary chart shown in FIG. 7A). This difference remained significant after controlling for global cognitive impairment (e.g., as measured by the PSI) in an analysis of covariance (e.g., $F(1,59)=9.79$, $p=0.003$).

Exemplary Schizophrenia ERP's to Motion Onset

Figure 7E:
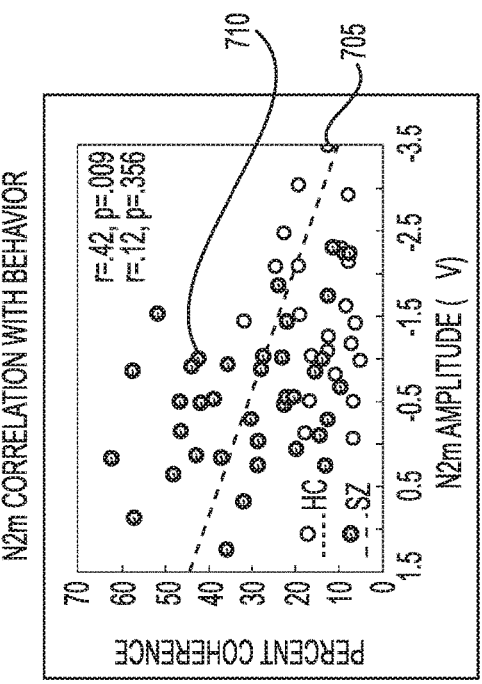
FIG. 7E is a chart illustrating an exemplary correlation between N2m amplitude and coherent motion perception according to an exemplary embodiment of the present disclosure.
Figure 7D:
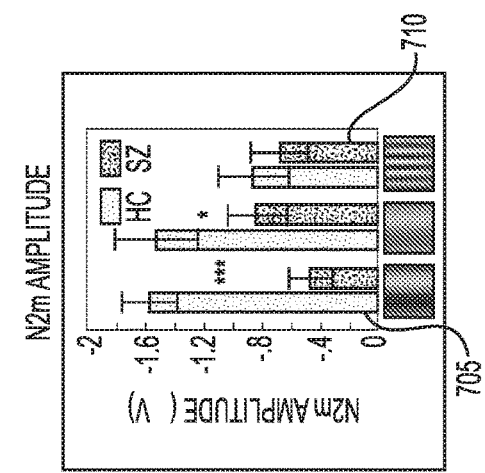
FIG. 7D is a chart illustrating an exemplary N2m amplitude for each stimulus type according to an exemplary embodiment of the present disclosure.

The onset of stimulus motion elicited a broad negative component starting, on average, about 160 ms post-motion onset over the ventro-lateral occipital scalp (e.g., N2m). (See, e.g., exemplary chart shown in FIG. 7B and exemplary topography map shown in FIG. 7C). Patients showed significantly reduced (e.g., less negative) N2m amplitudes, overall (e.g., $F(1,59)=7.73$, $p=0.007$). Differential deficits in N2m generation were reflected in the contrast between LSF and HSF stimuli which showed a highly significant Group X Stimulus interaction (e.g., $F(1,59)=18.63$, $p<0.001$. (See, e.g., exemplary chart shown in FIG. 7D). These N2m deficits in Sz patients were significant when the LSF conditions (e.g., high, low contrast) were tested independently (e.g., $F(2,58)=9.58$, $p<0.001$) but not so for HSF stimuli (e.g., $F(1,59)=2.36$, $p=0.629$). There were no significant main or interaction effects involving hemisphere (e.g., all $p>0.35$). For correlational analyses, data were averaged across hemispheres. Deficits in N2m generation correlated significantly with elevated coherent motion detection thresholds both across groups (e.g., $r=0.49$, $p<0.001$) and in Sz patients alone (e.g., $r=0.42$, $p=0.009$). (See, e.g., chart shown in FIG. 7E).

Exemplary Schizophrenia fMRI of Motion Processing

Figure 8A:
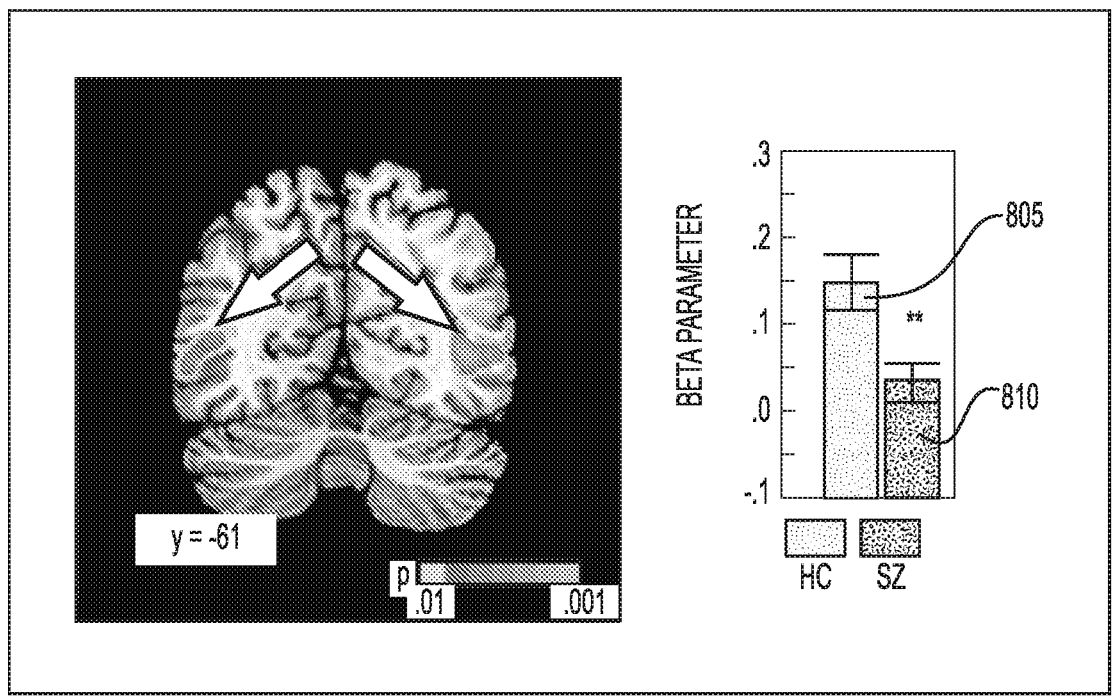
FIG. 8A is an exemplary image and chart illustrating activation in MT+ to moving stimuli according to an exemplary embodiment of the present disclosure.
Figure 8B:
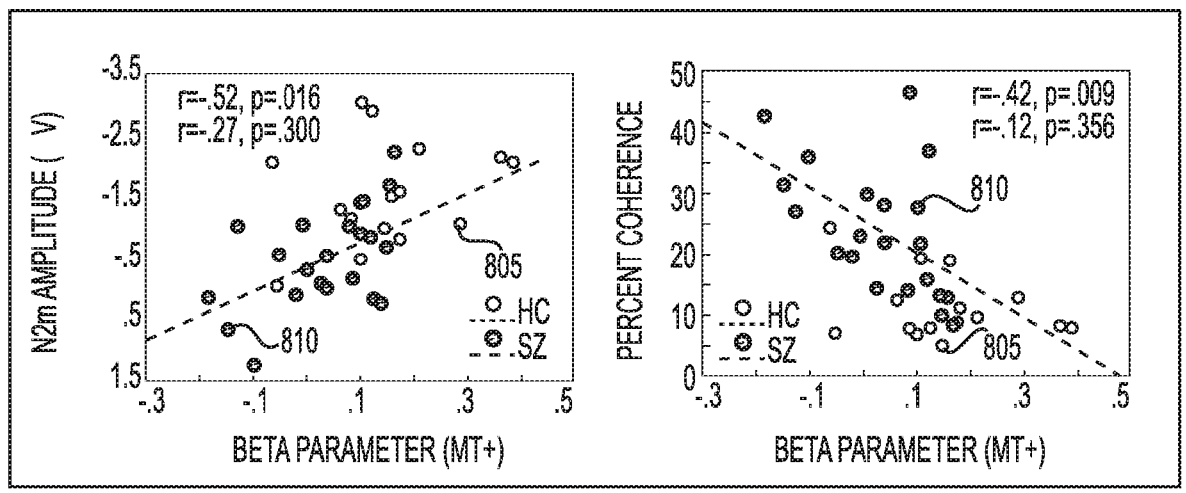
FIG. 8B is a set of exemplary charts illustrating the correlation between MT+ activation and N2m amplitude according to an exemplary embodiment of the present disclosure.

Across subjects, the largest foci of activation resulting from the contrast of moving versus static stimuli were in area MT+. (See, e.g., exemplary image shown in FIG. 8A). In particular, as shown in FIG. 8A, compared to HC subjects 805, Sz patients 810 showed significantly reduced activation in right hemisphere MT+(e.g., $F(1,35)=9.15$, $p=0.005$). Further, in patients with Sz ($r=-0.52$, $p=0.016$), and across all subjects (e.g., $r=-0.55$, $p<0.001$), reduced MT+ activation correlated significantly with lower N2m responses to LSF stimuli (e.g., mean of low and high contrast) as well as with poor coherent motion detection (e.g., Sz patients: $r=-0.53$, $p=0.014$; all subjects: $r=-0.57$, $p<0.001$). (See, e.g., exemplary charts shown in FIG. 8B).

Additional cortical and sub-cortical areas with significant motion-related enhancements across subjects included parts of striate cortex (e.g., calcarine fissure, Calc), the superior temporal gyms ("STG"), inferior parietal lobe ("IPL"), middle frontal gyms ("IFG"), MOG, fusiform gyms ("FG"), precuneus ("pCun") and the pulvinar nucleus of the thalamus ("Pulv"). (See, e.g., Table 3 below). Significant group differences were obtained in all of these ROIs, with Sz patients showing lower levels of activation compared to HC subjects. No significant correlations with N2m amplitude or motion detection thresholds were observed for any of these regions (e.g., $p>0.40$ for all).

TABLE 3

Brain areas activated across all subjects by the contrast of moving versus static stimuli

| Brain Region | x | y | z | Volume (mm³) | F(1, 35) | p |
|---|---|---|---|---|---|---|
| RH MT+ | 50 | −58 | 1 | 3225 | 9.15 | 0.005 |
| LH MT+ | −50 | −62 | −2 | 315 | 4.20 | 0.051 |
| LH Fusi. | −37 | −49 | −17 | 1795 | 11.20 | 0.002 |
| RH IPL | 50 | −37 | 43 | 585 | 13.60 | <.001 |
| RH Precun. | 27 | −71 | 23 | 315 | 4.90 | 0.035 |
| RH MFG | 34 | 30 | 33 | 860 | 9.50 | 0.004 |
| RH Calc. | 13 | −75 | 11 | 660 | 5.23 | 0.028 |
| LH MOG | −30 | −81 | 1 | 315 | 19.82 | <.001 |
| RH STG | 56 | −52 | 13 | 315 | 20.39 | <.001 |
| LH Pulvinar | −11 | −25 | 3 | 156 | 6.69 | 0.014 |

The Tailarach coordinates of the center of mass and the total volume of each ROI can be given, as can be F and p values for the statistical comparison of activation in Sz patients vs. HC subjects. (e.g., fusiform gyrus, Fusi.; inferior parietal lobe, IPL; precuneus, Precun.; middle frontal gyrus MFG; calcarine fissure, Calc.; middle occipital gyrus, MOG; superior temporal gyrus, STG).

Exemplary Schizophrenia ERP's to Stimulus Onset

In all subjects (e.g., HC 905 and SZ 910), the onset of all stimuli elicited a positive-going deflection (e.g., P1) over the occipital scalp beginning at approximately 100 ms post-stimulus onset with significantly larger amplitude over the right, compared to left, hemisphere (e.g., $F(1,59)=6.86$, $p=0.01$). (See, e.g., chart shown in FIG. 9A and topography map shown in 9B). As no further significant interactions involving Hemisphere were observed (e.g., Group x Hemisphere (e.g., $F(1,59)=1.51$, $p=0.223$); Stimulus x Hemisphere (e.g., $F(1,59)=1.89$, $p=0.156$), mean P1 amplitude over both hemispheres was used in subsequent correlational analyses.

Compared to HC patients 905, Sz patients 910 exhibited significantly reduced P1 amplitudes across all stimuli (e.g., $F(1,59)=8.03$, $p=0.006$) and for LSF stimuli when tested independently (e.g., $F(2,58)=7.32$, $p=0.001$). (See, e.g., exemplary chart shown in FIG. 9C). No significant deficit was observed for HSF stimuli (e.g., $F(1,59)=1.75$, $p=0.191$). The Group x stimulus interaction did not reach significance (e.g., $F(1,59)=1.68$ $p=0.190$). Reduced P1 amplitudes to LSF stimuli (e.g., averaged over high and low contrast levels) correlated across groups (e.g., $r=0.58$, $p<0.001$) and independently within both groups (e.g., Sz: $r=0.46$, $p=0.034$; HC: $r=0.55$, $p=0.027$) with significant deficits in motion-related activation in the ROI for MOG in Sz patients 910 compared to HC patients 910 (e.g., $F(1,35)=19.82$, $p<0.001$). (See, e.g., exemplary image and chart shown in FIG. 9D and exemplary chart shown in FIG. 9E). There were no significant correlations between P1 amplitude and activation within any of the other fMRI motion-activated ROIs, including MT+(e.g., $p>0.25$ for all) nor with behavioral measures of coherent motion detection (e.g., $p>0.150$).

Exemplary Schizophrenia Steady-State Evoked Potentials

Ash show in the exemplary chart of FIG. 10A, compared to HC subjects 1005, the ssVEP response at the driving frequency of 10 Hz was significantly diminished in Sz patients 1010 across all stimuli (e.g., $F(1,59)=12.77$, $p=0.001$). (See, e.g., FIGS. 10A and 10B). Unlike the P1 and N2m to stimulus- and motion-onset, which were selectively reduced for LSF stimuli, the ssVEP was equivalently reduced to all stimuli in Sz patients 1010 (e.g., Group x Stimulus: $F(1,59)=0.094$ $p=0.911$). (See, e.g., FIG. 10C). Additionally, the ssVEP response did not correlate with fMRI activation in either the MOG (e.g., Sz: $r=-0.18$, $p=0.443$; HC: $r=-0.32$, $p=0.22'7$) or MT+(e.g., Sz: $r=0.015$, $p=0.81'7$; HC: $r=0.26$, $p=0.323$) in either subject group. In the ROI for the pulvinar, however, significantly reduced activation in Sz patients 1010, (e.g., $F(1,35)=6.69$, $p=0.014$) (see, e.g., FIG. 10D) correlated with patients' reduced ssVEP, (e.g., averaged over all stimuli) (e.g., $r=0.46$, $p=0.038$). This correlation was also significant for HC subjects 1005 (e.g., $r=0.62$, $p=0.010$) and across subject groups (e.g., $r=0.60$, $p<0.001$). (See, e.g., FIG. 10E). No further significant correlations were observed between ssVEP amplitude and fMRI activation in any other ROI (e.g., $p>0.231$ for all). While ssVEP amplitude and coherent motion detection thresholds were significantly correlated across groups (e.g., $r=-0.44$, $p<0.001$) and in HC subjects alone (e.g., $r=-0.42$, $p=0.045$), the correlation was not statistically significant within Sz patients 1010 (e.g., $r=-0.28$, $p=0.089$).

Exemplary Schizophrenia Time-Frequency Analysis

Figures 11A, 11B, 11C:
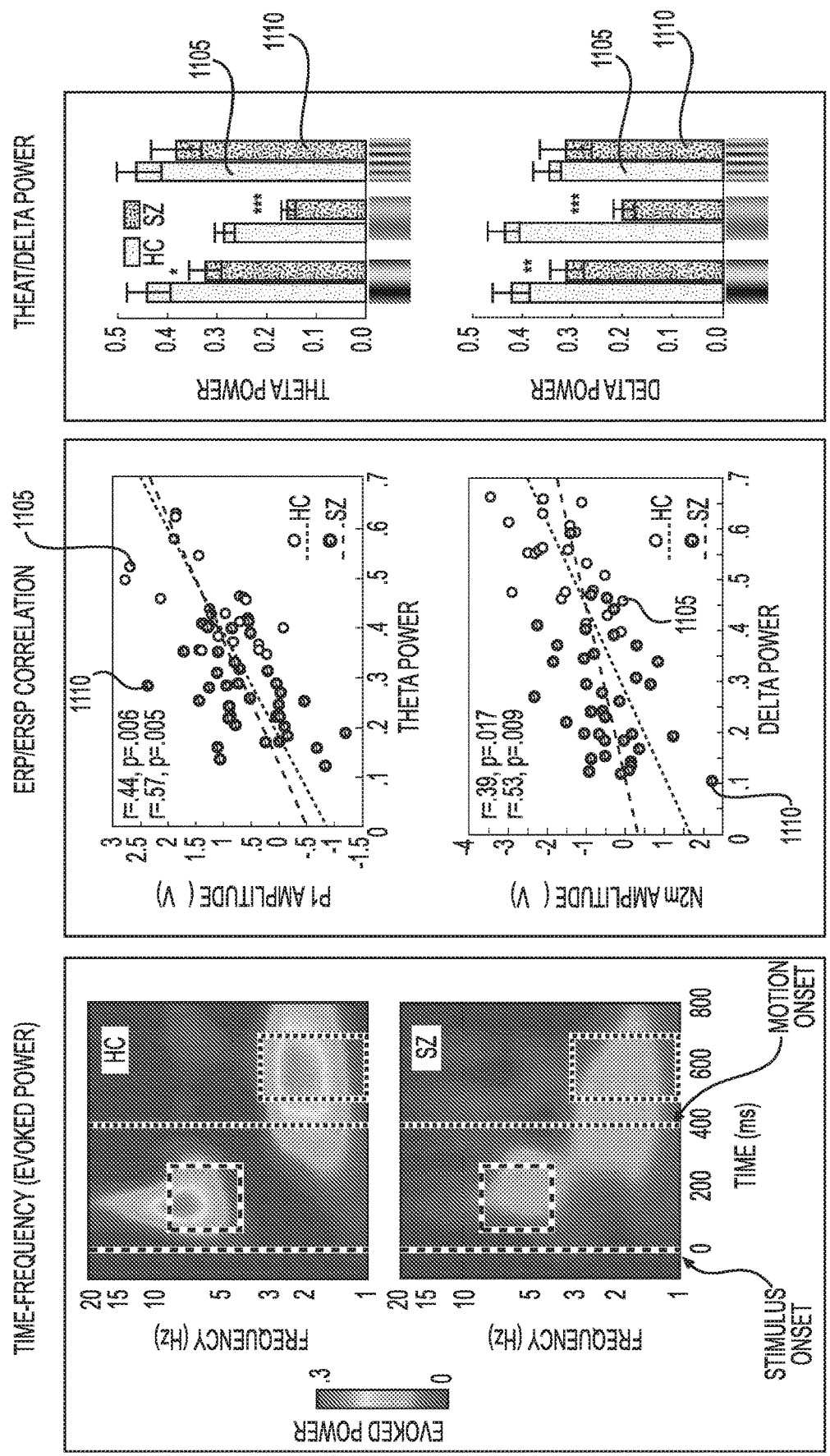
FIG. 11A is a set of exemplary time-frequency plots of evoked power according to an exemplary embodiment of the present disclosure.
FIG. 11B is a set of charts illustrating an exemplary correspondence between evoked power and the ERP amplitude according to an exemplary embodiment of the present disclosure.
FIG. 11C is a set of charts illustrating an exemplary evoked theta and delta power for each stimulus type according to an exemplary embodiment of the present disclosure.

When analyzed in the frequency domain, stimulus-onset elicited an increase mainly in evoked theta (e.g., 4-7 Hz) power, extending into the low alpha band (e.g., 8-10 Hz), which was followed by increased power in the delta band (e.g., 1-3 Hz) in response to the onset of stimulus motion. (See, e.g., exemplary time-frequency plots shown in FIG. 11A). In both groups (e.g., HC 1105 and SZ 1110), these increases in theta and delta power correspond, respectively, to the P1 (e.g., Sz: $r=0.44$, $p=0.006$; HC: $r=0.57$, $p=0.005$) and N2m components of the ERP (e.g., Sz: $r=-0.39$, $p=0.017$; HC: $r=-0.53$, $p=0.009$). (See, e.g., exemplary charts shown in FIG. 11B). Like P1 amplitude, theta power was significantly reduced, overall, in Sz patients 1110 (e.g., $F(1,59)=8.20$, $p=0.006$), especially in response to the onset of LSF stimuli. (See, e.g., exemplary top chart shown in FIG. 11C) as evidenced by a significant group difference when these were tested independently (e.g., $F(2,58)=13.26$, $p<0.001$) but not when HSF stimuli were tested alone (e.g., $F(1,59)=1.14$, $p=0.289$). Likewise, across all stimuli, Sz patients 1110 showed highly reduced evoked delta power following the onset of stimulus motion (e.g., $F(1,59)=22.60$, $p<0.001$), and this deficit, like N2m, was largest for LSF stimuli (e.g., $F(2,58)=20.89$, $p<0.001$) versus HSF stimuli when tested independently (e.g., $F(1,59)=3.94$, $p=0.052$). (See, e.g., exemplary bottom chart shown in FIG. 11C).

Exemplary Schizophrenia Discussion

The exemplary system, method, and computer-accessible medium, according to an exemplary embodiment of the present disclosure, can utilize behavioral measures in combination with fMRI and ERP recordings to investigate motion processing abnormalities in Sz in relation to magnocellular pathway dysfunction. Patients showed significantly reduced amplitude of the motion-sensitive N2m component, which correlated with impaired activation of area MT+ to moving stimuli. Both N2m and MT+ deficits in Sz patients correlated with impaired ability to detect coherent motion. These findings suggest that dysfunction of early cortical visual pathways contribute to motion perception deficits in Sz and lend support to 'bottom-up' theories for compromised motion processing. (See, e.g., References 71 and 106).

In addition to impaired motion processing, Sz patients exhibited a pattern of abnormal sensory processing of static stimulus onsets consistent with prior theories of impaired magnocellular function. Specifically, as in previous studies (see, e.g., References 56 and 60), the sensory-evoked P1 component elicited by the onset of visual stimuli was significantly reduced in patients with Sz for LSF, but not HSF, stimuli. Further, P1 deficits were correlated with diminished activation of the MOG, one of the putative cortical generators of the P1 component (see, e.g., References 57-59) and a known target of the magnocellular pathway. Recent studies have found that the magnocellular system functions in a non-linear mode depend upon functional characteristics of the glutamatergic N-methyl-D-aspartate ("NMDAR") system, suggesting that visual dysfunction in Sz can reflect, in part, NMDAR-mediated dysfunction within early visual regions.

Recordings of ssVEPs were used as a convergent approach for physiological assessment of early visual processing in Sz. As in previous studies, entrained ssVEP power in the alpha band was reduced in patients with Sz (see, e.g., References 82, 85, and 86) and was associated with reduced activation of the pulvinar nucleus of the thalamus, consistent with primate studies indicating that the pulvinar can play an important role in the generation of scalp-recorded alpha oscillations. (See, e.g., References 90 and 91). Although pulvinar abnormalities in Sz can be well established based upon anatomical (see, e.g., References 107-109) and metabolic (see, e.g., References 110 and 111) investigations, the consequences of pulvinar dysfunction have been investigated to a limited degree. Thus, the alpha-frequency ssVEPs can provide a useful method for assessing the functional integrity of the pulvinar in Sz and, further, the pulvinar can play an important role in sensory-processing impairments in Sz.

In the frequency domain, stimulus-onset ERPs consisted mainly of modulations of activity in the theta band as previously reported. (See, e.g., Reference 94). By contrast, the N2m motion-related ERP consisted of power modulations in the delta band. Delta activity can be increasingly viewed as the base of an oscillatory hierarchy controlling neuronal excitability within sensory cortex. (See, e.g., References 112 and 113). Using the exemplary system, method and computer-accessible medium, it was found that impaired delta activity in Sz can be associated with reduced target detection within auditory cortex (see, e.g., Reference 113) suggesting that delta impairments can be generalized across sensory systems and can be related to impaired thalamic processing. (See, e.g., Reference 93).

Exemplary Methods and Materials for Clinical High Risk Individuals with Attenuated Positive Symptoms Exemplary Attenuated Positive Symptom Subjects Participants were 63 DSM-5 schizophrenia patients, 32 attenuated psychosis patients diagnosed using the Structured Interview for Prodromal Syndromes ("SIPS"); 44 healthy volunteers of similar-age to the schizophrenia group ("controls") and 23 healthy volunteers of similar age to the attenuated psychosis group ("young controls"). All schizophrenia patients were on a stable dose of medication. A subset of 21 schizophrenia patients/16 controls participated in the fMRI study.

For attenuated psychosis patients, exclusion criteria included history of threshold psychosis or family history of psychosis, risk of harm to self/others incommensurate with outpatient care, major medical or neurological disorder and IQ<70. Additionally, attenuated psychosis symptoms could not occur solely in the context of substance use or withdrawal or be better accounted for by another disorder. Two years after initial identification, six subjects (19%) had received a diagnosis of schizophrenia. Informed consent was obtained from all subjects following full explanation of the procedures.

Exemplary Methods for Attenuated Psychosis Patients including EEG stimuli and tasks; EEG recordings and data analysis; fMRI stimuli and tasks; fMRI acquisition and data analysis are as described above for corresponding Exemplary Schizophrenia sections.

Exemplary Attenuated Psychosis Syndrome Results

Exemplary Attenuated Psychosis Syndrome Delta Activity

Figure 12A:
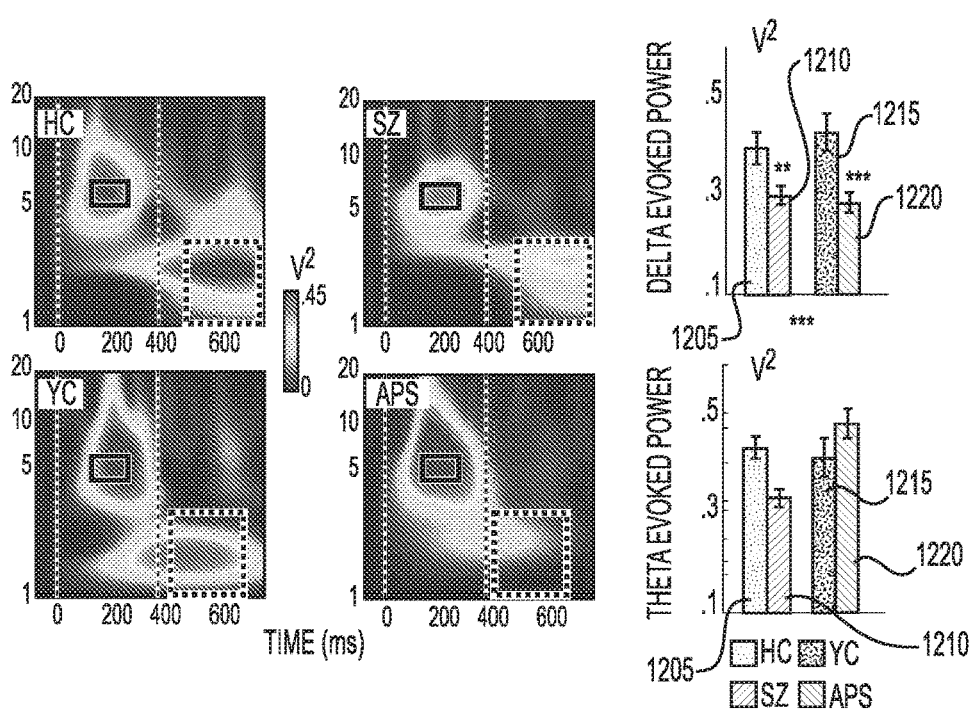
FIG. 12A is a set of exemplary time-frequency charts of evoked power according to an exemplary embodiment of the present disclosure.

Motion-related delta power differed significantly between patients and controls ($F(1,152)=17.66$, $p<0.00001$, $d=0.68$) with no significant main effect of age group ($F(1,152)=0.006$, $p=0.938$, $d=0.02$) or clinical status X age-group interaction ($F(1,152)=0.779$, $p=0.379$). Highly significant between group differences were observed for both schizophrenia ($p<0.01$) and attenuated psychosis ($p<0.001$) patient groups relative to their respective control groups. (See, e.g., time frequency charts shown in FIG. 12A).

There was also a significant stimulus-type X clinical status interaction ($F(2,151)=3.45$, $p=0.034$), reflecting greater deficits high ($t(160)=4.50, p<0.0001$, $d=0.72$) and low ($t(160)=4.50, p<0.0001$, $d=0.53$) luminance contrast, low SF stimuli relative to high SF stimuli ($t(160)=4.50$, $p<0.0001$, $d=0.43$), supporting preferential magnocellular system involvement.

Exemplary Attenuated Psychosis Syndrome Theta Activity

As opposed to motion-onset responses, stimulus-onset (theta) responses were not significantly different between patients and controls overall ($F(1,152)=0.27$, $p=0.607$, $d=0.08$). However, there was a highly significant clinical status X age-group interaction ($F(1,152)=9.14$, $p=0.003$), reflecting significantly reduced mean theta activity in schizophrenia patients compared to their controls ($p<0.001$), but preserved stimulus-onset responses in attenuated psychosis individuals. (See, e.g., time frequency charts shown in FIG. 12A).

The effect of age-group was significant ($F(1,152)=4.99$, $p=0.027$, $d=0.36$), reflecting larger responses in younger versus older individuals irrespective of clinical status. The stimulus-type X clinical/non-clinical interaction was non-significant ($F(2,151)=0.757$, $p=0.470$). There was no main effect of testing site ($F(1,152)=0.013$, $p=0.911$, $d=0.02$) nor site X age-group ($p=0.173$) nor site X clinical status ($p=0.898$) interaction.

Exemplary Attenuated Psychosis Syndrome ssVEP Activity

Figure 12B:
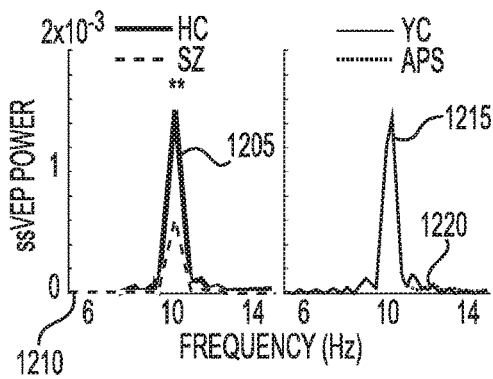
FIG. 12B is an exemplary chart of steady-state visual evoked potential power according to an exemplary embodiment of the present disclosure.

As with theta, ssVEP power was not significantly different between patients and controls overall ($F(1,152)=2.20$, $p=0.140$, $d=0.24$), but did show a significant clinical status X age-group interaction ($F(1,152)=6.20$, $p=0.014$) reflecting significant deficits in schizophrenia patients compared to their controls. (See, e.g., HC 1205, SZ 1210, Young Control $YC_{[HAK1]}$ 1215 and Antiphospholipid Syndrome $APS_{[HAK2]}$ 1220 shown in the chart shown in FIG. 12B).

Exemplary Attenuated Psychosis Syndrome Motion Sensitivity

Figure 12C:
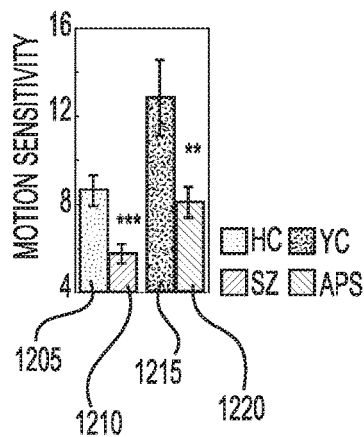
FIG. 12C is an exemplary chart of motion sensitivity according to an exemplary embodiment of the present disclosure.
Figure 12D:
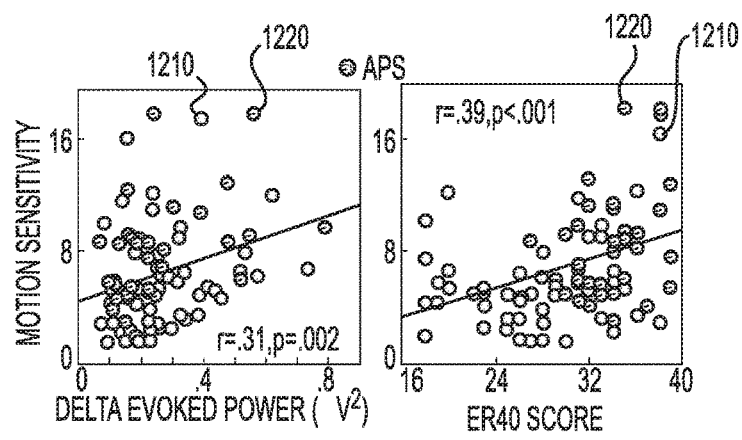
FIG. 12D is a set of charts illustrating an exemplary correspondence between delta evoked power and face emotion recognition scores, and motion sensitivity according to an exemplary embodiment of the present disclosure.

As with delta, behavioral motion sensitivity differed significantly between the patients and controls ($F(1,152)=20.02$, $p<0.0001$, $d=0.72$), reflecting significant reductions in both schizophrenia ($p<0.001$) and attenuated psychosis ($p<0.01$) patients vs. their respective controls. (See, e.g., charts shown in FIG. 12C). Additionally, there was a significant main effect of age-group ($F(1,152)=17.401$, $p<0.0001$, $d=0.66$), reflecting better performance in younger vs. older individuals. However, clinical status and age did not significantly interact ($F(1,152)=1.05$, $p=0.305$).

Though motion sensitivity differed significantly as a function of testing site, ($F(1,152)=5.03$, $p=0.026$, $d=0.36$), there was no interaction between site and clinical status ($F(1,152)=0.273$, $p=0.602$) nor site and age ($F(1,152)=2.32$, $p=0.130$).

Across the patient groups (e.g., SZ 1305 and Antiphospholipid Syndrome $APS_{[HAK3]}$ 1310), reduced motion-evoked delta activity correlated with lower scores on the MCCB Overall ($r=0.397$, $p=0.001$), Visual Learning ($r=0.408$, $p=0.0005$) (see, e.g., charts shown in FIG. 13A), Attention Vigilance ($r=0.271$, $p=0.024$) and Speed of Processing domains ($r=0.392$, $p=0.001$). Similarly, mean theta power evoked by stimulus onset correlated with scores on the Visual Learning ($r=0.296$, $p=0.014$) and Speed of Processing domains ($r=0.406$ $p=0.001$).

Exemplary Attenuated Psychosis Syndrome Correlations with Clinical Measures

Across the patient groups (e.g., SZ 1305 and APS 1310), reduced motion-evoked delta activity correlated with lower scores on the MCCB Overall ($r=0.397$, $p=0.001$), Visual Learning ($r=0.408$, $p=0.0005$) (see, e.g., charts shown in FIG. 13A), Attention Vigilance ($r=0.271$, $p=0.024$) and Speed of Processing domains ($r=0.392$, $p=0.001$). Similarly, mean theta power evoked by stimulus onset correlated with scores on the Visual Learning ($r=0.296$, $p=0.014$) and Speed of Processing domains ($r=0.406$ $p=0.001$).

Exemplary Attenuated Psychosis Syndrome Transition to Schizophrenia

Of the 32 attenuated psychosis individuals, 6 transitioned to psychosis (all schizophrenia) over a 2-year follow up period. Within attenuated psychosis individuals, the ratio between delta and theta activity differed significantly between those who did and did not convert to schizophrenia ($t(30)=2.91, p=0.007$, $d=1.06$) (see, e.g., chart shown in FIG. 13B) with a cutoff value of 0.7 (e.g., equivalent to 99% confidence interval for remaining subjects) correctly predicting 100% of converters, but excluding 9/26 (35%) of non-converters (LR $\chi^2=4.48$, $p=0.034$).

Furthermore, across subjects, delta/theta ratio correlated significantly with positive ($r=-0.32$, $p=0.036$), negative ($r=-0.32$, $p=0.036$) and general ($r=-0.33$, $p=0.029$) symptoms as ascertained by the SOPS. Finally, face ER40 also significantly differentiated between converters and non-converters ($t(30)=2.25, p=0.045$, $d=0.82$). By contrast, no significant differences were observed for either neurocognitive ("MCCB") or symptom ("SOPS") measures Exemplary Attenuated Psychosis Syndrome Discussion As compared to individuals with schizophrenia, these findings show that individuals with Attenuated Psychosis Syndrome show deficits only in delta activity. By contrast, theta activity may not be significantly affected. The ratio of delta/theta activity can serve as a predictor of conversion to schizophrenia among clinical high-risk individuals.

Exemplary Autism Spectrum Disorder Introduction

Visual perceptual processing can also differ between individuals with autism spectrum disorder vs. typically developing individuals ("neurotypicals"). The etiology of the differential visual processing may not be known. Furthermore the ability of specific visual neurophysiological and neuroimaging-based measures to differentiate individuals with ASD from those with other neuropsychiatric conditions such as schizophrenia has not been previously evaluated.

Exemplary Autism Spectrum Disorder Subjects

Participants were 20 adults with ASD (e.g., mean age 29.0 years, 4 female), 19 patients diagnosed with SZ (e.g., mean age 37.8 years, 1 female) and 17 HC volunteers (e.g., mean age 34.0 years, 2 female). All participants had IQ>70 and at least 20/22 (1.02) corrected visual acuity on the Logarithmic Visual Acuity Chart (Precision Vision).

Exemplary Autism Spectrum Disorder Resting State Functional Connectivity

Exemplary methods for coherent motion stimulation, electrophysiology, neurophysiology and functional, and functional MRI are described herein and above.

Resting state data ("rsFMRI") was acquired from all participants while subjects lay awake with eyes closed. Wakefulness during the scan was verified by the MR technician. Functional images (TR (s)/TE (ms)/flip angle (degrees)=2/30/90, 2.8 mm slice thickness, 34 axial slices, 0.5 mm gap, 180 acquisitions) were acquired over the course of one six-minute scan and pre-processed as described above for fMRI. Large transients were removed through interpolation (3dDespike) and the ANATICOR method was used to remove further physiological confounds. Individual masks of large ventricles and white matter were generated from the segmentation of structural scans using FreeSurfer. The white matter mask was eroded by one voxel to prevent partial volume effects. A nuisance regressor was obtained by extracting the EPI average timecourse within the ventricle mask and local nuisance regressors were obtained by calculating the local white matter signal time course for voxels within a 3 cm radius of gray matter. These nuisance regressors and the 24 regressors derived from motion parameters were removed from the EPI time series using AFNI's @ANATICOR to yield a residual timeseries which was used in subsequent correlation analyses.

Time courses of mean activity within the five visual composite parcellations of the HCP-MMP1.0 atlas (V1, Early visual, Dorsal stream, Ventral stream, MT+ complex) were extracted from the residualized images. To assess the relationship between thalamocortical connectivity and visual/motion processing impairments in SZ and ASD subjects, time courses from the pulvinar and the lateral geniculate nucleus of the thalamus were also extracted, based on subcortical FreeSurfer masks. The time series from these 5 cortical and 2 sub-cortical regions were correlated with one another in pairwise fashion to yield a connectivity strength value between each region.

Exemplary Autism Spectrum Disorder Motion and Face Processing

After covarying for both age and IQ, motion sensitivity was significantly different across groups ($F(2,50)=11.70$, $p=0.002$). As previously discussed, SZ patients had significantly reduced motion sensitivity (e.g., higher coherence thresholds) than HC's ($p=0.003$). Similarly, motion sensitivity was lower in ASD individuals, compared to controls ($p=0.006$) and did not differ from that of SZ patients ($p=0.956$).

Further, both SZ ($F(1,30)=13.27, p=0.001$) and ASD participants ($F(1,30)=9.92, p=0.003$) scored significantly lower on the ER40 face-emotion recognition test, compared to HC's. Additionally, across all subjects ($r=0.43, p=0.001$) and within the HC ($r=0.54, p=0.037$) and ASD ($r=0.57, p=0.011$) groups alone, these two behavioral measures were strongly correlated.

Exemplary Autism Spectrum Disorder Theta and Delta Evoked Power

Average responses to visual stimuli are shown in the time-frequency charts of FIG. 14A. Mean values by group are shown in the chart of FIG. 14B for HC 1405, SZ 1410 and ASD 1415.

Across subjects and hemispheres, the onset of all stimuli elicited an increase in theta evoked power, maximal over latero-occipital scalp sites that was significantly different across all groups ($F(2,53)=10.27$, $p=0.0002$). Across groups, responses were largest over the right hemisphere (RH) ($F(1,53)=17.39$, $p=0.0001$). This hemispheric asymmetry was larger for ASD subjects 1415, as evidenced by the interaction between group and hemisphere ($F(2,53)=4.59$, $p=0.015$). When tested separately, theta power was significantly larger, overall, in subjects with ASD compared to both healthy controls ($F(1,35)=4.62$, $p=0.038$), and patients with SZ ($F(1,37)=17.70$, $p=0.0002$). As reported previously, theta power (e.g., collapsed across stimulus types) was significantly lower in SZ patients compared to controls ($F(1,34)=7.62$, $p=0.009$).

Motion-onset responses elicited an increase in delta (e.g., 1-4 Hz) evoked power over bilateral occipital scalp regions. Overall, this delta response was significantly different across groups ($F(2,53)=6.20$, $p=0.004$) with lower magnitude responses in both ASD ($F(1,35)=11.01$, $p=0.002$) and SZ ($F(1,34)=4.48$, $p=0.041$), compared to control subjects.

Exemplary Autism Spectrum Disorder Alpha Measures

Visual steady-state potentials were elicited in response to a 10 Hz stimulus. Mean steady-state visual evoked potential surface maps are shown in the scalp distributions shown in FIG. 14C. Mean values across groups are shown in the chart of FIG. 14D.

Across all subjects, steady-state visual evoked potential power at 10 Hz was maximal over midline parieto-occipital sites but showed a highly significant difference across groups (F(1,34)=19.56, p<0.0001) Single-trial alpha event-related desynchronization responses ("ERD") are shown in the time-frequency charts and scalp distributions of FIG. 14E. Mean values across subjects are shown in chart of FIG. 14F. Single-trial alpha power during the pre-stimulus interval was significantly higher in patients with SZ (F(1,33)=8.25, p=0.007) and in ASD participants (F(1,35)=4.64, p=0.038), compared to HC subjects. In patients with SZ, the mean alpha ERD was significantly reduced, when compared to HC subjects (F(1,33)=5.96, p=0.020). In contrast, the alpha ERD was significantly enhanced in ASD subjects compared to controls (F(1,35)=5.31, p=0.02'7). Across, ASD and HC subjects, the ERD was marginally larger over the RH (F(1,35)=3.27, p=0.050) but with no group x hemisphere interaction (F(2,34)=1.50, p=0.237).

Exemplary Autism Spectrum Disorder Functional MRI

BOLD activation (e.g., beta coefficients) in response to moving stimuli was analyzed within five cortical ROIs and in the pulvinar nucleus of the thalamus. When compared to HC, activation in the SZ group was significantly reduced within the MT+ complex (F(1,34)=7.14, p=0.011) and the pulvinar nucleus (F(1,34)=6.30, p=0.017). Within the ROI for V1, control subjects showed a deactivation (e.g., negative beta coefficients) which was also reduced in SZ patients (F(1,34)=4.46, p=0.042).

In ASD subjects, mean activation in the MT+ complex was similarly reduced (F(1,35)=6.81, p=0.013) as in SZ patients. In contrast, ASD participants showed increased activation, relative to controls, in both the early visual (F(1,35)=5.31, p=0.02'7) and dorsal stream (F(1,35)=5.03, p=0.031) ROIs. Activation within all other cortical ROIs and the pulvinar was equivalent in ASD compared to HC subjects (p>0.25, all) and there were no main effects or interactions with hemisphere (p>0.45, all).

Across all subjects, increased activation in MT+ correlated with higher amplitude delta evoked activity following the onset of stimulus motion (r=0.57, p<0.0001) as well as with improved motion sensitivity (r=0.44, p=0.001). Additionally, across subjects (r=0.57, p<0.0001), but especially in the ASD group alone (r=0.61, p=0.004), greater activation of dorsal areas was associated with increased theta-band activity. In ASD subjects, increased dorsal activation also correlated with higher amplitude ongoing (e.g., pre-stimulus) alpha power (r=0.57, p=0.008, not shown). Further, there was a highly significant correlation across all subjects between the magnitude of the alpha ERD and activation in the pulvinar ROI (r=-0.51, p<0.0001). This correlation was independently significant in the SZ (r=-0.52, p=0.028) and ASD (r=-0.64, p=0.002) groups.

Exemplary Autism Spectrum Disorder Resting State Functional MRI

Functional connectivity (Pearson's r) was computed between the 5 cortical and 2 sub-cortical regions. Across all 21 pairwise correlations, connectivity was significantly reduced in patients with SZ (F(1,34)=9.81, p=0.004) but not in ASD individuals (F(1,35)=1.26, p=0.2'70), when compared to HC subjects. When each pairwise correlations between each ROI and the others were tested separately, connectivity for all the cortical ROIs (V1: t(34)=3.19, p=0.003; early visual: t(34)=3.19,p=0.003; dorsal stream: t(34)=3.19,p=0.003; ventral stream: t(34)=3.19,p=0.003; MT+ complex: t(34)=3.19,p=0.003) was significantly reduced in SZ patients, relative to controls.

Connectivity involving the two sub-cortical ROIs (LGN: t(34)=3.19,p=0.003; pulvinar: t(34)=3.19,p=0.003) was equivalent between SZ and HC groups. Unlike SZ patients, mean connectivity between all ROIs was equivalent to that of HC, (p>0.30, all) with the exception of connectivity with the pulvinar nucleus, which was significantly greater in ASD subjects compared to controls t(35)=-2.49,p=0.017.

Exemplary Autism Spectrum Disorder Discriminant Function Analysis

Figure 15A:
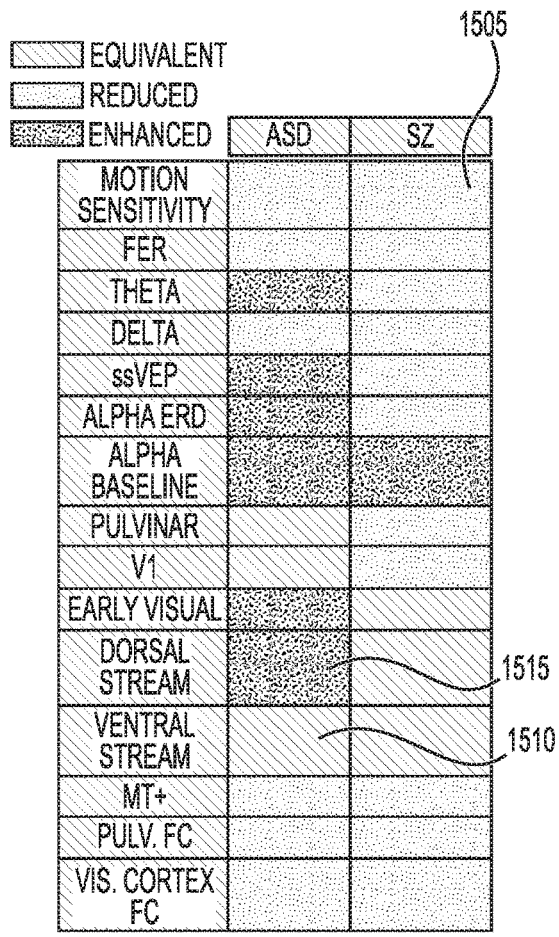
FIG. 15A is an exemplary diagram of pattern of changes across measures according to an exemplary embodiment of the present disclosure.

To determine which of the physiological measures can best differentiate the three subject groups, a forward stepwise discriminant function analysis was carried out using group membership as the dependent variable mean and mean values for 14 measures as independent predictor variables. For example, the diagram shown in FIG. 15A illustrates equivalent 1505, reduced 1510 and enhanced 1515 characteristics for ASD and SZ.

Figure 15B:
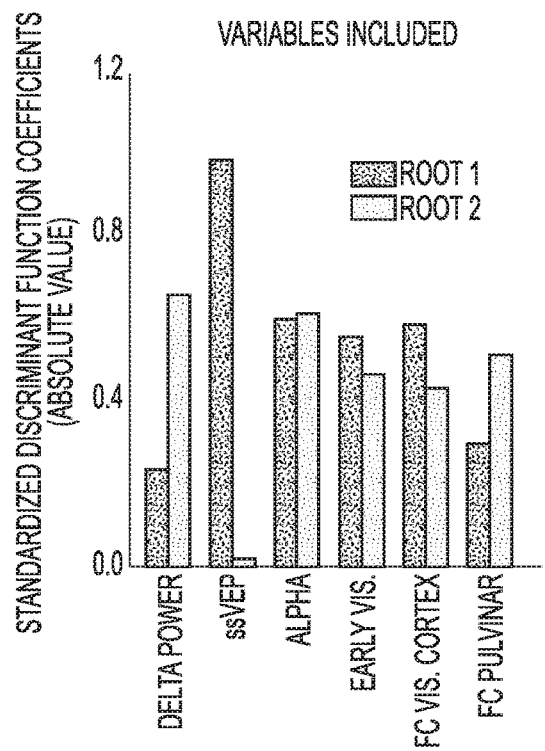
FIG. 15B is an exemplary chart showing results of a discriminant function analysis according to an exemplary embodiment of the present disclosure.
Figure 15C:
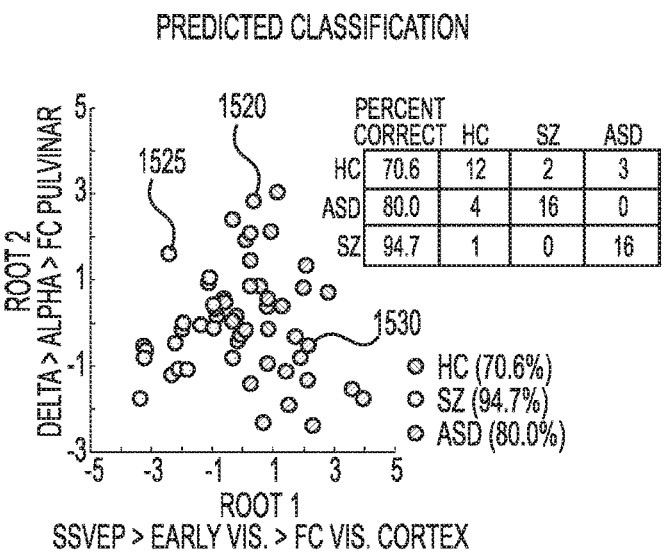
FIG. 15C is an exemplary chart showing predicted classifications of healthy controls ("HC"), ASD and schizophrenia ("SZ") individuals according to an exemplary embodiment of the present disclosure.

5 EEG measures (e.g., delta, theta, ssVEP, alpha pre-stimulus power, alpha ERD); 6 fMRI measures (e.g., 5 cortical ROIs, pulvinar ROI) and 3 functional connectivity measures (e.g., mean correlation between all cortical ROIs, pulvinar connectivity, LGN connectivity). After the sixth (e.g., final) procedure of the regression (F to enter=3.5), 6 variables were left in the model. For example, the chart shown in FIG. 15B illustrates a variable comparison for Root1 and Root2. As shown in the chart of FIG. 15C, the analysis correctly predicted group membership for 70.6%, 80% and 94.7% of HC subjects 1520, SZ subjects 1525 and ASD subjects 1530, respectively. Importantly, none of the SZ patients were incorrectly classified as ASD, or vice-versa.

In the canonical analysis, two discriminant functions were derived (see, e.g., chart shown in FIG. 15C), Root1 was weighted most heavily by the ssVEP, visual cortex connectivity and early visual BOLD variables, with individual canonical scores significantly differing between HC and ASD (t(35)=3.86,p=0.0004), HC and SZ (t(34)=8.74, p<0.0001) and ASD versus SZ (t(37)11.43,p<0.0001). Delta evoked power, alpha pre-stimulus power and pulvinar functional connectivity were the variables that contributed most to the second function, Root2. The canonical correlations for this selection of predictors was 0.82 for Root1 (Wilks' lambda=0.200, $\chi^2$(12)=79.53,p<0.0001) and 0.63 for Root2 (Wilks' lambda=0.630, $\chi^2$(5)=25.01,p=0.0001).

Exemplary Autism Spectrum Disorder Discussion

The exemplary system, method, and computer-accessible medium, according to an exemplary embodiment of the present disclosure, can utilize behavioral measures in combination with task-based fMRI, resting state functional connectivity fMRI and ERP recordings to identify differential patterns of visual brain function in individuals with ASD. These findings suggest that differential processing within the early visual system can affect social function in individuals with ASD.

As opposed to SZ individuals who showed primarily reduced visual responses, ASD individuals showed increases in visual processing as reflected in both neurophysiological and fMRI-based measures. The combination of EEG-, task-based fMRI, and resting state fMRI measures distinguished groups to a greater extent than either set of measures alone.

Thus, the exemplary system, method, and computer-accessible medium, according to an exemplary embodiment of the present disclosure, can be used to study and/or demonstrate how subcortical and cortical contributions to impaired sensory and motion processing in Sz, can be consistent with dysfunction of the magnocellular visual pathways and potentially related to underlying NMDAR dysfunction. Further, evidence can be provided tying impairments in alpha oscillations to dysfunction of the thalamic pulvinar nucleus, a subcortical structure, which can play an important role in mediation of stimulus- and attention-driven modulation of higher order visual regions, thereby supporting an increased focus on the role of subcortical mechanisms underlying cognitive dysfunction in Sz, aging, Alzheimers disease, and ASD.

Figure 16:
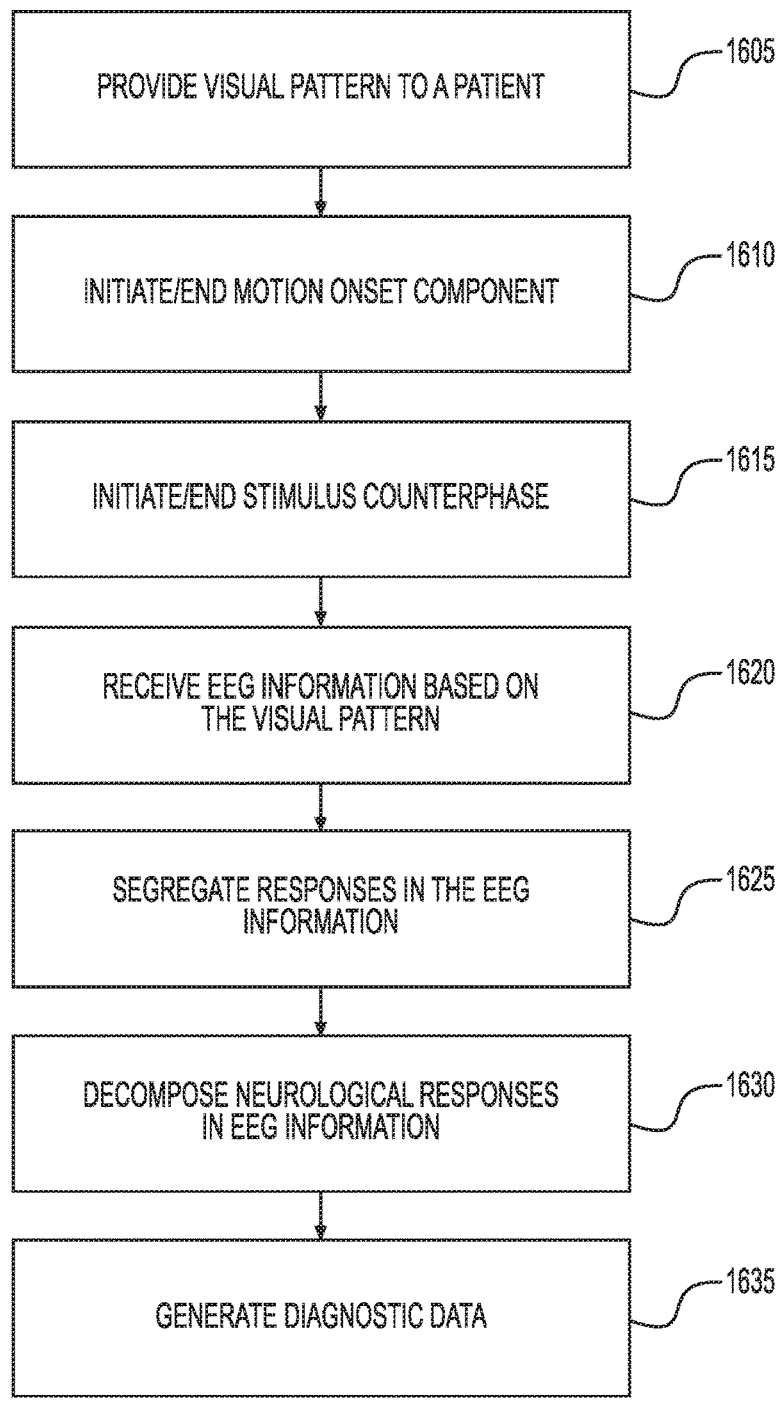
FIG. 16 is an exemplary flow diagram of a method for generating diagnostic data associated with a likelihood of a patient developing mental disease according to an exemplary embodiment of the present disclosure.

FIG. 16 shows an exemplary flow diagram of a method 1600 for generating diagnostic data associated with a likelihood of a patient developing a mental disease according to an exemplary embodiment of the present disclosure. For example, at procedure 1605, a visual pattern can be provided to a patient. After the pattern is provided to the patient, at procedure 1610, a motion onset component can begin, which can then be ended. At procedure 1615, a stimulus counterphase can be initiated and ended, after the ending of the motion onset component. At procedure 1620, EEG information can be received based on the visual pattern. At procedure 1625, responses in the EEG information from a subcortical magnocellular and parvocellular visual pathways based on a low spatial frequency stimulus and a high spatial frequency stimulus can be segregated. At procedure 1630, responses in the EEG information can be decomposed. At procedure 1635, diagnostic data can be generated, for example, based on the EEG information.

Figure 17:
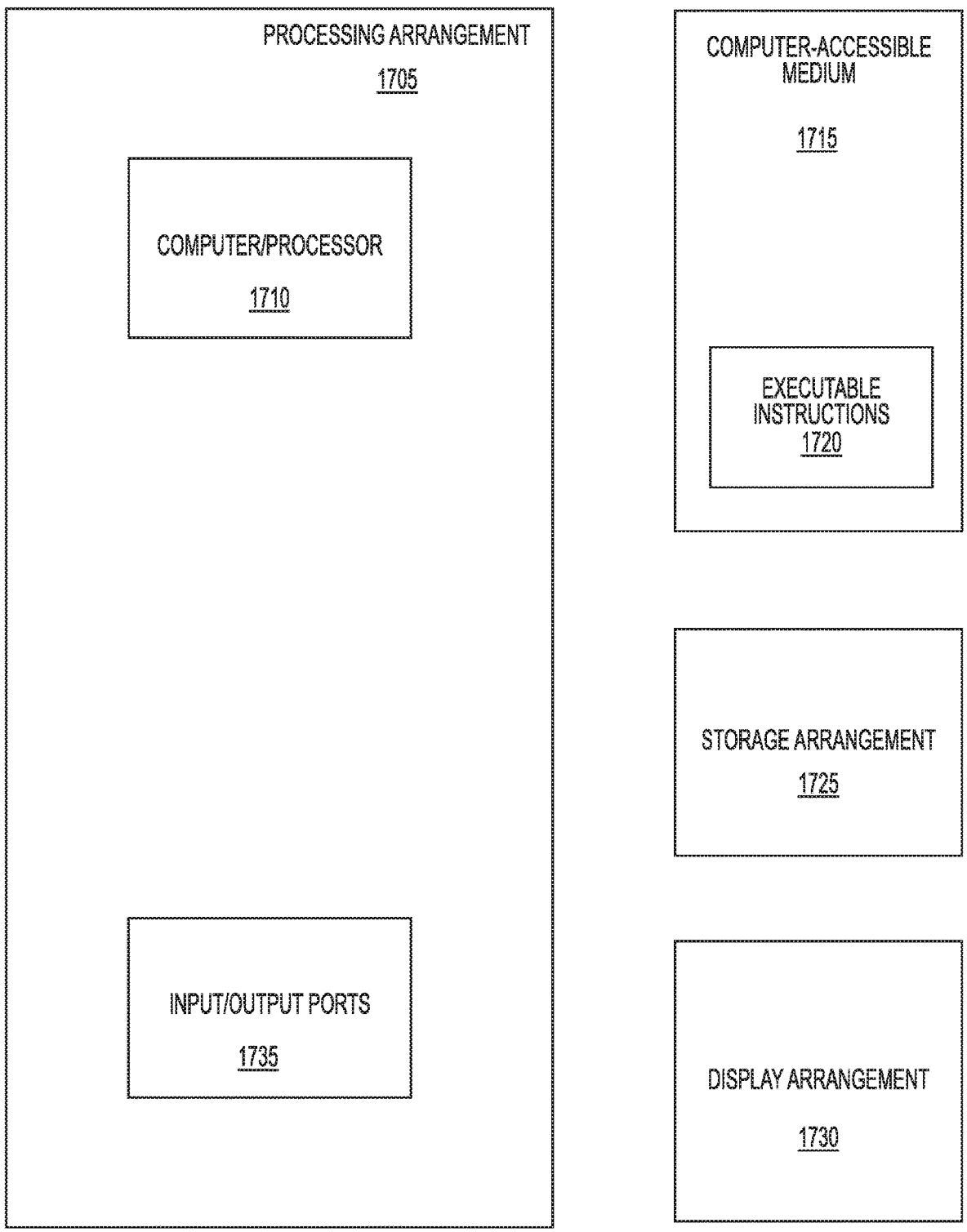
FIG. 17 is an illustration of an exemplary block diagram of an exemplary system in accordance with certain exemplary embodiments of the present disclosure.

FIG. 17 shows a block diagram of an exemplary embodiment of a system according to the present disclosure. For example, exemplary procedures in accordance with the present disclosure described herein can be performed by a processing arrangement and/or a computing arrangement 1705. Such processing/computing arrangement 1705 can be, for example entirely or a part of, or include, but not limited to, a computer/processor 1710 that can include, for example one or more microprocessors, and use instructions stored on a computer-accessible medium (e.g., RAM, ROM, hard drive, or other storage device).

As shown in FIG. 17, for example a computer-accessible medium 1715 (e.g., as described herein above, a storage device such as a hard disk, floppy disk, memory stick, CD-ROM, RAM, ROM, etc., or a collection thereof) can be provided (e.g., in communication with the processing arrangement 1705). The computer-accessible medium 1715 can contain executable instructions 1720 thereon. In addition or alternatively, a storage arrangement 1725 can be provided separately from the computer-accessible medium 1715, which can provide the instructions to the processing arrangement 1705 so as to configure the processing arrangement to execute certain exemplary procedures, processes, and methods, as described herein above, for example.

Further, the exemplary processing arrangement 1705 can be provided with or include an input/output arrangement 1735, which can include, for example a wired network, a wireless network, the internet, an intranet, a data collection probe, a sensor, etc. As shown in FIG. 17, the exemplary processing arrangement 1705 can be in communication with an exemplary display arrangement 1730, which, according to certain exemplary embodiments of the present disclosure, can be a touch-screen configured for inputting information to the processing arrangement in addition to outputting information from the processing arrangement, for example. Further, the exemplary display 1730 and/or a storage arrangement 1725 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entireties:

[1] Albert M S, DeKosky S T, Dickson D, Dubois B, Feldman H H, Fox N C, et al. The diagnosis of mild cognitive impairment due to Alzheimer's disease: recommendations from the National Institute on Aging-Alzheimer's Association workgroups on diagnostic guidelines for Alzheimer's disease. Alzheimer's & dementia: the journal of the Alzheimer's Association 2011; 7(3): 270-9.

[2] Andrews-Hanna J R, Snyder A Z, Vincent J L, Lustig C, Head D, Raichle M E, et al. Disruption of large-scale brain systems in advanced aging. Neuron 2007; 56(5): 924-35.

[3] Buschke H, Fuld P A. Evaluating storage, retention, and retrieval in disordered memory and learning. Neurology 1974; 24(11): 1019-25.

[4] Butler P D, Abeles I Y, Weiskopf N G, Tambini A, Jalbrzikowski M, Legatt M E, et al. Sensory contributions to impaired emotion processing in schizophrenia. Schizophr Bull 2009; 35(6): 1095-107.

[5] Butler P D, Zemon V, Schechter I, Saperstein A M, Hoptman M J, Lim K O, et al. Early-stage visual processing and cortical amplification deficits in schizophrenia. Arch Gen Psychiatry 2005; 62(5): 495-504.

[6] Carbonell F, Zijdenbos A P, Charil A, Grand'Maison M, Bedell B J, Alzheimer's Disease Neuroimaging I. Optimal Target Region for Subject Classification on the Basis of Amyloid PET Images. J Nucl Med 2015; 56(9): 1351-8.

[7] Cohen J. Statistical Power Analysis for the Behavioral Sciences, 2nd edition. Hillsdale, NJ: Lawrence Erlbaum Assoc.; 1988.

[8] Dixon M L, Andrews-Hanna J R, Spreng R N, Irving Z C, Mills C, Girn M, et al. Interactions between the default network and dorsal attention network vary across default subsystems, time, and cognitive states. Neuroimage 2017; 147: 632-49.
[9] Doniger G M, Silipo G, Rabinowicz E F, Snodgrass J G, Javitt D C. Impaired sensory processing as a basis for object-recognition deficits in schizophrenia. Am J Psychiatry 2001; 158(11): 1818-26.
[10] Green M F, Horan W P, Lee J. Social cognition in schizophrenia. Nat Rev Neurosci 2015; 16(10): 620-31.
[11] Hill J M, Dua P, Clement C, Lukiw W J. An evaluation of progressive amyloidogenic and pro-inflammatory change in the primary visual cortex and retina in Alzheimer's disease (AD). Frontiers in neuroscience 2014; 8: 347.
[12] Jack C R, Jr., Therneau T M, Wiste H J, Weigand S D, Knopman D S, Lowe V J, et al. Transition rates between amyloid and neurodegeneration biomarker states and to dementia: a population-based, longitudinal cohort study. Lancet Neurol 2016; 15(1): 56-64.
[13] Jansen W J, Ossenkoppele R, Knol D L, Tijms B M, Scheltens P, Verhey F R, et al. Prevalence of cerebral amyloid pathology in persons without dementia: a meta-analysis. JAMA 2015; 313(19): 1924-38.
[14] Javitt D C. When doors of perception close: bottom-up models of disrupted cognition in schizophrenia. Annual review of clinical psychology 2009; 5: 249-75.
[15] Javitt D C. Neurophysiological models for new treatment development in schizophrenia: early sensory approaches. Ann N Y Acad Sci 2015; 1344: 92-104.
[16] Javitt D C, Freedman R. Sensory processing dysfunction in the personal experience and neuronal machinery of schizophrenia. Am J Psychiatry 2015; 172(1): 17-31.
[17] Javitt D C, Spencer K M, Thaker G K, Winterer G, Hajos M. Neurophysiological biomarkers for drug development in schizophrenia. Nature reviews 2008; 7(1): 68-83.
[18] Kern R S, Green M F, Fiske A P, Kee K S, Lee J, Sergi M J, et al. Theory of mind deficits for processing counterfactual information in persons with chronic schizophrenia. Psychol Med 2009; 39(4): 645-54.
[19] Lakatos P, Shah A S, Knuth K H, Ulbert I, Karmos G, Schroeder C E. An oscillatory hierarchy controlling neuronal excitability and stimulus processing in the auditory cortex. J Neurophysiol 2005; 94(3): 1904-11.
[20] Lavrencic L M, Kurylowicz L, Valenzuela M J, Churches O F, Keage H A. Social cognition is not associated with cognitive reserve in older adults. Neuropsychol Dev Cogn B Aging Neuropsychol Cogn 2016; 23(1): 61-77.
[21] Luck S J, Mathalon D H, O'Donnell B F, Hamalainen M S, Spencer K M, Javitt D C, et al. A roadmap for the development and validation of event-related potential biomarkers in schizophrenia research. Biol Psychiatry 2011; 70(1): 28-34.
[22] Makeig S, Debener S, Onton J, Delorme A. Mining event-related brain dynamics. Trends Cogn Sci 2004; 8(5): 204-10.
[23] Makeig S, Westerfield M, Jung T P, Enghoff S, Townsend J, Courchesne E, et al. Dynamic brain sources of visual evoked responses. Science 2002; 295(5555): 690-4.
[24] Martinez-Montes E, Cuspineda-Bravo E R, El-Deredy W, Sanchez-Bornot J M, Lage-Castellanos A, Valdes-Sosa P A. Exploring event-related brain dynamics with tests on complex valued time-frequency representations. Statistics in medicine 2008; 27(15): 2922-47.
[25] Martinez A, Gaspar P A, Hillyard S A, Bickel S, Lakatos P, Dias E C, et al. Neural oscillatory deficits in schizophrenia predict behavioral and neurocognitive impairments. Front Hum Neurosci 2015a; 9(371): 371.
[26] Martinez A, Gaspar P A, Hillyard S A, Bickel S, Lakatos P, Dias E C, et al. Neural oscillatory deficits in schizophrenia predict behavioral and neurocognitive impairments. Frontiers in human neuroscience 2015b; 9: 371.
[27] Martinez A, Hillyard S A, Bickel S, Dias E C, Butler P D, Javitt D C. Consequences of magnocellular dysfunction on processing attended information in schizophrenia. Cereb Cortex 2012; 22(6): 1282-93.
[28] Martinez A, Hillyard S A, Dias E C, Hagler D J, Jr., Butler P D, Guilfoyle D N, et al. Magnocellular pathway impairment in schizophrenia: evidence from functional magnetic resonance imaging. J Neurosci 2008; 28(30): 7492-500.
[29] Mattis S. Dementia Rating Scale (DRS). Odessa, F L: Psychological Assessment Resources; 1988.
[30] Palop J J, Mucke L. Network abnormalities and interneuron dysfunction in Alzheimer disease. Nat Rev Neurosci 2016; 17(12): 777-92.
[31] Power J D, Barnes K A, Snyder A Z, Schlaggar B L, Petersen S E. Spurious but systematic correlations in functional connectivity Mill networks arise from subject motion. Neuroimage 2012; 59(3): 2142-54.
[32] Power J D, Cohen A L, Nelson S M, Wig G S, Barnes K A, Church J A, et al. Functional network organization of the human brain. Neuron 2011; 72(4): 665-78.
[33] Revheim N, Butler P D, Schechter I, Jalbrzikowski M, Silipo G, Javitt D C. Reading impairment and visual processing deficits in schizophrenia. Schizophr Res 2006; 87(1-3): 238-45.
[34] Revheim N, Corcoran C M, Dias E, Hellmann E, Martinez A, Butler P D, et al. Reading deficits in schizophrenia and individuals at high clinical risk: relationship to sensory function, course of illness, and psychosocial outcome. Am J Psychiatry 2014; 171(9): 949-59.
[35] Sartucci F, Borghetti D, Bocci T, Murri L, Orsini P, Porciatti V, et al. Dysfunction of the magnocellular stream in Alzheimer's disease evaluated by pattern electroretinograms and visual evoked potentials. Brain Res Bull 2010; 82(3-4): 169-76.
[36] Schechter I, Butler P D, Zemon V M, Revheim N, Saperstein A M, Jalbrzikowski M, et al. Impairments in generation of early-stage transient visual evoked potentials to magno- and parvocellular-selective stimuli in schizophrenia. Clin Neurophysiol 2005; 116(9): 2204-15.
[37] Schultz A P, Chhatwal J P, Hedden T, Mormino E C, Hanseeuw B J, Sepulcre J, et al. Phases of Hyperconnectivity and Hypoconnectivity in the Default Mode and Salience Networks Track with Amyloid and Tau in Clinically Normal Individuals. J Neurosci 2017; 37(16): 4323-31.
[37] Sehatpour P, Dias E C, Butler P D, Revheim N, Guilfoyle D N, Foxe J J, et al. Impaired visual object processing across an occipital-frontal-hippocampal brain network in schizophrenia: an integrated neuroimaging study. Arch Gen Psychiatry 2010; 67(8): 772-82.
[38] Sperling R A, Laviolette P S, O'Keefe K, O'Brien J, Rentz D M, Pihlajamaki M, et al. Amyloid deposition is associated with impaired default network function in older persons without dementia. Neuron 2009; 63(2): 178-88.
[38] Spreng R N, Stevens W D, Viviano J D, Schacter D L. Attenuated anticorrelation between the default and dorsal attention networks with aging: evidence from task and rest. Neurobiol Aging 2016; 45: 149-60.

[39] Whitford V, O'Driscoll G A, Pack C C, Joober R, Malla A, Titone D. Reading impairments in schizophrenia relate to individual differences in phonological processing and oculomotor control: evidence from a gaze-contingent moving window paradigm. J Exp Psychol Gen 2013; 142(1): 57-75.

[40] Yamasaki T, Horie S, Muranaka H, Kaseda Y, Mimori Y, Tobimatsu S. Relevance of in vivo neurophysiological biomarkers for mild cognitive impairment and Alzheimer's disease. J Alzheimers Dis 2012a; 31: S137-S54.

[41] Yamasaki T, Horie S, Muranaka H, Kaseda Y, Mimori Y, Tobimatsu S. Relevance of in vivo neurophysiological biomarkers for mild cognitive impairment and Alzheimer's disease. J Alzheimers Dis 2012b; 31 Suppl 3: S137-54.

[42] Yamasaki T, Horie S, Ohyagi Y, Tanaka E, Nakamura N, Goto Y, et al. A Potential VEP Biomarker for Mild Cognitive Impairment: Evidence from Selective Visual Deficit of Higher-Level Dorsal Pathway. J Alzheimers Dis 2016; 53(2): 661-76.

[43] Yeo B T, Krienen F M, Sepulcre J, Sabuncu M R, Lashkari D, Hollinshead M, et al. The organization of the human cerebral cortex estimated by intrinsic functional connectivity. J Neurophysiol 2011; 106(3): 1125-65.

[44] Yoonessi A, Yoonessi A. Functional assessment of magno, parvo and konio-cellular pathways; current state and future clinical applications. Journal of ophthalmic & vision research 2011; 6(2): 119-26.

[45] Zhang D, Liang B, Wu X, Wang Z, Xu P, Chang S, et al. Directionality of large-scale resting-state brain networks during eyes open and eyes closed conditions. Frontiers in human neuroscience 2015; 9: 81.

[46] Zhang H Y, Chen W X, Jiao Y, Xu Y, Zhang X R, Wu J T. Selective vulnerability related to aging in large-scale resting brain networks. PLoS ONE 2014a; 9(10): e108807.

[47] Zhang S, Xu M, Kamigaki T, Hoang Do J P, Chang W C, Jenvay S, et al. Selective attention. Long-range and local circuits for top-down modulation of visual cortex processing. Science 2014b; 345(6197): 660-5.

[48] Kahn R S, Keefe R S. 2013. Schizophrenia Is a Cognitive Illness: Time for a Change in Focus. JAMA Psychiatry.

[49] Bowie C R, Harvey P D. 2006. Cognitive deficits and functional outcome in schizophrenia. Neuropsychiatric disease and treatment 2:531-536.

[50] Nuechterlein K H, Green M F, Kern R S, Baade L E, Barch D M, Cohen J D, Essock S, Fenton W S, Frese F J, 3rd, Gold J M, Goldberg T, Heaton R K, Keefe R S, Kraemer H, Mesholam-Gately R, Seidman L J, Stover E, Weinberger D R, Young A S, Zalcman S, Marder S R. 2008. The MATRICS Consensus Cognitive Battery, part 1: test selection, reliability, and validity. Am J Psychiatry 165:203-213.

[51] Javitt D C. 2009. Sensory processing in schizophrenia: neither simple nor intact. Schizophr Bull 35:1059-1064.

[52] Javitt D C. 2009. When doors of perception close: bottom-up models of disrupted cognition in schizophrenia. Annu Rev Clin Psychol 5:249-275.

[53] Javitt D C, Freedman R. 2015. Sensory processing dysfunction in the personal experience and neuronal machinery of schizophrenia. Am J Psychiatry 172:17-31.

[54] Butler P D, Zemon V, Schechter I, Saperstein A M, Hoptman M J, Lim K O, Revheim N, Silipo G, Javitt D C. 2005. Early-stage visual processing and cortical amplification deficits in schizophrenia. Arch Gen Psychiatry 62:495-504.

[55] Butler P D, Martinez A, Foxe J J, Kim D, Zemon V, Silipo G, Mahoney J, Shpaner M, Jalbrzikowski M, Javitt D C. 2007. Subcortical visual dysfunction in schizophrenia drives secondary cortical impairments. Brain 130:417-430.

[56] Martinez A, Hillyard S A, Bickel S, Dias E C, Butler P D, Javitt D C. 2012. Consequences of Magnocellular Dysfunction on Processing Attended Information in Schizophrenia. Cerebral Cortex 22:1282-1293.

[57] Woldorff M G, Fox P T, Matzke M, Lancaster J L, Veeraswamy S, Zamarripa F, Seabolt M, Glass T, Gao J H, Martin C C, Jerabek P. 1997. Retinotopic organization of the early visual-spatial attention effects as revealed by PET and ERPs. Human Brain Mapping 5:280-286.

[58] Martinez A, Anllo-Vento L, Sereno M I, Frank L R, Buxton R B, Dubowitz D J, Wong E C, Hinrichs H, Heinze H J, Hillyard S A. 1999. Involvement of striate and extrastriate visual cortical areas in spatial attention. Nat Neurosci 2:364-369.

[59] Di Russo F, Martinez A, Hillyard S A. 2003. Source analysis of event-related cortical activity during visuo-spatial attention. Cereb Cortex 13:486-499.

[60] Martinez A, Hillyard S A, Dias E C, Hagler D J, Jr., Butler P D, Guilfoyle D N, Jalbrzikowski M, Silipo G, Javitt D C. 2008. Magnocellular pathway impairment in schizophrenia: evidence from functional magnetic resonance imaging. Journal of Neuroscience 28:7492-7500.

[61] Chen Y. 2011. Abnormal visual motion processing in schizophrenia: a review of research progress. Schizophr Bull 37:709-715.

[62] Chen Y, Nakayama K, Levy D L, Matthysse S, Holzman P S. 1999. Psychophysical isolation of a motion-processing deficit in schizophrenics and their relatives and its association with impaired smooth pursuit. Proc Natl Acad Sci USA 96:4724-4729.

[63] Slaghuis W L, Holthouse T, Hawkes A, Bruno R. 2007. Eye movement and visual motion perception in schizophrenia I I: Global coherent motion as a function of target velocity and stimulus density. Exp Brain Res 182:415-426.

[64] Zeki S M. 1974. Functional organization of a visual area in the posterior bank of the superior temporal sulcus of the rhesus monkey. The Journal of physiology 236: 549-573.

[65] Albright T D. 1984. Direction and orientation selectivity of neurons in visual area M T of the macaque. J Neurophysiol 52:1106-1130.

[66] Born R T, Bradley D C. 2005. Structure and function of visual area M T. Annu Rev Neurosci 28:157-189.

[67] Livingstone M, Hubel D. 1988. Segregation of form, color, movement, and depth: anatomy, physiology, and perception. Science 240:740-749.

[68] Merigan W H, Maunsell J H R. 1993. How parallel are the primate visual pathways? In: Cowan W M, Shooter E M, Stevens C F, Thompson R F, editors. Ann Rev Neuroscience Palo Alto, CA: Annual Reviews, Inc. p 369-402.

[69] Nassi J J, Lyon D C, Callaway E M. 2006. The parvocellular LGN provides a robust disynaptic input to the visual motion area M T. Neuron 50:319-327.

[70] Braus D F, Weber-Fahr W, Tost H, Ruf M, Henn F A. 2002. Sensory information processing in neuroleptic-naive first-episode schizophrenic patients: a functional magnetic resonance imaging study. Arch Gen Psychiatry 59:696-701.

[71] Kim D, Wylie G, Pasternak R, Butler P D, Javitt D C. 2006. Magnocellular contributions to impaired motion processing in schizophrenia. Schizophr Res 82:1-8.

[72] Chen Y, Nakayama K, Levy D, Matthysse S, Holzman P. 2003. Processing of global, but not local, motion direction is deficient in schizophrenia. Schizophr Res 61:215-227.

[73] Chen Y, Levy D L, Sheremata S, Holzman P S. 2004. Compromised late-stage motion processing in schizophrenia. Biol Psychiatry 55:834-841.

[74] Kuba M. 2006. Motion-onset Visual Evoked Potentials and their Diagnostic Application. In. Hradec Kralove: Nucleus H K.

[75] Kuba M, Kubova Z, Kremlacek J, Langrova J. 2007. Motion-onset VEPs: characteristics, methods, and diagnostic use. Vision Res 47:189-202.

[76] Probst T, Plendl H, Paulus W, Wist E R, Scherg M. 1993. Identification of the visual motion area (area V5) in the human brain by dipole source analysis. Exp Brain Res 93:345-351.

[77] Ahlfors S P, Simpson G V, Dale A M, Belliveau J W, Liu A K, Korvenoja A, Virtanen J, Huotilainen M, Tootell R B, Aronen H J, Ilmoniemi R J. 1999. Spatiotemporal activity of a cortical network for processing visual motion revealed by MEG and fMRI. J Neurophysiol 82:2545-2555.

[78] Bach M, Ullrich D. 1997. Contrast dependency of motion-onset and pattern-reversal VEPs: interaction of stimulus type, recording site and response component. Vision Res 37:1845-1849.

[79] McKeefry D J. 2002. The influence of stimulus chromaticity on the isoluminant motion-onset VEP. Vision Res 42:909-922.

[80] Regan D. 1989. Human Brain Electrophysiology: Evoked Potentials and Evoked Magnetic Fields in Science and Medicine. New York: Elsevier.

[81] Rice D M, Potkin S G, Jin Y, Isenhart R, Heh C W, Sramek J, Costa J, Sandman C A. 1989. EEG alpha photic driving abnormalities in chronic schizophrenia. Psychiatry Res 30:313-324.

[82] Jin Y, Sandman C A, Wu J C, Bernat J, Potkin S G. 1995. Topographic analysis of EEG photic driving in normal and schizophrenic subjects. Clin Electroencephalogr 26:102-107.

[83] Jin Y, Castellanos A, Solis E R, Potkin S G. 2000. EEG resonant responses in schizophrenia: a photic driving study with improved harmonic resolution. Schizophr Res 44:213-220.

[84] Krishnan G P, Vohs J L, Hetrick W P, Carroll C A, Shekhar A, Bockbrader M A, O'Donnell B F. 2005. Steady state visual evoked potential abnormalities in schizophrenia. Clin Neurophysiol 116:614-624.

[85] Brenner C A, Krishnan G P, Vohs J L, Ahn W Y, Hetrick W P, Morzorati S L, O'Donnell B F. 2009. Steady state responses: electrophysiological assessment of sensory function in schizophrenia. Schizophr Bull 35:1065-1077.

[86] Goldstein M R, Peterson M J, Sanguinetti J L, Tononi G, Ferrarelli F. 2015. Topographic deficits in alpha-range resting EEG activity and steady state visual evoked responses in schizophrenia. Schizophr Res 168:145-152.

[87] Jin Y, Potkin S G, Rice D, Sramek J, Costa J, Isenhart R, Heh C, Sandman C A. 1990. Abnormal EEG responses to photic stimulation in schizophrenic patients. Schizophr Bull 16:627-634.

[88] Jin Y, Potkin S G, Sandman C A, Bunney W E, Jr. 1997. Electroencephalographic photic driving in patients with schizophrenia and depression. Biol Psychiatry 41:496-499.

[89] Lopes da Silva F H, Vos J E, Mooibroek J, Van Rotterdam A. 1980. Relative contributions of intracortical and thalamo-cortical processes in the generation of alpha rhythms, revealed by partial coherence analysis. Electroencephalogr Clin Neurophysiol 50:449-456.

[90] Goldman R I, Stern J M, Engel J, Jr., Cohen M S. 2002. Simultaneous EEG and fMRI of the alpha rhythm. Neuroreport 13:2487-2492.

[91] Liu Z, de Zwart J A, Yao B, van Gelderen P, Kuo L W, Duyn J H. 2012. Finding thalamic BOLD correlates to posterior alpha EEG. Neuroimage 63:1060-1069.

[92] Tan H R, Lana L, Uhlhaas P J. 2013. High-frequency neural oscillations and visual processing deficits in schizophrenia. Frontiers in psychology 4:621.

[93] Lisman J. 2016. Low-Frequency Brain Oscillations in Schizophrenia. JAMA Psychiatry 73:298-299.

[94] Mishra J, Martinez A, Schroeder C E, Hillyard S A. 2012. Spatial attention boosts short-latency neural responses in human visual cortex. Neuroimage 59:1968-1978.

[95] First M B, Spitzer R L, Gibbon M, Williams J B W. 1997. Structured Clinical Interview for DSM-IV Axis I Disorders—Patient Edition. In. New York: New York State Psychiatric Institute.

[96] Kay S, Opler L, Fiszbein A. 1992. The Positive and Negative Syndrome Scale (PANSS) Manual. Toronto: Multi-Health Systems, Inc.

[97] Ammons R, Ammons C. 1962. The Quick Test (Q T): provisional manual. Psychological Report 11:111-162.

[98] Woldorff M G, Liotti M, Seabolt M, Busse L, Lancaster J L, Fox P T. 2002. The temporal dynamics of the effects in occipital cortex of visual-spatial selective attention. Brain Res Cogn Brain Res 15:1-15.

[99] Lakatos P, Shah A S, Knuth K H, Ulbert I, Karmos G, Schroeder C E. 2005. An oscillatory hierarchy controlling neuronal excitability and stimulus processing in the auditory cortex. J Neurophysiol 94:1904-1911.

[100] Delorme A, Makeig S. 2004. EEGLAB: an open source toolbox for analysis of single-trial EEG dynamics including independent component analysis. J Neurosci Methods 134:9-21.

[101] Lopez-Calderon J, Luck S J. 2014. ERPLAB: an open-source toolbox for the analysis of event-related potentials. Front Hum Neurosci 8:213.

[102] Tootell R B, Reppas J B, Kwong K K, Malach R, Born R T, Brady T J, Rosen B R, Belliveau J W. 1995. Functional analysis of human M T and related visual cortical areas using magnetic resonance imaging. Journal of Neuroscience 15:3215-3230.

[103] Cox R W. 1996. AFNI—Software for analysis and visualization of functional magnetic resonance neuroimages. Computers and Biomedical Research 29:162-173.

[104] Talairach J, Tournoux P. 1988. Co-Planar Stereotaxic Atlas of the Human Brain: 3-Dimensional proportional system: An approach to cerebral imaging. New York, NY: Thieme.

[105] Kriegeskorte N, Simmons W K, Bellgowan P S, Baker C I. 2009. Circular analysis in systems neuroscience: the dangers of double dipping. Nat Neurosci 12:535-540.

[106] Brittain P J, Surguladze S, McKendrick A M, Ffytche D H. 2010. Backward and forward visual masking in schizophrenia and its relation to global motion and global form perception. Schizophr Res 124:134-141.

[107] Byne W, Buchsbaum M S, Mattiace L A, Hazlett E A, Kemether E, Elhakem S L, Purohit D P, Haroutunian V, Jones L. 2002. Postmortem assessment of thalamic nuclear volumes in subjects with schizophrenia. Am J Psychiatry 159:59-65.

[108] Kemether E M, Buchsbaum M S, Byne W, Hazlett E A, Haznedar M, Brickman A M, Platholi J, Bloom R. 2003. Magnetic resonance imaging of mediodorsal, pulvinar, and centromedian nuclei of the thalamus in patients with schizophrenia. Arch Gen Psychiatry 60:983-991.

[109] Byne W, Fernandes J, Haroutunian V, Huacon D, Kidkardnee S, Kim J, Tatusov A, Thakur U, Yiannoulos G. 2007. Reduction of right medial pulvinar volume and neuron number in schizophrenia. Schizophr Res 90:71-75.

[110] Buchsbaum M S, Someya T, Teng C Y, Abel L, Chin S, Najafi A, Haier R J, Wu J, Bunney W E, Jr. 1996. PET and MRI of the thalamus in never-medicated patients with schizophrenia. Am J Psychiatry 153:191-199.

[111] Hazlett E A, Buchsbaum M S, Kemether E, Bloom R, Platholi J, Brickman A M, Shihabuddin L, Tang C, Byne W. 2004. Abnormal glucose metabolism in the mediodorsal nucleus of the thalamus in schizophrenia. Am J Psychiatry 161:305-314.

[112] Lakatos P, O'Connell M N, Barczak A, Mills A, Javitt D C, Schroeder C E. 2009. The leading sense: supramodal control of neurophysiological context by attention. Neuron 64:419-430.

[113] Lakatos P, Schroeder C, Leitman D I, Javitt D. 2013. Predictive Suppression of Cortical Excitability and Its Deficit in Schizophrenia. Journal of Neuroscience 33:11692-11702.

[114] Rose V L. 1997. APA practice guideline for the treatment of patients with schizophrenia. American family physician 56:1217-1220.

What is claimed is:

1. A non-transitory computer-accessible medium having stored thereon computer executable instructions for generating diagnostic data associated with a likelihood of at least one patient developing at least one mental disease, wherein, when a computer arrangement executes the instructions, the computer arrangement is configured to perform procedures comprising:
   providing at least one visual pattern to the at least one patient;
   receiving, by at least one computer processor, electroencephalogram (EEG) information from the at least one patient that is based on the at least one visual pattern;
   generating, using the at least one computer processor, the data by applying a motion-onset event-related spectral perturbation (ERSP) procedure on the EEG information;
   detecting a presence of an early state of a neurodegenerative disease based on a likelihood of amyloid positivity from balanced processing deficits that are based on the generated data; and
   directing a specific treatment for the early state of the neurodegenerative disease targeting an amyloid pathology to the at least one patient based on the generated data.

2. The non-transitory computer-accessible medium of claim 1, wherein the computer arrangement is further configured to generate the data by utilizing at least one of (i) a stimulus-onset ERSP procedure, or (ii) a steady-state evoked potential (ssVEP) procedure to the EEG information.

3. The non-transitory computer-accessible medium of claim 1, wherein the at least one visual pattern includes at least one of a low spatial frequency (LSF) stimulus or a high spatial frequency (HSF) stimulus.

4. The non-transitory computer-accessible medium of claim 3, wherein the computer arrangement is configured to segregate responses in the EEG information from a subcortical magnocellular and parvocellular visual pathways based on the at least one of the LSF stimulus or the HSF stimulus.

5. The non-transitory computer-accessible medium of claim 1, wherein the computer arrangement is configured to generate the data by decomposing the neurological responses in the EEG information into a plurality of underlying spectral frequencies.

6. The non-transitory computer-accessible medium of claim 5, wherein the underlying spectral frequencies correspond to at least one of (i) a predominant event-related spectral perturbation (ERSP) response, (ii) a motion-onset N2m ERSP component, or (iii) a steady-state evoked potential (ssVEP).

7. The non-transitory computer-accessible medium of claim 6, wherein the ERSP response is in a first frequency range of about 4 Hz to about 7 Hz which is a theta frequency, the motion-onset N2m component is in a second frequency range of about 1 Hz to about 4 Hz which is a delta frequency, and the ssVEP is at about 8 Hz.

8. The non-transitory computer-accessible medium of claim 6, wherein the ERSP responses are transient ERSPs.

9. The non-transitory computer-accessible medium of claim 6, wherein the ERSP response is in a theta frequency range of about 4 Hz to about 7 Hz.

10. The non-transitory computer-accessible medium of claim 6, wherein the motion-onset N2m ERSP component is in a delta frequency range of about 1 Hz to about 4 Hz.

11. The non-transitory computer-accessible medium of claim 1, wherein the data is related to at least one of Alzheimer's disease or Schizophrenia.

12. The non-transitory computer-accessible medium of claim 1, wherein the data is an amyloid distribution.

13. The non-transitory computer-accessible medium of claim 1, wherein the computer arrangement is further configured to initiate a motion onset component after providing the at least one visual pattern.

14. The non-transitory computer-accessible medium of claim 13, wherein the motion onset component is a N2m component.

15. The non-transitory computer-accessible medium of claim 1, wherein the computer arrangement is further configured to initiate a stimulus counterphase reversal after ending the motion onset component.

16. The non-transitory computer-accessible medium of claim 1, wherein the at least one visual pattern includes a vertical grating configured to segregate responses from subcortical magnocellular and parvocellular visual pathways.

17. The non-transitory computer-accessible medium of claim 1, wherein the EEG information is obtained using bipolar electrodes on left and right outer canthi.

18. The non-transitory computer-accessible medium of claim 1, wherein the at least one visual pattern includes a motion-onset that is delayed by about 400 ms from a stimulus onset.

19. The non-transitory computer-accessible medium of claim 1, wherein the EEG is epoched surrounding an onset of each of a plurality of stimulus in the visual pattern.

20. The non-transitory computer-accessible medium of claim 19, wherein the epoch surrounding the onset of each of the plurality of stimulus in the visual pattern is from −1000 ms to 3000 ms.

21. The non-transitory computer-accessible medium of claim 1, wherein the generation of the data is based on the EEG information that was generated as a response from the at least one patient that is based on the at least one visual pattern.

22. The non-transitory computer-accessible medium of claim 1, wherein the computer arrangement is further configured to:
decompose, in a neuro-oscillatory approach by the processor, one or more neurophysiological responses of the EEG information into underlying spectral domain information or time domain information prior to generating the data.

23. The non-transitory computer-accessible medium of claim 1, wherein the neurodegeneration treatment is Alzheimer's treatment.

24. The non-transitory computer-accessible medium of claim 1, further configured to perform:
analyzing one or more neural substrates and timings of motion-processing deficits.

25. The non-transitory computer-accessible medium of claim 24, wherein the neural substrates comprise dysfunction in a plurality of magnocellular pathways and parvocellular pathways, are observed via one or more cortical regions with a plurality of EEG electrodes.

26. The non-transitory computer-accessible medium of claim 24, wherein one or more timings comprise a start/stop time as well as a transient duration of the motion-processing deficits.

27. The non-transitory computer-accessible medium of claim 1, further configured to perform:
translating motion-processing deficit information to data in a user-readable format by training a regression analysis on a plurality of standard amyloid PET and cognitive test results.

28. The non-transitory computer-accessible medium of claim 1, one or more successive stimuli are separated by a consistent duration to reduce habituation.

29. The non-transitory computer-accessible medium of claim 1, wherein the at least one visual pattern comprises a visual stimulus type comprising one or more of low spatial frequency, high spatial frequency, low contrast, and high contrast, the visual stimulus type selected to bias activity to a plurality of different neural substrates.

30. The non-transitory computer-accessible medium of claim 1, wherein the detecting of the neurodegenerative disease is accomplished by connecting one or more alpha oscillation impairments in the generated data to a problem with a thalamic pulvinar nucleus of the patient.

31. A system for generating data associated with a likelihood of at least one patient developing at least one mental disease, comprising:
a computer hardware arrangement configured to:
provide at least one visual pattern to the at least one patient;
receive, by at least one computer processor, electroencephalogram (EEG) information from the at least one patient that is based on the at least one visual pattern;
generate, by the at least one computer processor, the data by applying a motion-onset event-related spectral perturbation (ERSP) procedure on the EEG information;
detect a presence of an early state of a neurodegenerative disease based on a likelihood of amyloid positivity from balanced processing deficits that are based on the generated data; and
direct a specific treatment for the early state of the neurodegenerative disease targeting an amyloid pathology to the at least one patient based on the generated data.

32. The system of claim 31, wherein the at least one visual pattern includes a vertical grating configured to segregate responses from subcortical magnocellular and parvocellular visual pathways.

33. The system of claim 31, wherein the EEG information is obtained using bipolar electrodes on left and right outer canthi.

34. A method for generating data associated with a likelihood of at least one patient developing at least one mental disease, comprising:
providing at least one visual pattern to the at least one patient;
receiving, by at least one computer processor, electroencephalogram (EEG) information from the at least one patient that is based on the at least one visual pattern;
using the at least one computer processor, generating the data by applying a motion-onset event-related spectral perturbation (ERSP) procedure on the EEG information;
detecting a presence of an early state of a neurodegenerative disease based on a likelihood of amyloid positivity from balanced processing deficits that are based on the generated data; and
directing a specific treatment for the early state of the neurodegenerative disease targeting an amyloid pathology to the at least one patient based on the generated data.

35. The method of claim 34, wherein the at least one visual pattern includes a vertical grating configured to segregate responses from subcortical magnocellular and parvocellular visual pathways.

36. The method of claim 34, wherein the EEG information is obtained using bipolar electrodes on left and right outer canthi.

37. A device for providing at least one visual stimulation to at least one patient, comprising:
a display arrangement configured to provide the at least one visual stimulation to the at least one patient;
an EEG arrangement configured to generate EEG information based on the at least one visual stimulation provided to the at least one patient; and
at least one computer processor configured to:
generate data by applying a motion-onset event-related spectral perturbation (ERSP) procedure on the EEG information,
detect a presence of an early state of a neurodegenerative disease based on a likelihood of amyloid positivity from balanced processing deficits that are based on the generated data; and
direct a specific treatment for the early state of the neurodegenerative disease targeting an amyloid pathology to the at least one patient based on the generated data.

38. The device of claim 37, wherein the at least one pattern includes at least one of (i) a low spatial frequency stimulus and a high spatial frequency stimulus, or (ii) a vertical grating.

39. The device of claim 37, wherein the at least one visual pattern includes a vertical grating configured to segregate responses from subcortical magnocellular and parvocellular visual pathways.

40. The device of claim 37, wherein the EEG information is obtained using bipolar electrodes on left and right outer canthi.

41. A non-transitory computer-accessible medium having stored thereon computer executable instructions for generating data associated with a likelihood of at least one patient developing at least one mental disease, wherein, when a computer arrangement executes the instructions, the computer arrangement is configured to perform procedures comprising:
providing at least one visual pattern to the at least one patient;
generating at least one signal, by a plurality of electrodes and the at least one computer processor, concurrently with or immediately after the at least one visual pattern is provided to the at least one patient so as to (i) generate a plurality of electrical impulses in the patient's brain, and (ii) record response thereto resulting from the at least one patient being subjected to the at least one visual pattern;
receiving, by at least one computer processor, the at least one generated signal from the at least one patient that is based on the at least one visual pattern;
generating, using the at least one computer processor, the diagnostic data by applying a motion-onset event-related spectral perturbation (ERSP) procedure on the EEG information;
detecting a presence of an early state of a neurodegenerative disease based on a likelihood of amyloid positivity from balanced processing deficits that are based on the generated data; and
directing a specific treatment for the early state of the neurodegenerative disease targeting an amyloid pathology to the at least one patient based on the generated data.

42. A non-transitory computer-accessible medium having stored thereon computer executable instructions for generating data indicative of an amyloid positivity in at least one patient, associated with a likelihood of developing a neurodegenerative disease, wherein, when executed by a computer arrangement, the instructions configure the computer arrangement to:
provide at least two types of visual stimuli to the at least one patient, wherein one of the at least two types of the visual stimuli targets the magnocellular pathway and another one of the at least two types of the visual stimuli targets a parvocellular pathway;
receive, via at least one computer processor, electroencephalogram (EEG) information from the at least one patient, derived from responses to the at least two type of the visual stimulus;
generate the data by applying a motion-onset event-related spectral perturbation (ERSP) procedure to the EEG information;
assess, via an analysis of EEG responses associated with the responses to the at least two type of the visual stimulus, whether the patient exhibits balanced processing deficits across the magnocellular and parvocellular pathways, indicating a cortical dysfunction;
determine, based on the assessment of the balanced processing deficits, a likelihood of the amyloid positivity in the patient, wherein the amyloid positivity is associated with cortical issues and an increased risk of the neurodegenerative disease;
detect a presence of an early state of the neurodegenerative disease based on the data;
direct and facilitate an initiation of a specific preventative treatment or a therapeutic treatment for the early state of the neurodegenerative disease targeting an amyloid pathology for the patient based on a detection of the amyloid positivity.

43. The non-transitory computer-accessible medium of claim 42, wherein the assessment of whether the patient exhibits balanced deficits in processing stimuli across the magnocellular and parvocellular pathways is performed by evaluating a degree of difficulty encountered with one or more types of the visual stimuli that each pathway is sensitive to, and wherein the balanced deficits are indicative of a cortical issue due to a role of a cortex in integrating and processing information from the magnocellular and parvocellular pathways.

44. The non-transitory computer-accessible medium of claim 42, wherein the neurodegenerative disease is Alzheimer's disease, and wherein the specific treatment is tailored for a prevention or a mitigation of Alzheimer's disease based on the detected amyloid positivity.

45. The non-transitory computer-accessible medium of claim 42, wherein the one of the at least two types of the visual stimuli targeting the magnocellular pathway is characterized by features selected from a group consisting of low spatial frequency, low contrast, and movement, and wherein the other one of the at least two types of the visual stimuli targeting the parvocellular pathway is characterized by features of high spatial frequency and high contrast.

46. A method for determining a likelihood of a patient developing symptoms, or a change to existing symptoms, associated with organic brain disease, comprising:
attaching a plurality of electroencephalogram (EEG) sensors to the patient;
connecting the plurality of EEG sensors to an EEG device;
initiating the EEG device and while the EEG device is running, providing a visual stimulus to the patient, where the visual stimulus is one of: (i) an optimized stimulation, (ii) a time-frequency analytic, (iii) a low spatial frequency, and (iv) a high spatial frequency;
gathering EEG data from approximately 400 ms after the stimulus until approximately 600 ms after the stimulus;
examining the EEG data for Stimulus-Driven Data ("SDD") using one or more of: a time frequency neuro-oscillatory approach; an ERSP response in the theta frequency range; an ERSP response in the delta range; and a steady-state evoked potential at an 8 Hz steady-state stimulation frequency;
comparing the SDD to a data source associating SDD with a specific probability, or range of probabilities, of developing an organic brain disease;
detecting a presence of an early state of a neurodegenerative disease based on a likelihood of amyloid positivity from balanced processing deficits based on the SDD; and
directing a specific treatment for the early state of the neurodegenerative disease targeting an amyloid pathology to the at least one patient based on the generated data.

* * * * *